(12) United States Patent
Seehra et al.

(10) Patent No.: US 6,630,496 B1
(45) Date of Patent: *Oct. 7, 2003

(54) INHIBITORS OF PHOSPHOLIPASE ENZYMES

(75) Inventors: Jasbir S. Seehra, Lexington, MA (US); Neelu Kaila, Natick, MA (US); John C. McKew, Arlington, MA (US); Jean E. Bemis, Arlington, MA (US); YiBin Xiang, Acton, MA (US); Lihren Chen, Cambridge, MA (US)

(73) Assignee: Genetics Institute LLC, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/645,042

(22) Filed: Aug. 24, 2000

Related U.S. Application Data

(63) Continuation-in-part of application No. 09/030,102, filed on Feb. 25, 1998, now abandoned, which is a continuation-in-part of application No. 08/918,400, filed on Aug. 26, 1997, now abandoned.
(60) Provisional application No. 60/092,111, filed on Aug. 26, 1996.

(51) Int. Cl.$^7$ .................. C07D 417/06; A61K 31/404; A61K 31/427
(52) U.S. Cl. .................. 514/369; 548/181; 548/183
(58) Field of Search .................. 548/492, 183, 548/181; 514/369

(56) References Cited

U.S. PATENT DOCUMENTS

| | | | | |
|---|---|---|---|---|
| 4,192,880 | A | 3/1980 | Tsukamoto et al. | 424/273 |
| 4,235,871 | A | 11/1980 | Papahadjopoulos et al. | 424/19 |
| 4,271,263 | A | 6/1981 | Goettert | 430/522 |
| 4,501,728 | A | 2/1985 | Geho et al. | 424/38 |
| 4,654,360 | A | 3/1987 | Greenhouse et al. | 514/418 |
| 4,734,421 | A | 3/1988 | Hammond et al. | 514/274 |
| 4,737,323 | A | 4/1988 | Martin et al. | 264/4.3 |
| 4,772,703 | A | 9/1988 | Musser et al. | 544/283 |
| 4,837,028 | A | 6/1989 | Allen | 424/450 |
| 4,920,140 | A | 4/1990 | Shroot et al. | 514/394 |
| 4,957,932 | A | 9/1990 | Young et al. | 514/375 |
| 5,081,145 | A | 1/1992 | Seehra et al. | 514/419 |
| 5,084,575 | A | 1/1992 | Kreft et al. | 546/172 |
| 5,141,950 | A | 8/1992 | Nakane et al. | 514/395 |
| 5,166,170 | A | 11/1992 | Tegeler et al. | 514/415 |
| 5,212,195 | A | 5/1993 | Clark et al. | 514/381 |
| 5,218,124 | A | 6/1993 | Failli et al. | 548/180 |
| 5,250,565 | A | 10/1993 | Brooks et al. | 514/443 |
| 5,288,743 | A | 2/1994 | Brooks et al. | 514/365 |
| 5,314,880 | A | 5/1994 | Whittaker et al. | 514/80 |
| 5,319,097 | A | 6/1994 | Holohan et al. | 548/507 |
| 5,322,776 | A | 6/1994 | Knopf et al. | 435/69.1 |
| 5,332,755 | A | 7/1994 | Butler et al. | 514/415 |
| 5,354,677 | A | 10/1994 | Knopf et al. | 435/198 |
| 5,391,758 | A | 2/1995 | Bernstein et al. | 548/253 |
| 5,420,289 | A | 5/1995 | Musser et al. | 548/159 |
| 5,424,329 | A | 6/1995 | Boschelli et al. | 514/228.5 |
| 5,434,150 | A | 7/1995 | Austel et al. | 514/228.5 |
| 5,446,059 | A | 8/1995 | Rocher et al. | 514/374 |
| 5,459,152 | A | 10/1995 | Summers et al. | 514/338 |
| 5,482,960 | A | 1/1996 | Berryman et al. | 514/414 |
| 5,482,963 | A | 1/1996 | Holohan et al. | 514/415 |
| 5,486,525 | A | 1/1996 | Summers, Jr. et al. | 514/303 |
| 5,504,216 | A | 4/1996 | Holohan et al. | 548/507 |
| 5,567,711 | A | 10/1996 | Sheppard et al. | 514/303 |
| 5,578,634 | A | 11/1996 | Bach et al. | 514/419 |
| 5,599,930 | A | 2/1997 | Romero et al. | 544/121 |
| 5,654,305 | A | 8/1997 | Sheppard et al. | 514/253 |
| 5,654,326 | A | 8/1997 | Bach et al. | 514/419 |
| 5,684,034 | A | 11/1997 | Bach et al. | 514/419 |
| 5,741,804 | A | 4/1998 | Keenan et al. | 514/394 |

FOREIGN PATENT DOCUMENTS

| EP | 780389 | * | 6/1997 |
| WO | 9513266 | | 5/1995 |
| WO | WO 96/26207 | * | 8/1996 |

OTHER PUBLICATIONS

Heller et al., PubMed Abstract (Drugs 55(4):487–96), 1998.*
Farooqui et al., PubMed Abstract (Brain Res Bull 49(3): 139–53), 1999.*
Smith, W. *Biochem. J.* 1989, 259, 315.
Wasserman, S. *Hospital Practice* 1988, 49.
Chang, J. et al. *Biochemical Pharmacology* 1987, 36, 2429.
Dennis, E. *Drug Development Research* 1987, 10, 205.
Seilhamer, J. et al. *J. Bio. Chem.* 1989, 10, 5335.
Kramer, R. et al. *J. Bio. Chem.* 1989, 10, 5768.
Kanda, A. et al. *Biochem. and Biophys. Research Comm.* 1989, 163, 42.
Burch, R. et al. *Proc. Natl. Acad. Sci. USA* 1987, 84, 6374.
Leslie, C. et al. *Bioch. et Biophys. Acta* 1988, 963, 476.
Bligh, E. et al. *Can. J. Biochem. Physiol.* 1959, 37, 911.
Kutkevicius, S. et al. *Chem. Abstract* 1982, 96: 85391.
Gadient et al. *Chem. Abstract* 1980, 93: 71555.
Griffin, R. et al. *Chem. Abstract* 1997, 126: 212151.
Yamaguchi *Chem. Abstract* 1996, 124: 329940b.
Geban et al. *Chem. Abstract* 1996, 124: 219398y.
Aldrich Catalogue, 1994, pp. 1116.
Cox et al. *Chem. Abstract* 1988, 108: 94553.
Rao et al. *Chem. Abstract* 1980, 93: 167168t.
Inoue et al. *Chem. Abstract* 1975, 82: 16840.
*Chem. Abstract* 1972, 77: 24824.
Kuranari et al. *Chem. Abstract* 1968, 68: 29698y.
Aka et al. *Chem. Abstract* 1967, 66: 95044s.
Samuelsson et al. *Science* 1987, 1237, 1171.
Ramesha, C. et al. *Anal. Biochem.* 1991, 192, 173.

* cited by examiner

*Primary Examiner*—Deepak Rao
(74) *Attorney, Agent, or Firm*—Joseph M. Mazzarese

(57) ABSTRACT

This invention provides substituted indole and indoline compounds useful in inhibiting phospholipase activity, particularly including cytosolic phospholipase A2 (cPLA2) activity, as well as pharmaceutical compositions containing the compounds and methods of using them to treat various maladies, including pain and inflammatory conditions.

18 Claims, 13 Drawing Sheets

METHOD A

METHOD B

R = alkoxy, benzyloxy, phenoxy, halogen, CN, $NO_2$, alkyl or aryl
R' = alkyl, benzyl, alkenyl, alkinyl
R" = halogen, CN, alkyl alkoxy, alkoxycarbonyl, amido, acyl, H, OH

METHOD C

R = alkoxy, benzyloxy, phenoxy, halogen, CN, NO$_2$, alkyl or aryl
R' = alkyl, benzyl, alkenyl, alkinyl
R" = alkyl, aryl
R'" = alkyl, aryl, H, SO$_2$R, COR

METHOD D

X = O, S

R = alkoxy, benzyloxy, phenoxy, halogen, CN, $NO_2$, alkyl or aryl

R' = alkyl, benzyl, alkenyl, alkinyl

R" = alkyl, aryl

R'" = alkyl, aryl

METHOD E n = 0-1

R = alkoxy, benzyloxy, phenoxy, halogen, CN, $NO_2$, alkyl or aryl

R' = alkyl, alkenyl

R" = H, OH, alkoxy, alkyl, alkenyl

R'" = H, OH, halogen, alkoxy, carboxyl, amido, alkyl, $NO_2$

R"" = alkyl, alkenyl

METHOD F

R = alkoxy, benzyloxy, phenoxy, halogen, CN, NO$_2$, alkyl or aryl

R', R" and R'" are independent alkyl, alkenyl, aryl groups

METHOD G n = 1 or 2

R = alkoxy, benzyloxy, phenoxy, halogen, CN, $NO_2$, alkyl or aryl

R' and R" are independent alkyl, alkenyl, aryl groups

METHOD H

R = alkoxy, benzyloxy, phenoxy, halogen,
CN, NO₂, alkyl or aryl

METHOD I

METHOD J

R = H, alkoxy, benzyloxy, phenoxy, halogen, CN, NO₂, alkyl or aryl

R' = alkyl, alkenyl

R" = alkyl, alkenyl

METHOD K

R, R' = independent H, alkyl, or aryl groups

R" = alkyl, alkenyl aryl

METHOD L

X = O or S

R = acyl, kyl, alkenyl

R', R" = independent alkyl, aryl or substituted aryl

METHOD M

R = alkoxy, benzyloxy, phenoxy, halogen, CN, NO$_2$, alkyl or aryl

INHIBITORS OF PHOSPHOLIPASE ENZYMES

This application is a continuation-in-part of application Ser. No. 09/030,102, filed Feb. 25, 1998, now abandoned, which is a continuation-in-part of application Ser. No 08/918,400, filed Aug. 26, 1997, now abandoned, which claims the benefit of Provisional Application No. 60/092,111, filed Aug. 26, 1996.

BACKGROUND OF THE INVENTION

The present invention relates to chemical inhibitors of the activity of various phospholipase enzymes, particularly phospholipase $A_2$ enzymes.

Leukotrienes and prostaglandins are important mediators of inflammation. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experience by asthmatics [See, e.g. B. Samuelson et al., Science, 237:1117–76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, Biochem. J., 259: 325–324 (1989) from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid which is fed into these two distinct inflammatory pathways is released from the sn-2 position of membrane phospholipids by phospholipase $A_2$ (hereinafter $PLA_2$). The reaction catalyzed by $PLA_2$ is believed to represent the rate-limiting step in the process of lipid mediated biosynthesis and the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49–58 (1998)].

Most anti-inflammatory therapies have focused on preventing production of either protaglandins or leukotrienes from these distinct pathways, but not on all of them. For example, ibuprofen, aspirin and indomethacin are all NSAIDs which inhibit the production of prostaglandins by COX-1/COX-2, but have no effect on the inflammatory production of leukotrienes from arachidonic acid in the other pathways. Conversely, zileuton inhibits only the pathwasy of conversion of arachidonic acid to leukotrienes, witout affecting the production of prostaglandins. None of these widelt-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, Biochem. Pharmacol., 3:2429–2436 (1987)].

A family of $PLA_2$ enzymes characterized by the presence of a secretion signal sequenced and ultimately secreted from the cell have been sequenced and structurally defined. These secreted $PLA_2$ have an approximately 14 kD molecular weight and contain seven disulfide bonds which are necessary for activity. These $PLA_2$s are found in large quantities in mammalian pancreas, bee venom, and various snake venom. [See, e.g., references 13–15 in Chang et al, cited above; and E. A. Dennis, Drug Devel. Res., 10:205–220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, J. Biol. Chem., 264:5335–5338 (1989); R. M. Kramer et al, J. Biol. Chem., 264:5768–5775 (1989); and A. Kando et al, Biochem Biophys. Res. Comm., 163:4248.(1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, Proc. Natl. Acad. Sci. U.S.A., 84:6374–6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 $\mu$mols/min/mg, resistant to reducing conditions, was reported to be associated with the approximately 60 kD molecule. However, this protein was not purified to homogeneity. [See, C. C. Leslie et al, Biochem. Biophys. Acta., 9:476492 (1988)]. The references cited above are incorporated by reference herein for information pertaining to the function of the phospholipase enzymes, particularly $PLA_2$.

A cytosolic phospholipase $A_2$ (hereinafter "$cPLA_2$") has also been identified and cloned. See, U.S. Pat. Nos. 5,322, 776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

Now that several phospholipase enzymes have been identified, it would be desirable to identify chemical inhibitors of the action of enzymes, which inhibitors could be used to treat inflammatory conditions, particularly where inhibition of production of prostaglandins, leukotrienes and PAF are al desired. There remains a need in the art for an identification of such anti-inflammatory agents for therapeutic use in a variety of disease states.

SUMMARY OF THE INVENTION

The present invention provides compounds having a chemical formula selected from the group consisting of:

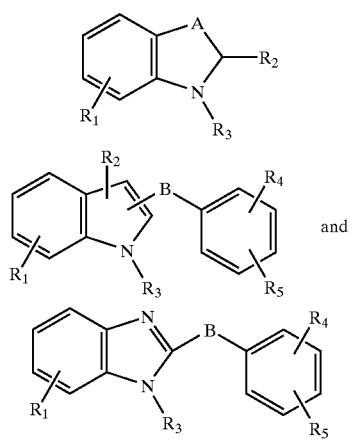

or a pharmaceutically acceptable salt thereof, wherein:
A is independent of any other group and is selected from the group consisting of —$CH_2$— and —$CH_2$—$CH_2$—;
B is independent of any other group and is selected from the group consisting of —$(CH_2)_n$—, —$(CH_2O)_n$—, —$(CH_2S)_n$—, —$(OCH_2)_n$—, —$(SCH_2)_n$—, —$(CH=CH)_n$—, —$(C\equiv C)_n$—, —$CON(R_6)$—, —$N(R_6)CO$—, —O—, —S— and —$N(R_6)$—;
$R_1$ is independent of any other R group and is selected from the group consisting of —X—$R_6$, —H, —OH, halogen, —CN, —$NO_2$, $C_1$-$C_5$ alkyl, alkenyl, alkinyl, aryl and substituted aryl;
$R_2$ is independent of any other R group and is selected from the group consisting of —H, —COOH, —$COR_5$, —$CONR_5R_6$, —$(CH_2)_n$—W—$(CH_2)_m$—Z—$R_5$, —$(CH_2)_n$—W—$R_5$, —Z—$R_5$, $C_1$-$C_{10}$ alkyl, alkenyl and substituted aryl;
$R_3$ is independent of any other R group and is selected from the group consisting of —H, —COOH, —$COR_5$, —$CONR_5R_6$, —$(CH_2)_n$—W—$(CH_2)_m$—Z—$R_5$, —$(CH_2)_n$—W—$R_5$, —Z—$R_5$, $C_1$-$C_{10}$ alkyl, alkenyl and substituted aryl;
$R_4$ is independent of any other R group and is selected from the group consisting of —H, —OH, —$OR_6$, —$SR_6$, —CN, —$COR_6$, —$NHR_6$, —COOH, —$CONR_6R_7$, —$NO_2$, —$CONHSO_2R_8$, $C_1$-$C_5$ alkyl, alkenyl and substituted aryl;
$R_5$ is independent of any other R group and is selected from the group consisting of —H, —OH, —$O(CH_2)_n$ $R_6$, —$SR_6$, —CN, —$COR_6$, —$NHR_6$, —COOH, —$NO_2$, —COOH, —$CONR_6R_7$, —$CONHSO_2R_8$, $C_1$-$C_5$ alkyl, alkenyl, alkinyl, aryl, substituted aryl, —$CF_3$, —$CF_2CF_3$ and

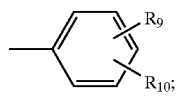

$R_6$ is independent of any other R group and is selected from the group consisting of —H, $C_1$-$C_5$ alkyl, alkenyl, alkinyl, aryl and substituted aryl;
$R_7$ is independent of any other R group and is selected from the group consisting of —H, $C_1$-$C_5$ alkyl, alkenyl, alkinyl, aryl and substituted aryl;
$R_8$ is independent of any other R group and is selected from the group consisting of $C_1$-$C_3$ alkyl, aryl and substituted aryl;

$R_9$ is independent of any other R group and is selected from the group consisting of —H, —OH, a halogen, —CN, —$OR_6$, —COOH, —$CONR_6R_7$, tetrazole, —$CONHSO_2R_8$, —$COR_6$, —$(CH_2)_nCH(OH)R_6$ and —$(CH_2)_nCHR_6R_5$;
$R_{10}$ is independent of any other R group and is selected from the group consisting of —H, —OH, a halogen, —CN, —$OR_6$, —COOH, —$CONR_6R_7$, tetrazole, —$CONHSO_2R_8$, —$COR_6$, —$(CH_2)_nCH(OH)R_6$ and —$(CH_2)_nCHR_6R_5$;
W is, independently each time used including within the same compound, selected from the group consisting of —O—, —S—, —$CH_2$—, —CH=CH—, —C≡C— and —$N(P_6)$—;
X is independent of any other group and is, independently each time used including within the same compound, selected from the group consisting of —O—, —S— and —$N(R_6)$—;
Z is independent of any other group and is, independently each time used including within the same compound, selected from the group consisting of —$CH_2$—, —O—, —S—, —$N(R_6)$—, —CO—, —$CON(R_6)$— and —$N(R_6)CO$—;
m is, independently each time used including within the same compound, an integer from 0 to 4; and
n is independent of m and is, independently each time used including within the same compound, an integer from 0 to 4.

Preferably, the compounds of the invention have phospholipase enzyme inhibiting activity. Other preferrred embodiments include compounds having the following chemical formula:

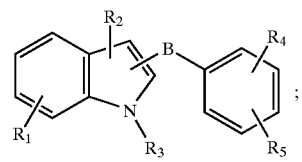

compounds having the following chemical formula:

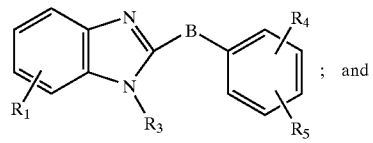

compounds having the following chemical formula:

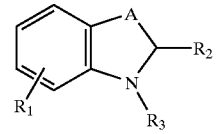

In particularly preferred embodiments, A is —$CH_2$— and $R_2$ is —$(CH_2)_{n-W-(CH2)}_m$—$ZR_5$. These preferred compounds includes those wherein n is 1, m is 1, W is —S— and Z is —CO—; those wherein $R_5$ is —$NHR_6$; those wherein $R_6$ is a substituted aryl group and those wherein said aryl group is substituted with one or more substituents independently selected from the group consisting of a halogen, —$CF_3$, —$CF_2CF_3$, —$(CH_2)_pCOOH$, —$(CH_2)_pCH_3$, —O(CH$_2$)$_p$CH$_3$, —(CH$_2$)$_p$OH, —(CH$_2$)$_p$S(C$_6$H$_6$), —(CH$_2$)$_p$ CONH$_2$ and —CHR$_{11}$COOH, wherein R$_{11}$ is selected froup the group consisting of alkyl, alkenyl, alkynyl, —(CH$_2$)$_p$OH, and -O(CH$_2$)$_p$CH$_3$, and wherein p is an integer from 0 to 4. Other preferred comounds include those wherein R$_1$ is selected from the group consisting of —H and —OCH$_2$(C$_6$H$_6$) and R$_3$ is —COR$_5$, R$_5$ is —OCH$_2$R$_6$ and R$_6$ is a substituted aryl group. In particularly preferred compounds, said aryl group is substituted with one or more substituents selected from the group consisting of —CF$_3$, —CF$_2$CF$_3$ and —C(CH$_3$)$_2$CH$_2$CH$_3$.

Among the compounds of this invention are those of the formula:

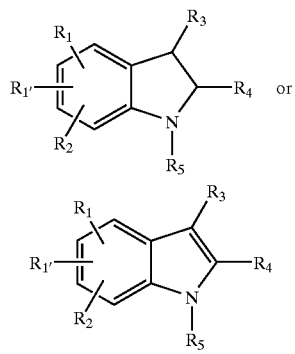

wherein:

R$_1$ and R$_{1'}$ are independently selected from C$_1$-C$_6$ alkyl, —Z—C$_1$-C$_6$ alkyl, phenyl, —(CH$_2$)$_n$—Z—(CH$_2$)$_n$-phenyl, benzyl, —(CH$_2$)$_n$—Z—(CH$_2$)$_n$-benzyl, napthyl, —(CH$_2$)$_n$—Z—(CH$_2$)$_n$-napthyl, pyrimidinyl, —(CH$_2$)$_n$—Z—(CH$_2$)$_n$-pyrimidinyl, the alkyl, phenyl, benzyl, napthyl and pyrimidinyl groups being optionally substituted by from 1 to 3 substituents selected from halogen, C$_1$-C$_6$ alkyl, C$_1$-C$_6$ alkoxy, —NO$_2$, —NH$_2$, —CN, —CF$_3$, or —OH;

Z is O or S;

n is an integer from 0 to 3;

R$_2$ is selected from H, halogen, —CF$_3$, —OH, —C$_1$-C$_{10}$ alkyl, C$_1$-C$_{10}$ alkoxy, —CHO, —CN, —NO$_2$, —NH$_2$, —NH—C$_1$-C$_6$ alkyl, —N(C$_1$-C$_6$ alkyl)$_2$, —N—SO$_2$—C$_1$-C$_6$ alkyl, or —SO$_2$—C$_1$-C$_6$ alkyl, R$_3$ is selected from H, halogen, —CF$_3$, —OH, —C$_1$-C$_{10}$ alkyl, C$_1$-C$_{10}$ alkoxy, —CHO, —C(O)CH$_3$, —C(O)—(CH$_2$)$_n$—CF$_3$, —CN, —NO$_2$, —NH$_2$, —NH—C$_1$-C$_6$ alkyl, —N(C$_1$-C$_6$ alkyl)$_2$, —N—SO$_2$—C$_1$-C$_6$ alkyl, —SO$_2$—C$_1$-C$_6$ alkyl or a moiety of the formula:

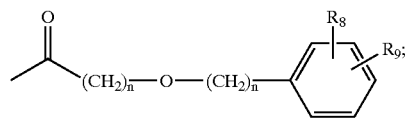

n in each appearance is independently selected as an integer selected from 0–3;

R$^8$ and R$^9$ are independently selected in each appearance from H, —COOH, —(CH$_2$)$_n$—COOH, —(CH$_2$)$_n$—C(O)—COOH, —CF$_3$, —OH, —(CH$_2$)$_n$—C(O)—COOH, —C$_1$-C$_6$ alkyl, —O—C$_1$-C$_6$ alkyl, —NH(C$_1$-C$_6$ alkyl), or —N(C$_1$-C$_6$ alkyl)$_2$;

R$_4$ is selected from —COOH, —(CH$_2$)$_n$—COOH, —(CH$_2$)$_n$—C(O)—COOH, —CH=CH—COOH, tetrazole, —(CH$_2$)$_n$-tetrazole, the moiety —L$^1$—M$^1$ or a moiety of the formulae:

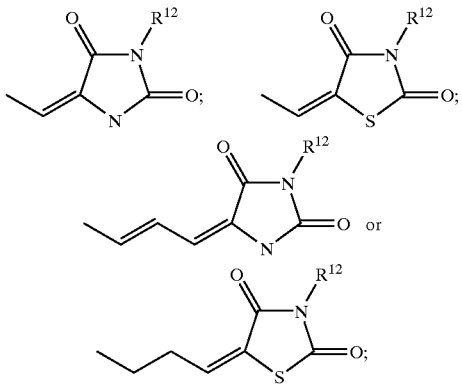

R$^{12}$ is selected from H, —CF$_3$, C$_1$-C$_6$ alkyl, —(CH$_2$)$_n$—C$_3$-C$_6$ cycloalkyl, phenyl, or benzyl, the cycloalkyl, phenyl or benzyl groups being optionally substituted by from 1 to 3 groups selected from halogen, —CF$_3$, —OH, —COOH, —(CH$_2$)$_n$—COOH, —(CH$_2$)$_n$—C(O)—COOH, —C$_1$-C$_6$ alkyl, —O—C$_1$-C$_6$ alkyl, —NH(C$_1$-C$_6$ alkyl), or —N(C$_1$-C$_6$ alkyl)$_2$;

L$^1$ is selected from —(CH$_2$)$_n$—O—, —(CH$_2$)$_n$—S—, —(CH$_2$)$_n$—O—(CH$_2$)$_n$—, —(CH$_2$)$_n$—S—(CH$_2$)$_n$—, —C(O)—O—, —C(O)—(CH$_2$)$_n$—O—, —C(O)—N—, or —(CH$_2$)$_n$—S—(CH$_2$)$_n$—C(O)—N—;

M$^1$ is —COOH or a moiety selected from:

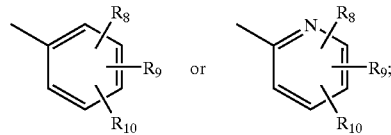

R$^{10}$ is selected from H, —COOH, —(CH$_2$)$_n$—COOH, —(CH$_2$)$_n$—C(O)—COOH, —CF$_3$, —OH, —(CH$_2$)$_n$—C(O)—COOH, —C$_1$-C$_6$ alkyl —O—C$_1$-C$_6$ alkyl,

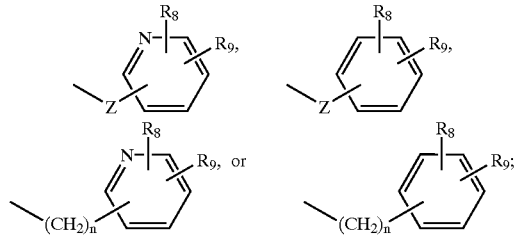

with a proviso that the moiety or combination of moieties comprising R$^3$ include an acidic group selected from carboxylic acid or a moiety of the formulae:

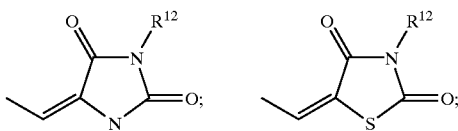

-continued

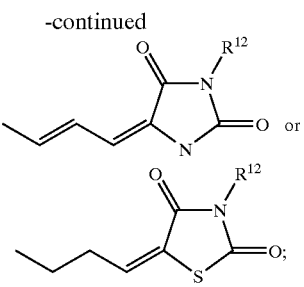

or

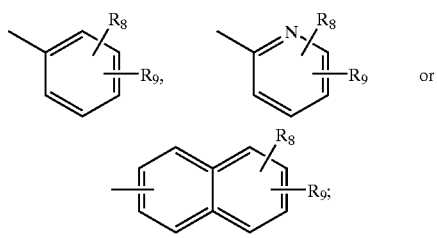

$R_5$ is selected from:
  a) a moiety of the formula —$L^2$—$M^2$;
  $L^2$ is selected from a chemical bond or a bridging group selected from —$(CH_2)_n$—Z—, —$(CH_2)_n$—Z—$(CH_2)_n$—, —C(O)—O—, —C(O)—$(CH_2)_n$—O—, —C(O)—N—, or —$(CH_2)_n$—S—$(CH_2)_n$—C(O)—N—;
  $M^2$ is selected from —$C_1$-$C_6$ alkyl, —O—$C_1$-$C_6$ alkyl,

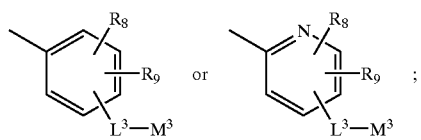

wherein $R^8$ and $R^9$ are as defined above and can be substituted anywhere on the cyclic or bicyclic ring; or
  b) a moiety of the formulae:

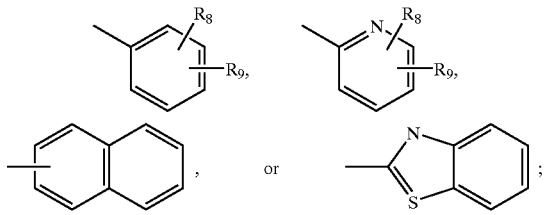

wherein $L^3$ is a chemical bond or a group selected from —$CH_2$—, —$CH_2$—Z—, —C(O)—, —O—, —S—, or —$(CH_2)_n$—Z—$(CH_2)_n$—;
  $M^3$ is selected from —$(CH_2)_n$—$C_3$-$C_5$ cycloalkyl, furanyl, thienyl, pyrrolyl, or a pharmaceutically acceptable salt thereof.

Of the compounds in the group just defined, a preferred subset include those in which the core molecule is an indole. Within the indole group is another subset wherein $R^1$ and $R^2$ are hydrogen, and the moieties $R^3$, $R^4$, $R^5$, $R^8$, $R^9$ and $R^{10}$, n, $L^1$, $L^2$, $M^1$ and $M^2$ are as defined above. Within this subset is another preferred group wherein $R^1$ is in the indole 5-position.

Also among the compounds of this invention are those of the formula:

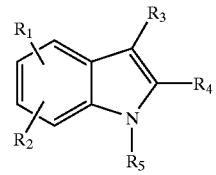

wherein:

$R_1$ is selected from —O—$C_1$-$C_6$ alkyl, —S—$C_1$-$C_6$ alkyl, —O-phenyl, —S-phenyl, —O-benzyl, —S-benzyl, the alkyl, phenyl or benzyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;

$R^2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

$R_3$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —NH2, —NH—$C_1$-$C_6$ alkyl, —N($C_1$-$C_6$ alkyl)$_2$, —N—$SO_2$—$C_1$-$C_6$ alkyl, —$SO_2$—$C_1$-$C_6$ alkyl, or a moiety of the formula:

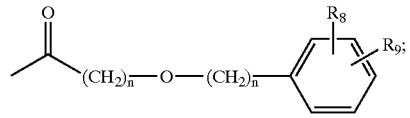

n in each appearance is independently selected as an integer selected from 0–3;
  $R^8$ and $R^9$ are independently selected in each appearance from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl, —NH($C_1$-$C_6$ alkyl), or —N($C_1$-$C_6$ alkyl)$_2$;
  $R_4$ is the moiety —$L^1$—$M^1$ or

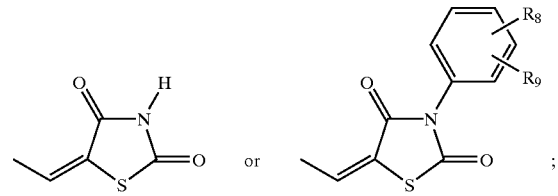

$L^1$ is selected from a chemical bond or a bridging group selected from —$(CH_2)_n$—O—, —$(CH_2)_n$—S—, —$(CH_2)_n$—O—$(CH_2)_n$—, —$(CH_2)_n$—S—$(CH_2)_n$—, —C(O)—O—, —C(O)—$(CH_2)_n$—O—, —C(O)—N—, or —$(CH_2)_n$—S—$(CH_2)_n$—C(O)—N—;

$M^1$ is the moiety:

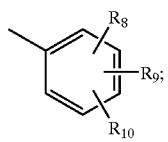

$R^{10}$ is selected from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl,

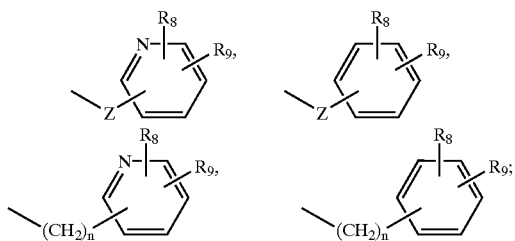

with a proviso that the combination of moieties comprising $R^4$ include a carboxylic acid or a moiety of the formulae:

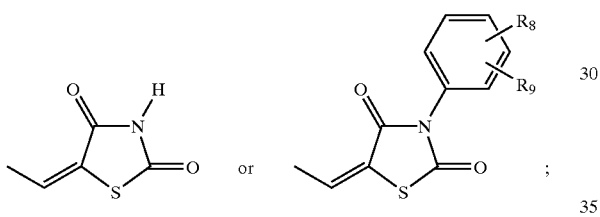

$R_5$ is a structure of the formula —$L^2$—$M^2$;
$L^2$ is selected from a chemical bond or a bridging group selected from —$(CH_2)_n$—O—, —$(CH_2)_n$—S—, —$(CH_2)_n$—O—$(CH_2)_n$—, —$(CH_2)_n$—S—$(CH_2)_n$—, —C(O)—O—, —C(O)—$(CH_2)_n$—O—, —C(O)—N—, or —$(CH_2)_n$—S—$(CH_2)_n$—C(O)—N—;
$M^2$ is selected from —$C_1$-$C_6$ alkyl, —O—$C_1$-$C_6$ alkyl,

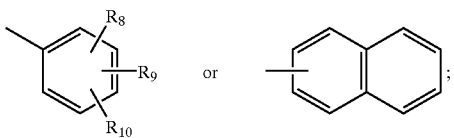

wherein $R^8$, $R^9$ and $R^{10}$ are as defined above; or a pharmaceutically acceptable salt thereof.

Also preferred are compounds of the group above with the structure:

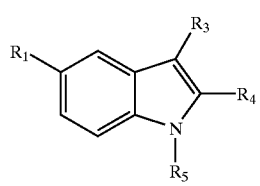

wherein
$R_1$ is selected from —O—$C_1$-$C_6$ alkyl, —S—$C_1$-$C_6$ alkyl, —O-phenyl, —O-benzyl, —S-benzyl, the alkyl, phenyl or benzyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;
$R_3$ is selected from H, halogen, —$CF_3$, —OH, —$C_1$-$C_{10}$ alkyl, preferably —$C_1$-$C_{10}$ alkyl, $C_1$-$C_{10}$ alkoxy, preferably $C_1$-$C_{10}$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, —$SO_2$—$C_1$-$C_6$ alkyl or a moiety of the formula:

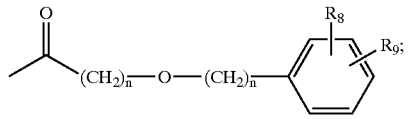

wherein $R^4$, $R^5$, $R^8$, $R^9$ and $R^{10}$ are as defined above, or a pharmaceutically acceptable salt thereof.

Also among the compounds of the present invention are those of the formulae:

Among the compounds of this invention are those of the formula:

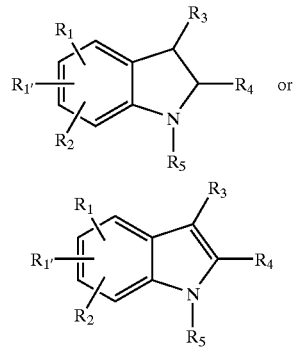

wherein $R_1$ and $R_{1'}$ are independently selected from $C_1$-$C_6$ alkyl, —Z—$C_1$-$C_6$ alkyl, phenyl, —$(CH_2)_n$—Z—$(CH_2)_n$—phenyl, benzyl, —$(CH_2)_n$—Z—$(CH_2)_n$-benzyl, napthyl, —$(CH_2)_n$—Z—$(CH_2)_n$-napthyl, pyrimidinyl, —$(CH_2)_n$—Z—$(CH_2)_n$-pyrimidinyl, the alkyl, phenyl, benzyl, napthyl and pyrimidinyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;

Z is O or S;

n is an integer from 0 to 3;

$R_2$ is selected from H, halogen, —$CF_3$, —OH, -$C_1$-$C_{10}$ alkyl, $C_1$-$C_{10}$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

$R_3$ is selected from H, halogen, —$CF_3$, —OH, $C_1$-$C_{10}$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, —$SO_2$—$C_1$-$C_6$ alkyl or:

n in each appearance is independently selected as an integer selected from 0–3;

$R_4$ is selected from —COOH, —$(CH_2)_n$—COOH, —$(CH_2)_n$—C(O)—COOH, —CH=CH—COOH, tetrazole, —$(CH_2)_n$-tetrazole, the moiety —$L^1$—$M^1$ or a moiety of the formulae:

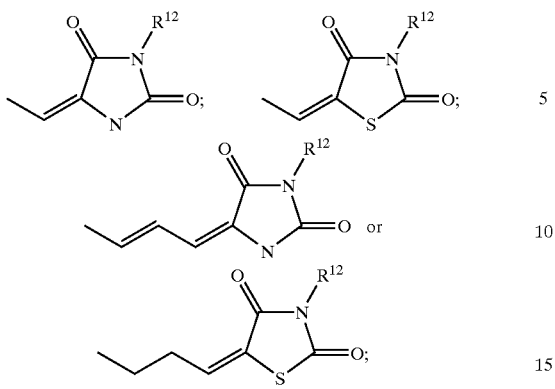

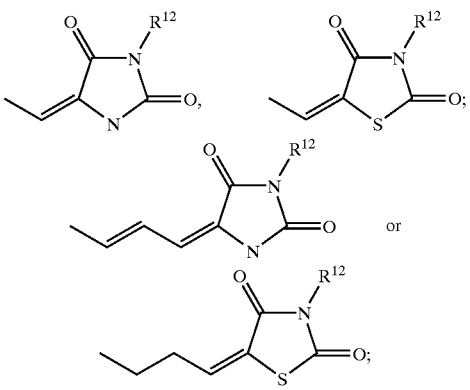

$R^{12}$ is selected from H, —$CF_3$, $C_1$-$C_6$ alkyl, —$(CH_2)_n$—$C_3$-$C_6$ cycloalkyl, phenyl, or benzyl, the cycloalkyl, phenyl or benzyl groups being optionally substituted by from 1 to 3 groups selected from halogen, —$CF_3$, —OH, —COOH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), or —N($C_1$-$C_6$ alkyl)$_2$;

$L^1$ is selected from —$(CH_2)_n$—O—, —$(CH_2)_n$—S—, —$(CH_2)_n$—O—$(CH_2)_n$—, —$(CH_2)_n$—S—$(CH_2)_n$—, —C(O)—O—, —C(O)—$(CH_2)_n$—O—, —C(O)—N—, —$(CH_2)_n$—S—$(CH_2)_n$—C(O)—N—, —$(CH_2)_n$—O—$(CH_2)_n$—C(O)—NH—, —$CH_2$—S—$CH_2$—C(O)—NH—, or —$CH_2$—$SO_2$—$CH_2$—C(O)—NH—;

$M^1$ is —COOH or a moiety selected from:

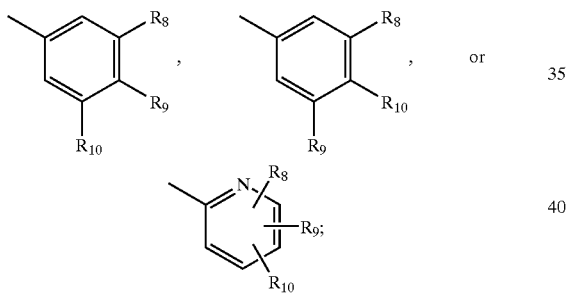

$R^8$ and $R^9$ are independently selected in each appearance from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl, —NH($C_1$-$C_6$ alkyl), or —N($C_1$-$C_6$ alkyl)$_2$;

$R_{10}$ is selected from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl,

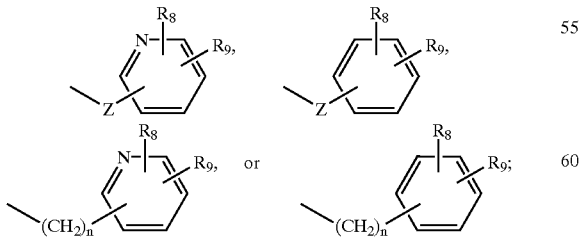

with a proviso that the moiety or combination of moieties comprising $R^3$ include an acidic group selected from carboxylic acid or a moiety of the formulae:

$R_5$ is selected from:
a) a moiety of the formula —$L^2$—$M^2$;

$L^2$ is selected from a chemical bond or a bridging group selected from —$(CH_2)_N$—Z—, —$(CH_2)_n$—Z—$(CH_2)_n$—, —C(O)—O—, —C(O)—$(CH_2)_n$—O—, —C(O)—N—, or —$(CH_2)_n$—S—$(CH_2)_n$—C(O)—N—;

$M^2$ is selected from —$C_1$-$C_6$ alkyl, —O—$C_1$-$C_6$ alkyl,

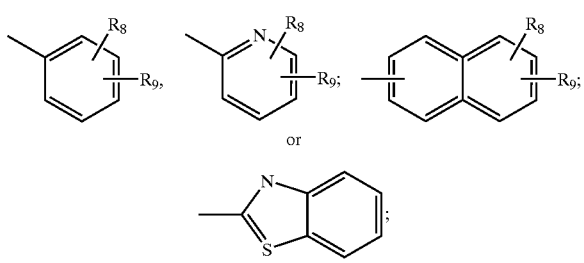

or

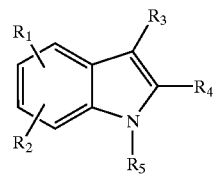

or a pharmaceutically acceptable salt thereof Of the compounds in the group just defined, a preferred subset include those in which the core molecule is an indole. Within the indole group is another subset wherein $R^{1'}$ and $R^2$ are hydrogen, and the moieties $R^3$, $R^4$, $R^5$, $R^8$, $R^9$ and $R^{10}$, n, $L^1$, $L^2$, $M^1$ and $M^2$ are as defined above. Within this subset is another preferred group wherein $R^1$ is in the indole 5-position.

Also among the compounds of this invention are those of the formula:

wherein:
$R_1$ is selected from —O—$C_1$-$C_6$ alkyl, —S—$C_1$-$C_6$ alkyl, —O—phenyl, —S-phenyl, —O-benzyl, —S-benzyl, the alkyl, phenyl or benzyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;

$R_2$ is selected from H, halogen, —$CF_3$, —OH, —$C_1$-$C_{10}$ alkyl, preferably —$C_1$-$C_6$ alkyl, $C_1$-$C_{10}$ alkoxy, preferably $C_1$-$C_6$ alkoxy, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, or —$SO_2$—$C_1$-$C_6$ alkyl;

$R_3$ is selected from H, halogen, —$CF_3$, —OH, CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, —$SO_2$—$C_1$-$C_6$ alkyl or:

n in each appearance is independently selected as an integer selected from 0–3;

$R^8$ and $R^9$ are independently selected in each appearance from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl, —NH($C_1$-$C_6$ alkyl), or —N($C_1$-$C_6$ alkyl)$_2$;

$R_4$ is the moiety —$L^1$—$M^1$ or

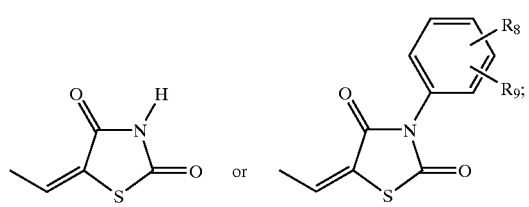

$L^1$ is selected from a chemical bond or a bridging group selected from —$(CH_2)_n$—O—, —$(CH_2)_n$—S—, —$(CH_2)_n$—O—$(CH_2)_n$—, —$(CH_2)_n$—S—$(CH_2)_n$—, —C(O)—O—, —C(O)—$(CH_2)_n$—O—, —C(O)N—, —$(CH_2)_n$—S—$(CH_2)_n$—C(O)—N—, —$(CH_2)_n$—O—$(CH_2)_n$—C(O)—NH—, —$CH_2$—S—$CH_2$—C(O)—NH—, or —$CH_2$—$SO_2$—$CH_2$—C(O)—NH—;

$M^1$ is the moiety:

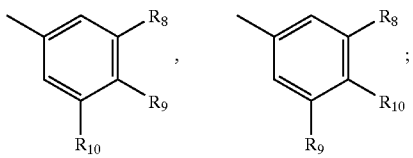

$R^{10}$ is selected from H, —COOH, —$(CH_2)_n$—COOH, —$(CH_2)_n$—C(O)—COOH, —$CF_3$, —OH, —$(CH_2)_n$—C(O)—COOH, —$C_1$-$C_6$ alkyl, —O—$C_1$-$C_6$ alkyl,

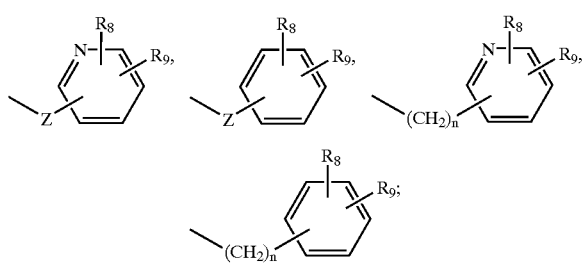

with a proviso that the combination of moieties comprising $R^4$ include a carboxylic acid or a moiety of the formulae:

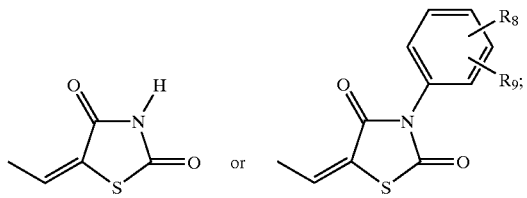

$R_5$ is a structure of the formula —$L^2$—$M^2$;
$L^2$ is selected from a chemical bond or a bridging group selected from —$(CH_2)_n$—O—, —$(CH_2)_n$—S—, —$(CH_2)_n$—O—$(CH_2)_n$—, —$(CH_2)_n$—S—$(CH_2)_n$—, —C(O)—O—, —C(O)—$(CH_2)_n$—O—, —C(O)—N—, or —$(CH_2)_n$—S—$(CH_2)_n$—C(O)—N—;
$M^2$ is selected from —$C_1$-$C_6$ alkyl, —O—$C_1$-$C_6$ alkyl,

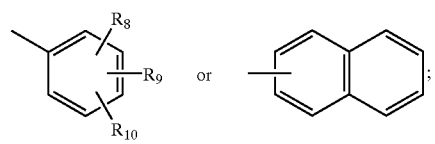

wherein $R^8$, $R^9$ and $R^{10}$ are as defined above;
or a pharmaceutically acceptable salt thereof.
Also preferred are compounds of the group above with the structure:

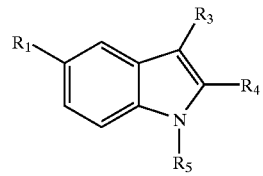

wherein
$R_1$ is selected from —O—$C_1$-$C_6$ alkyl, —S—$C_1$-$C_6$ alkyl, —O-phenyl, —O-benzyl, —S-benzyl, the alkyl, phenyl or benzyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, or —OH;
$R_3$ is selected from H, halogen, —$CF_3$, —OH, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, —$SO_2$—$C_1$-$C_6$ alkyl or:
wherein $R^4$, $R^5$, $R^8$, $R^9$ and $R^{10}$ are as defined above, or a pharmaceutically acceptable salt thereof.

The compounds of this invention inhibit Cytosolic Phospholipase A2 (cPLA2) activity which is required for supplying arachidonic acid substrate to cyclooxygenase-1 or 2 and 5-lipoxygenase, which in turn initiates the production of prostaglandins and leukotrienes, respectively. In addition, cPLA2 activity is essential for producing the lysophospholipid precursor to Platelet Activating Factor (PAF). Thus, these compounds are useful in the treatment and prevention of disease states in which leukotrienes, prostaglandins or PAF are involved. Moreover, in diseases where more than one of these agents plays a role, a cPLA2 inhibitor is more efficacious than leukotriene, prostaglandin or PAF receptor antagonists and also more effective than cyclooxygenase or 5-lipoxygenase inhibitors.

Therefore, the compounds, pharmaceutical compositions and regimens of the present invention are useful in treating and preventing the disorders treated by cyclooxygenase-2, cycloxygenase-1, and 5-lipoxygenase inhibitors or antagonists of the receptors for PAF, leukotrienes or prostaglandins. Diseases treatable by compounds, formulations and regimens of this invention include, but are not limited to, pulmonary disorders including diseases such as asthma, chronic bronchitis, and related obstructive airway diseases; allergies and allergic reactions such as allergic rhinitis, hay fever, contact dermatitis, allergic conjunctivitis, idiopathic infiltrative disorder of the lung, alveolitis, and the like; inflammation such as that associated with arthritis or inflammatory bowel diseases; skin disorders such as psoriasis, atopic eczema, acne, ultraviolet (UV) damage, burns primary and secondary immunodeficiency dermatosis, and dermatitis; cardiovascular disorders such as atherosclerosis, angina, myocardial ischaemia, hypertension, platelet aggregation, thrombosis, allergic angioedema and the like; and renal insufficiency induced by immunological or chemical.

The drugs may also be cytoprotective, preventing damage to the gastrointestinal mucosa by noxious agents. The compounds are also useful in the treatment of adult respiratory distress syndrome, endotoxin shock and ischeamia induced injury including myocardial or brain injury.

These compounds are especially useful in the treatment of arthritic disorders, including but not limited to rheumatoid arthritis, spondyloarthropathies, gouty arthritis, osteoarthritis, systemic lupus erythematosus and juvenile arthritis. The compounds of this invention are further useful in the treatment of post-operative inflammation, including that following ophthalmic surgery such as cataract surgery or refractive surgery.

The compounds of this invention can be used as an antipyretic agent and in combination with other antipyretic agents known in the art.

The compounds of this invention may be utilized in methods of treating pain, particularly the pain associated with inflammation. Specific methods include, but are not limited to, those for treating centrally mediated pain, peripherally mediated pain, musculo-skeletal pain, lumbosacral pain, structural or soft tissue injury related pain, progressive disease related pain, such as oncology and degenerative disorders, neuropathic pain, which can include both acute pain, such as acute injury or trauma, pre- and post-surgical, migraine pain, dental pain, etc., chronic pains, such as neuropathic pain conditions of diabetic peripheral neuropathy, post-herpetic neuralgia and fibromyalgia, and inflammatory conditions such as osteoarthritis or rheumatoid arthritis, sequela to acute injury or trauma and cancer-related pain.

Compositions and compounds of this invention are also useful in the treatment of menstrual cramps, preterm labor, tendonitis, bursitis, allergic neuritis, cytomegalovirus infection, apoptosis, including HIV-induced apoptosis, lumbago, liver disease including hepatitis.

The methods and compositions herein are also useful in treating gastrointestinal conditions such as inflammatory bowel disease, Crohn's disease, gastritis, irritable bowel syndrome and ulcerative colitis and for the prevention of treatment of cancer such as colorectal cancer. The compounds and compositions of the present invention are also useful for the prevention or treatment of benign and malignant tumors/neoplasia including cancers such as colorectal cancer, brain cancer, bone cancer, epithelial cell-derived neoplasia (epithelial carcinoma) such as basal cell carcinoma, adenocarcinoma, gastrointestinal cancer, including lip cancer, mouth cancer, esophogeal cancer, small bowel cancer and stomach cancer, colon cancer, liver cancer, bladder cancer, pancreatic cancer, ovarian cancer, cervical cancer, lung cancer, breast cancer, and skin cancers, such as squamous cell and basal cell cancers, prostate cancer, renal cell carcinoma, and other known cancers that effect epithelial cells throughout the body. Neoplasias for which compositions of the invention are particularly useful are gastrointestinal cancer, Barrett's esophagus, liver cancer, bladder cancer, pancreas cancer, ovarian cancer, prostatic cancer, cervical cancer, lung cancer, breast cancer, and skin cancer, such as squamous cell and basal cell cancers. The compounds and methods of this invention can also be used to treat the fibrosis occuring with radiation therapy. Such compositions can be used to treat subjects having adenomatous polyps, including those with familial adenomatous polyposis (FAP). Additionally, such compositions can be used to prevent polyps from forming in patients at risk of FAP. Compounds of this invention will be useful in the treatment of cancers based on anti-angiogenic effects.

Further uses of this invention include treating inflammation in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like. Also included are treatment of ophthalmic diseases, such as retinitis, conjunctivitis, retinopathies, uveitis, ocular photophobia, and of acute injury to the eye tissue. Treatments herein of pulmonary inflammation, such as that associated with viral infections and cystic fibrosis, and in bone resorption such as that accompanying osteoporosis. These compounds and compositions are useful for the treatment of certain central nervous system disorders, such as cortical dementias including Alzheimer's disease, neurodegeneration, and central nervous system damage resulting from stroke, ischemia and trauma. The compounds of this invention may also be useful in the treatment of Parkinson's disease.

It will be understood that methods of treating or preventing the maladies listed herein comprise administering to a mammal subject to or experiencing the malady, which may also be referred to as a mammal in need thereof, a pharmaceutically effective amount of a compound of this invention, or a pharmaceutically acceptable salt thereof.

Methods of treating pain comprise administering to a mammal subject to such pain a pharmaceutically effective amount of a compound of this invention alone or in combination with one or more additional pharmaceutically effective agents for the treatment of pain or inflammation or the related underlying medical condition. Examples of drug agents which may be combined with the present compounds are analgesics, anti-angiogenic agents, anti-neoplastic agents, These compounds may also be combined with anti-epileptic compounds that have pain alleviating properties, such as gabapentin and pregabalin.

One such combination method of this invention comprises administering to a mammal in need thereof a pharmaceutically effective amount of a compound of this invention and a pharmaceutically effective amount of a nontoxic N-methyl-D-aspartate (NMDA) receptor antagonist and/or an agent that blocks at least one major intracellular consequence of NMDA receptor activation. Examples of NMDA receptor antagonists useful in these methods include dextromethorphan, dextrorphan, amantadine and memantine, or the pharmaceutically acceptable salts thereof.

Another method herein of treating inflammation and inflammatory disorders comprises the co-administration to a mammal in need thereof of an inhibitor of induced nitric oxide synthase with a compound of this invention. Administration of this combination is useful for prophylactic or therapeutic administration in a mammal experiencing or subject to an abnormally low level of nitric oxide synbthase (NOS) activity, particularly those subject to hypertension or an elevated risk of pulmonary hypertension, ischemic stroke, myocardial infarction, heart failure, progressive renal disease, thrombosis, reperfusion injury, or a nervous system degenerative disorder, such as Alzheimer's disease, or those chronically exposed to hypoxic conditions.

The methods of this invention also include those for treating or preventing a neoplasia disorder in a mammal, including a human, in need of such treatment or prevention. The method comprises treating the mammal with a therapeutically effective amount of a compound of this invention in combination with an MMP inhibitor. These two components may further be optionally combined with one or more agents selected from an antiangiogenesis agent, an antineoplastic agent, an adjunctive agent, an immunotherapeutic agent, an analgesic agent; and/or a radiotherapeutic agent. One such multiple component therapy comprises administering to the mammal in need thereof a compound of this invention, a matrix metalloproteinase inhibitor and an antineoplastic agent.

The methods and combinations of this invention may be used for the treatment or prevention of neoplasia disorders including acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial. squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Antineoplastic agents useful in the combination therapies herein include anastrozole, calcium carbonate, capecitabine, carboplatin, cisplatin, Cell Pathways CP-461, docetaxel, doxorubicin, etoposide, fluorouracil, fluoxymestrine, gemcitabine, goserelin, irinotecan, ketoconazole, letrozol, leucovorin, levamisole, megestrol, mitoxantrone, paclitaxel, raloxifene, retinoic acid, tamoxifen, thiotepa, topotecan, toremifene, vinorelbine, vinblastine, vincristine, selenium (selenomethionine), ursodeoxycholic acid, sulindac sulfone, exemestane and eflornithine (DFMO), 1-[4-(2-Azepan-1yl-ethoxy)-benzyl]-2-(4-hydroxy-phenyl)-3-methyl-1H-indol-5-ol (TSE-424) and 2-(4-Hydroxy-phenyl)-3-methyl-1-(4-(2-piperidin-1-yl-ethoxy)-benzyl]-1H-indol-5-ol (ERA-923).

This invention also includes methods of utilizing the compounds herein in combination with a proteinaceous interleukin-1or TNF inhibitor, such as an IL-1 receptor antagonist (IL-1ra), for preventing or treating inflammatory diseases in a mammal. Acute and chronic interleukin-1 (IL-1)-mediated inflammatory diseases of interest in these methods include, but is not limited to acute pancreatitis; ALS; Alzheimer's disease; cachexia/anorexia; asthma; atherosclerosis; chronic fatigue syndrome, fever; diabetes (e.g., insulin diabetes); glomerulonephritis; graft versus host rejection; hemohorragic shock; hyperalgesia, inflammatory bowel disease; inflammatory conditions of a joint, including osteoarthrit is, psoriatic arthritis and rheumatoid arthritis; ischemic injury, including cerebral ischemia (e.g., brain injury as a result of trauma, epilepsy, hemorrhage or stroke, each of which may lead to neurodegeneration); lung diseases (e.g., ARDS); multiple myeloma; multiple sclerosis; myelogenous (e.g., AML and CML) and other leukemias; myopathies (e.g., muscle protein metabolism, esp. in sepsis); osteoporosis; Parkinson's disease; pain; pre-term labor; psoriasis; reperfusion injury; septic shock; side effects from radiation therapy, temporal mandibular joint disease, tumor metastasis; or an inflammatory condition resulting from strain, sprain, cartilage damage, trauma, orthopedic surgery, infection or other disease processes.

This invention also provides a method of administering one or more of the compounds of this invention to a female in need thereof to substantially prevent or reducing changes in the female's reproductive system associated with onset or continuation of labor. Also provided is a method of substantially preventing or reducing uterine contractility either occurring during pregnancy or associated with menorrhagia. These methods may optionally include coadministration of a compound of this invention with a progestogen, a progestin or a progestational agent.

A pharmaceutically effective amount of a compound herein will be understood to be an amount which will inhibit, prevent or alleviate the physiological origin or symptoms of the malady or condition in question. The amount will be determined by a medical professional based upon the malady or condition in question and the personal characteristics of the recipient including, but not limited to, the recipient's age, sex, weight, and medical history.

The present invention also provides for a method of inhibiting the phospholipase enzyme activity of an enzyme, comprising administering to a mammalian subject a therapeutically effective amount of a compound of the present invention. Methods of treating an inflammatory response or condition, comprising administering to a mammalian subject a therapeutically effective amount of a compound of the present invention are also provided. Pharmaceutical compositions comprising compounds of the present invention and a pharmaceutically acceptable carrier are also provided.

Pharmaceutically acceptable salts of the compounds of the compounds described herein are also part of the present invention and may be used in practicing the compounds and methods disclosed herein.

DETAILED DESCRIPTION OF THE PREFERRED EMBODIMENTS

Figure 1:
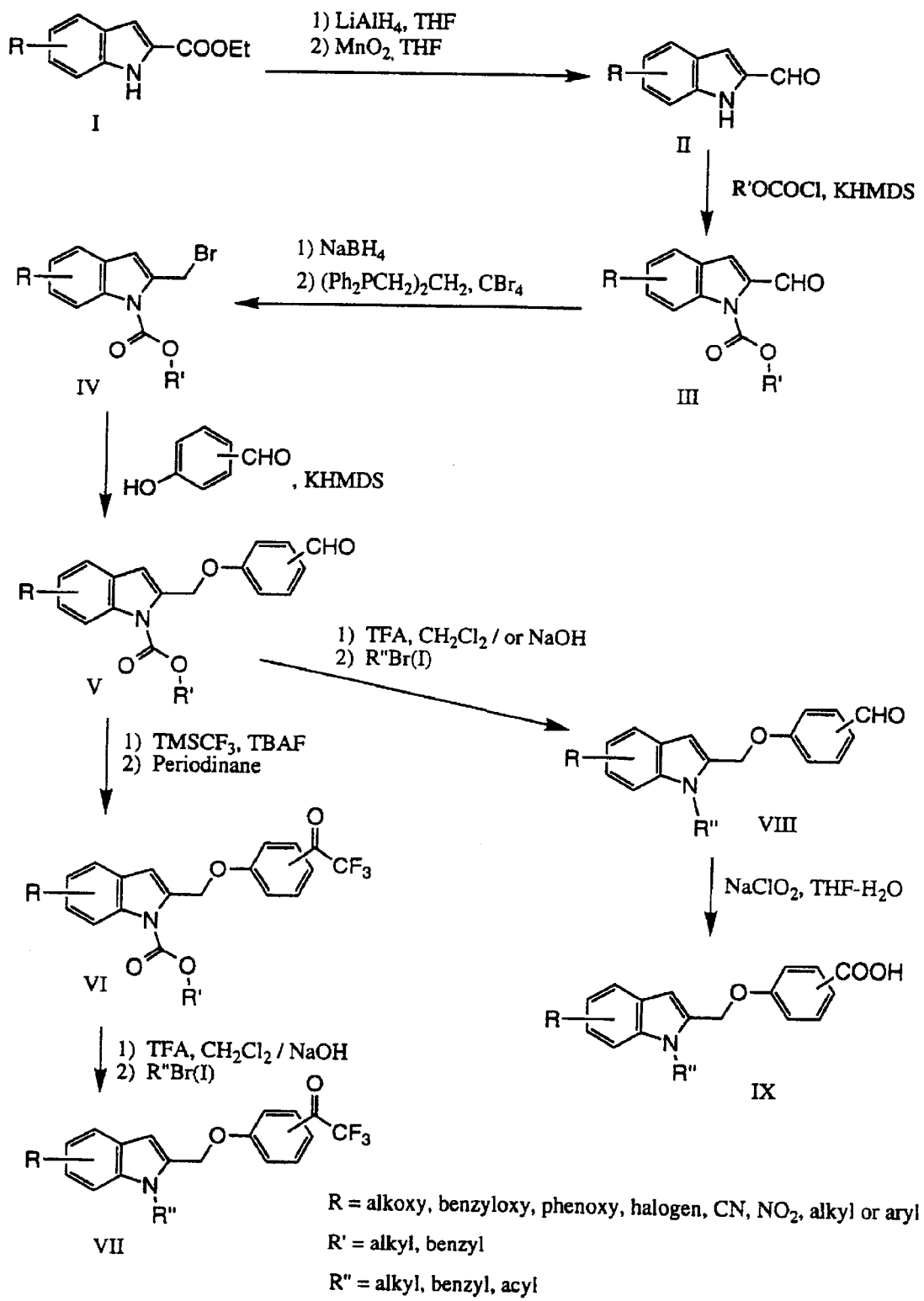
FIGS. 1–13 depict schemes for synthesis of compounds of the present invention. The depicted schemes are described in further detail below.
Figure 2:
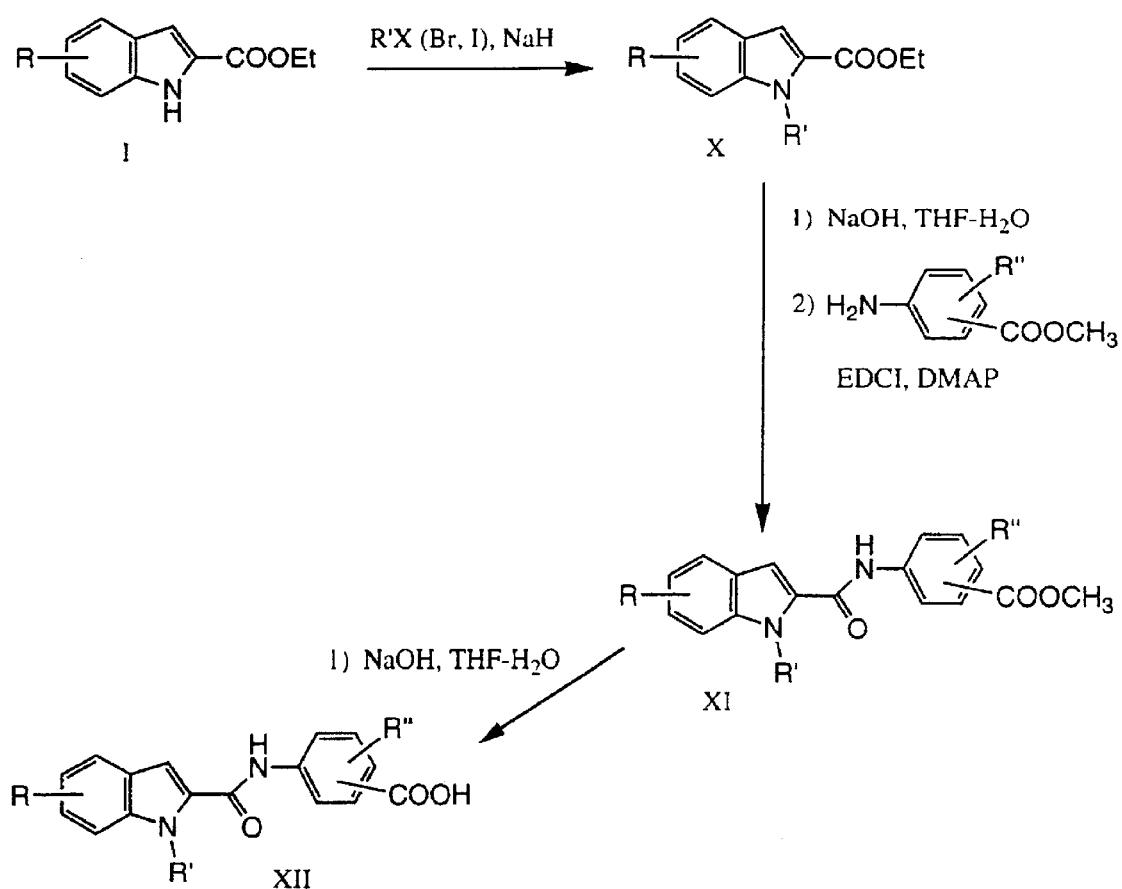
Figure 3:
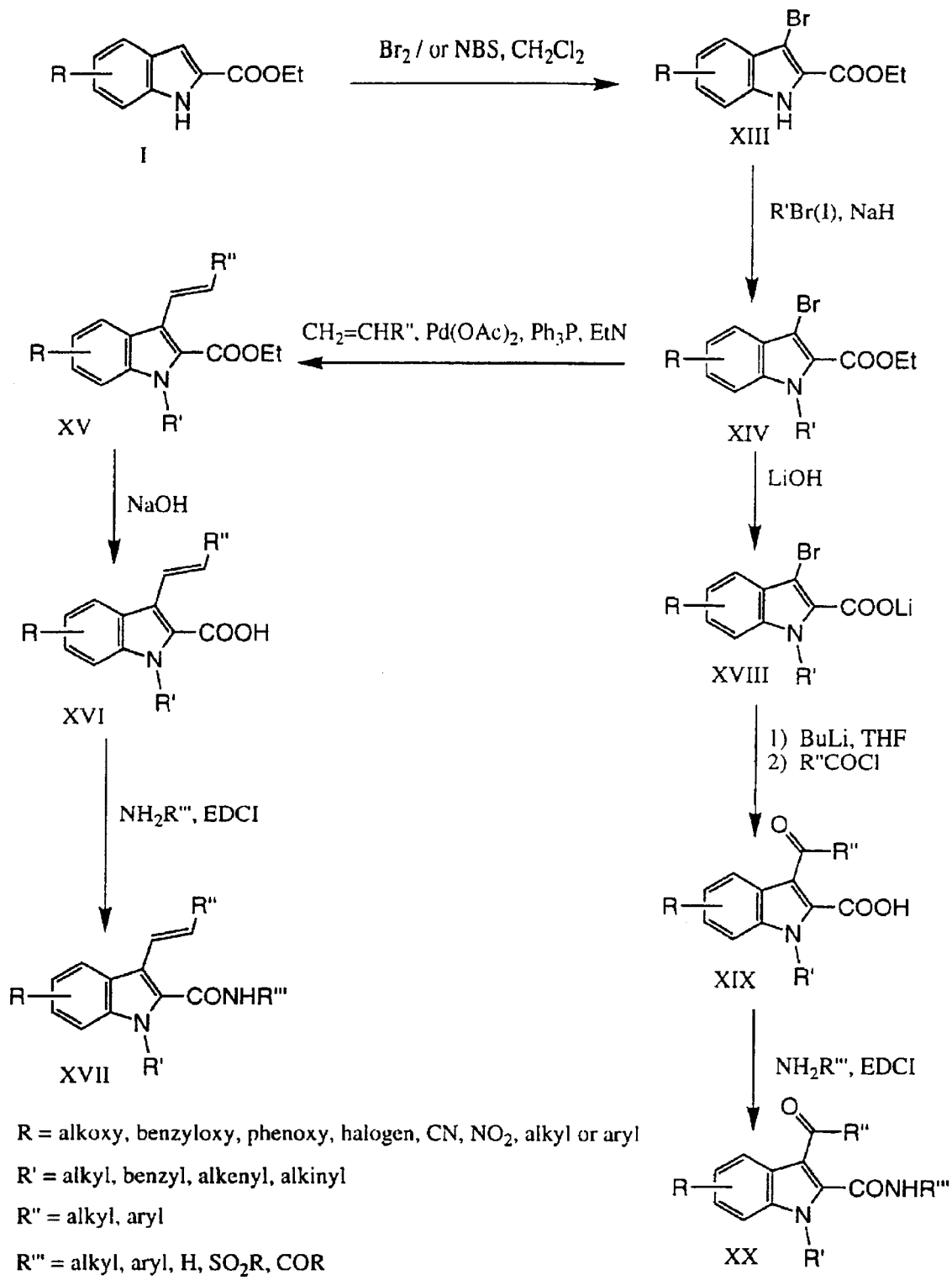
Figure 4:
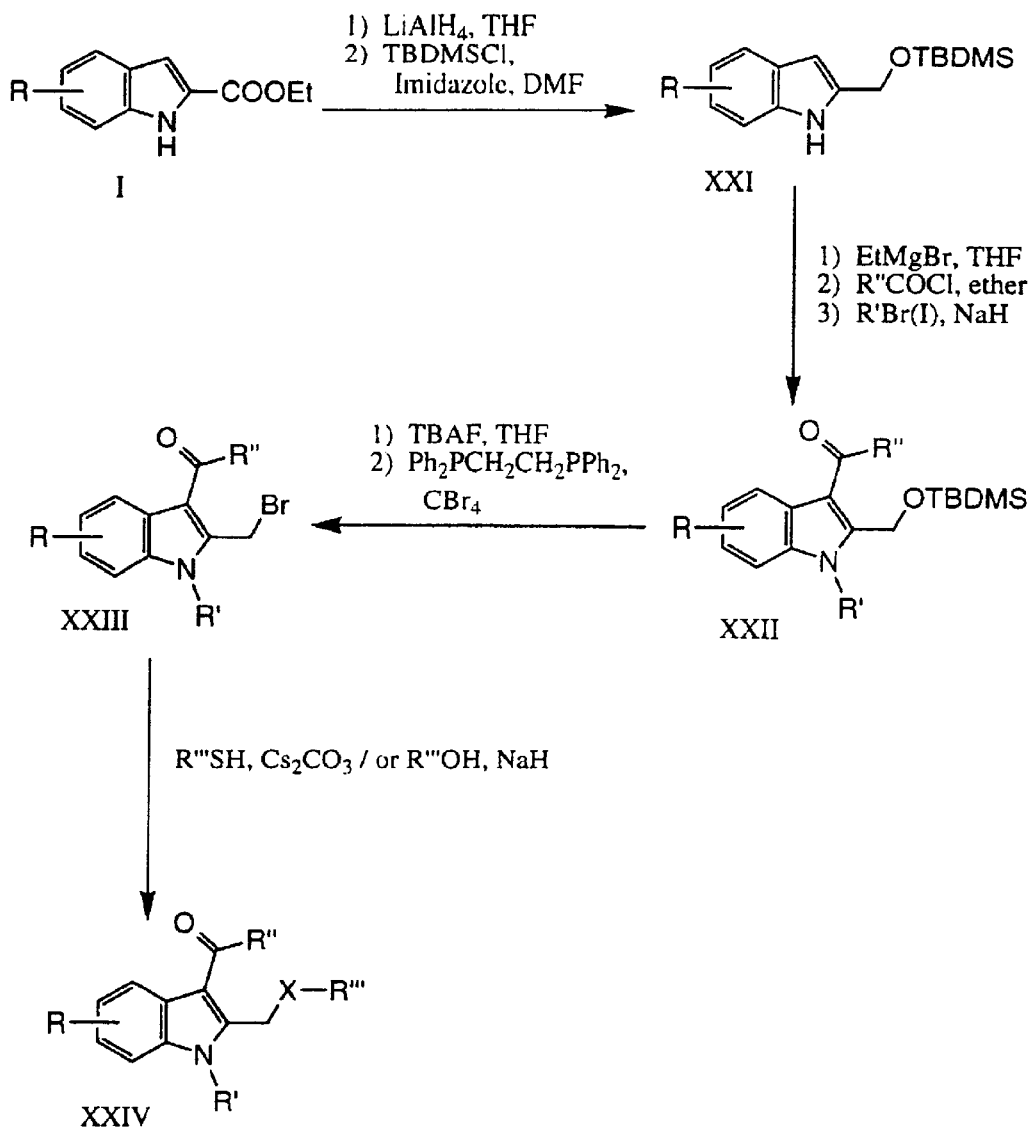
Figure 5:
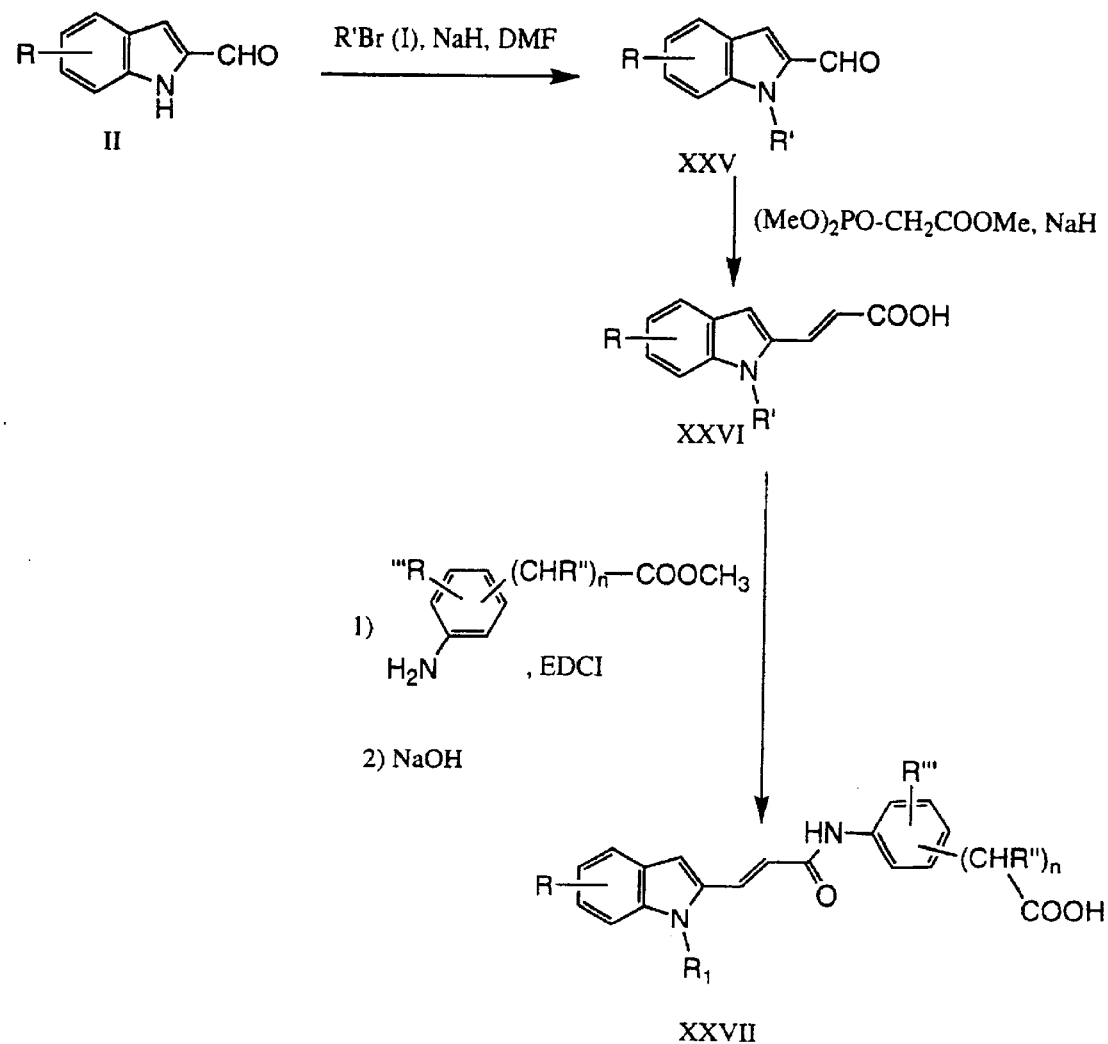
Figure 6:
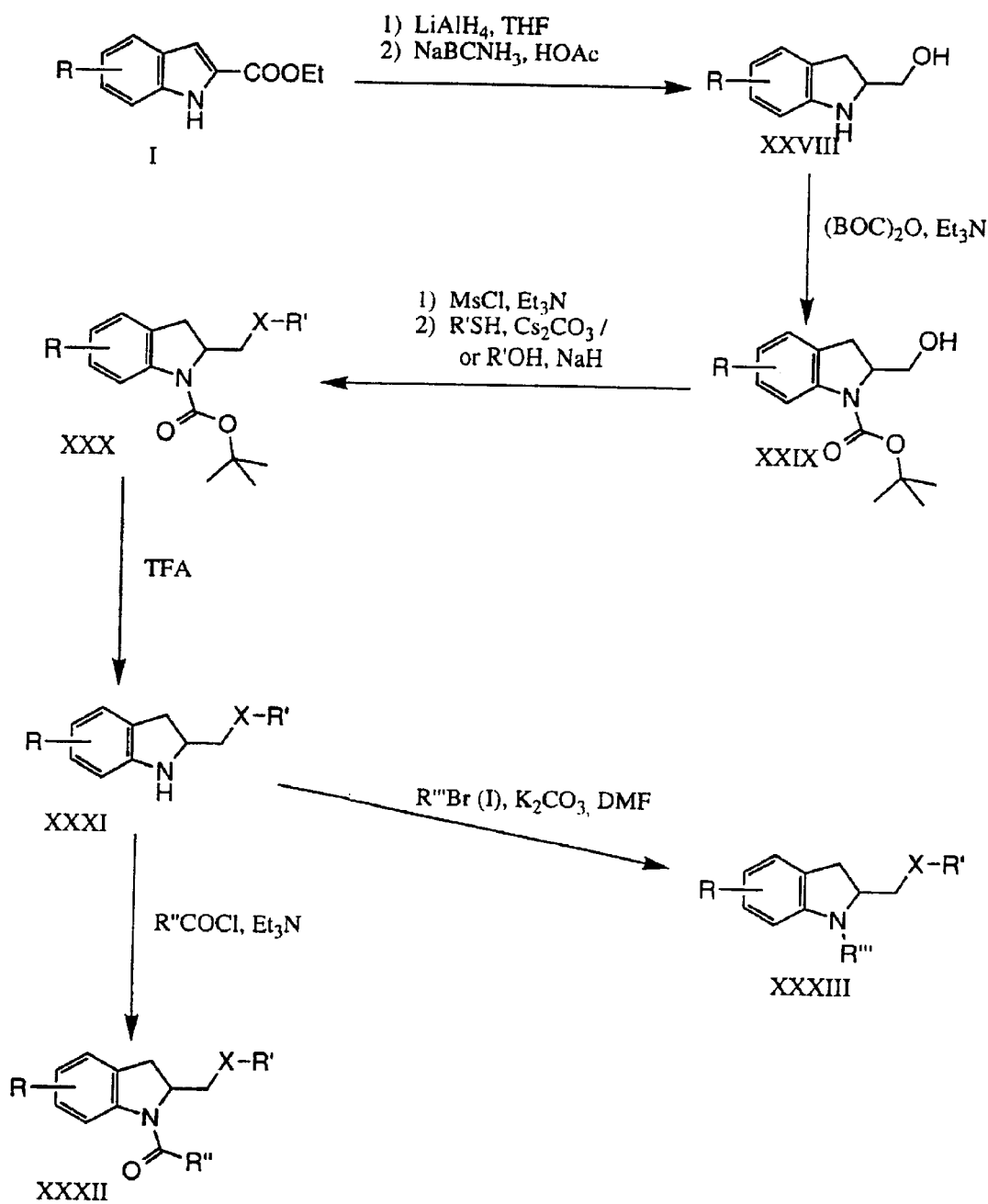
Figure 7:
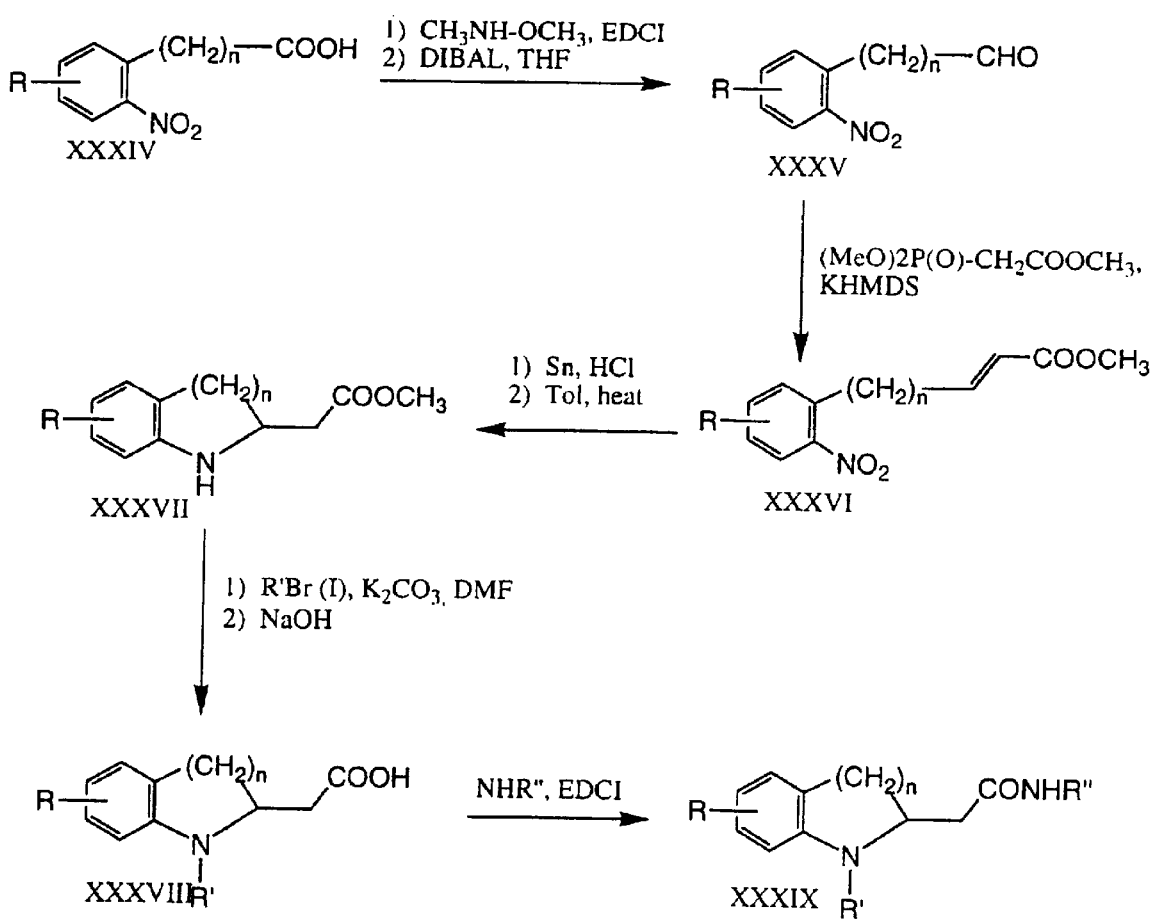
Figure 8:
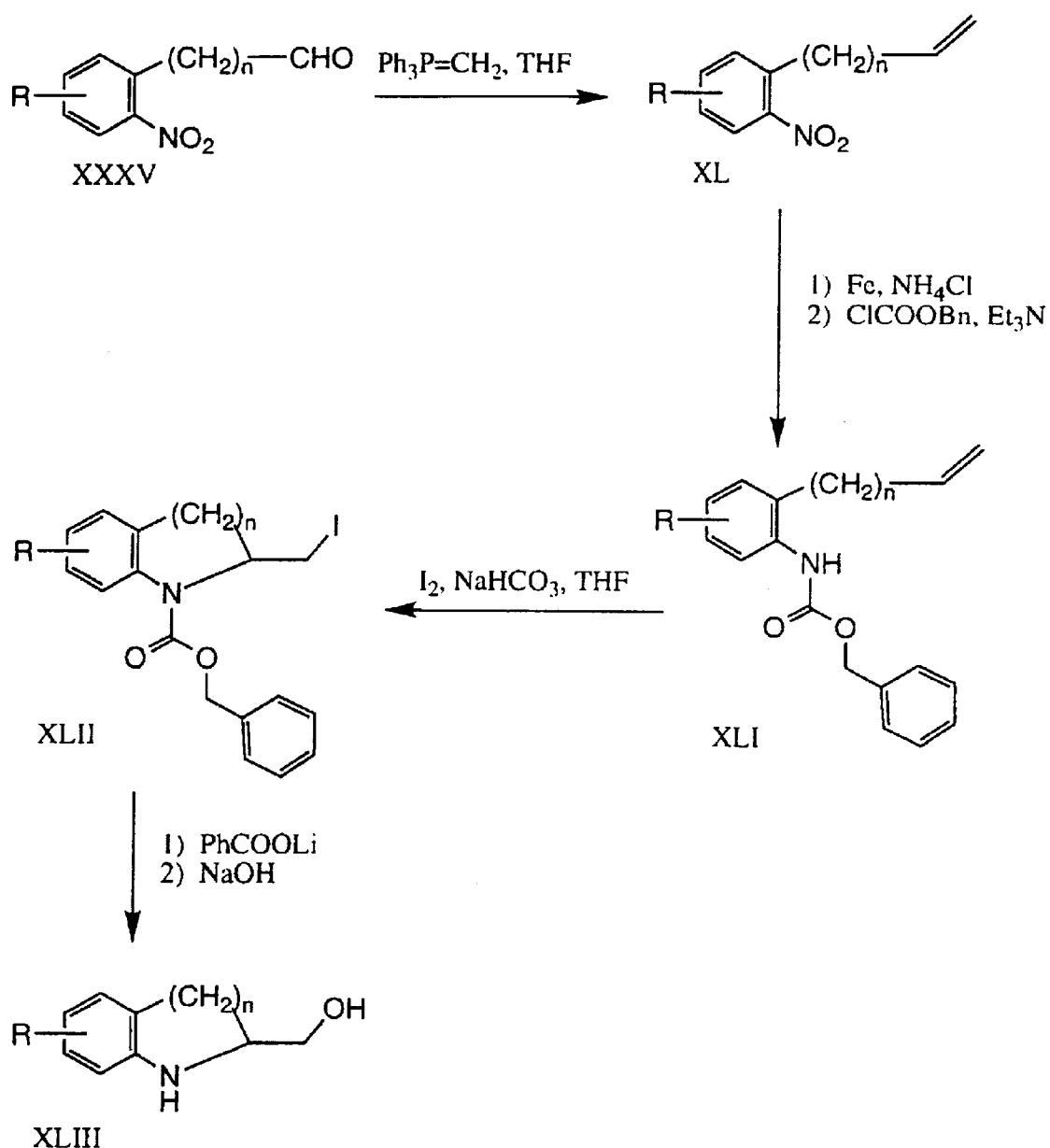
Figure 9:
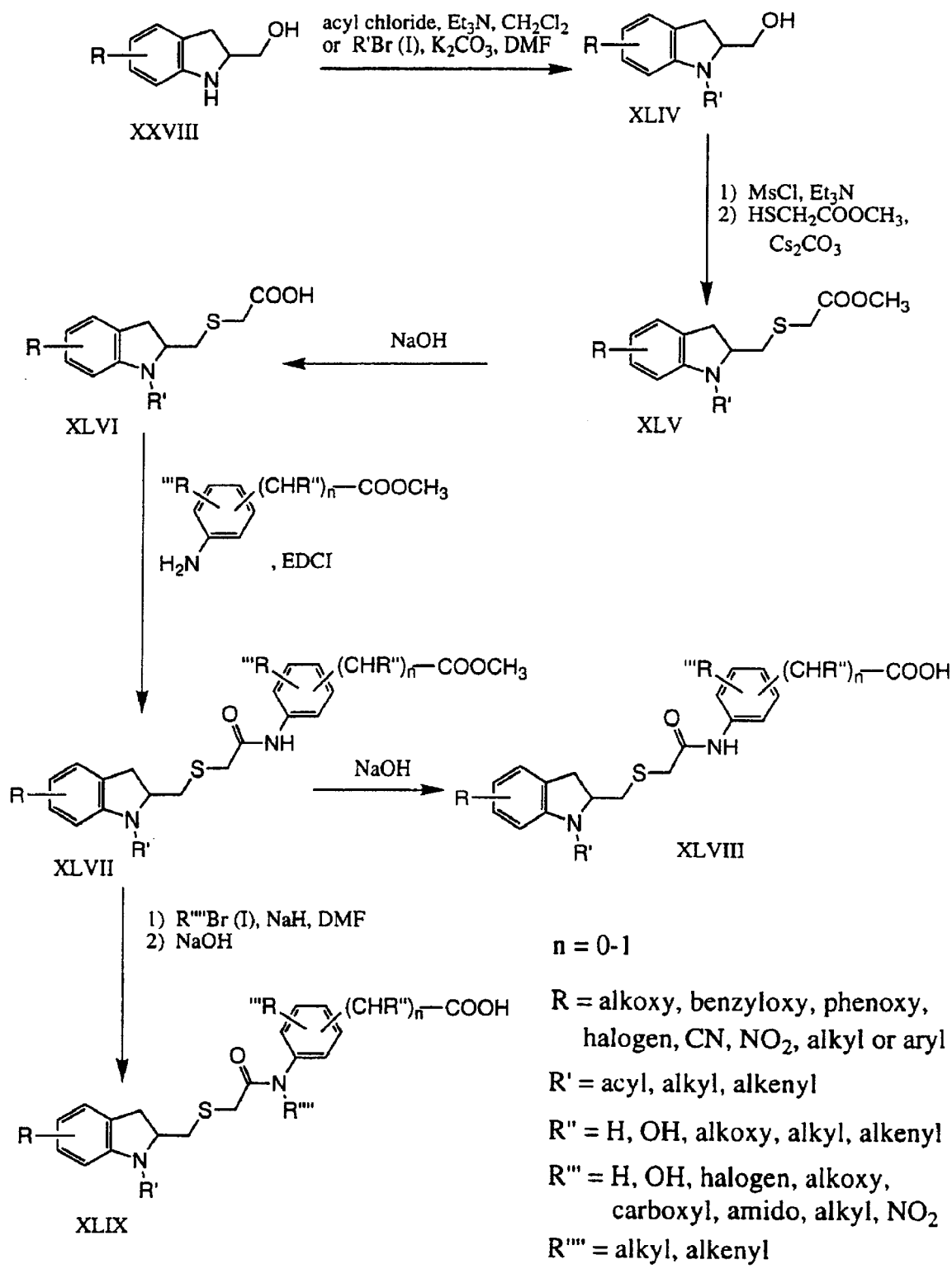
Figure 10:
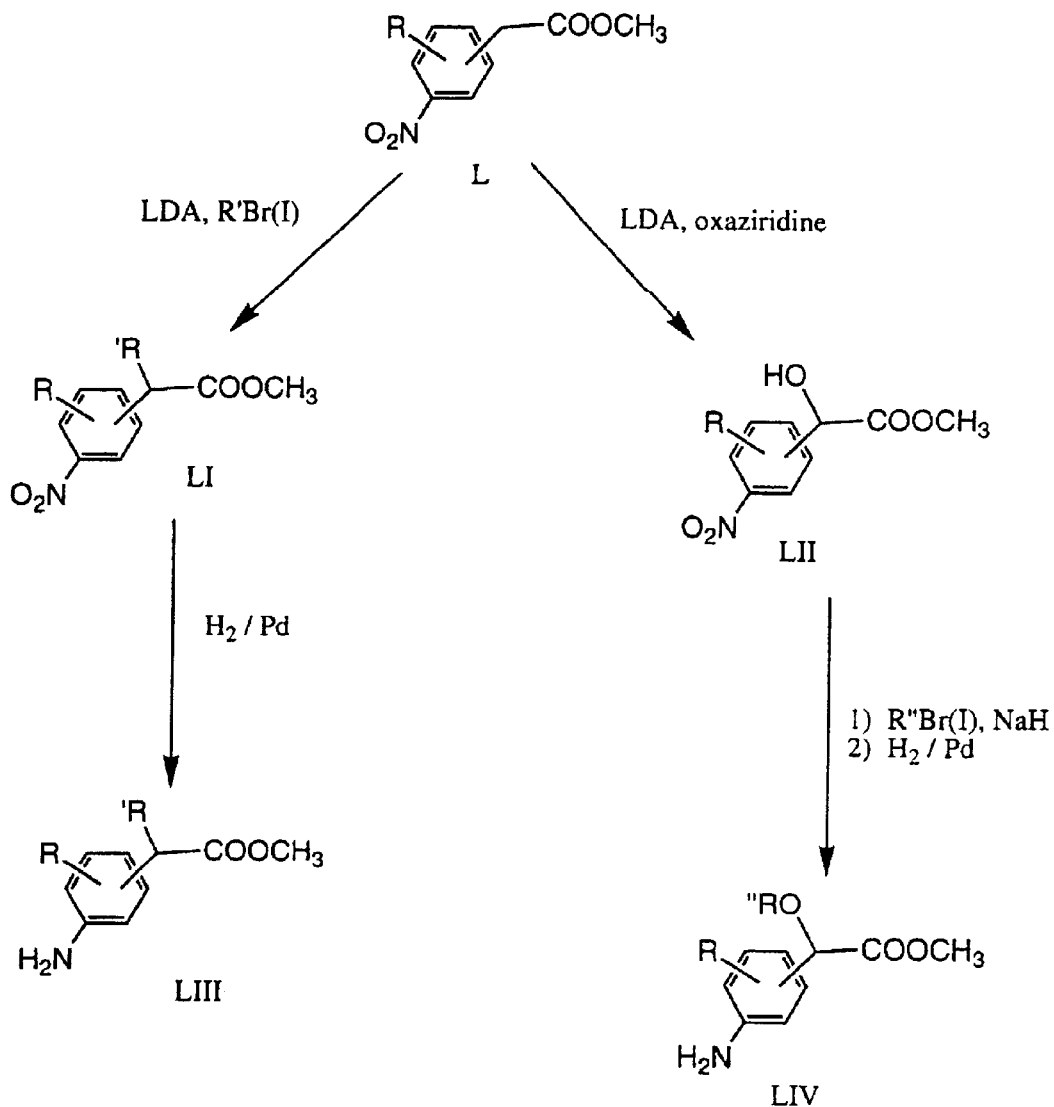
Figure 11:
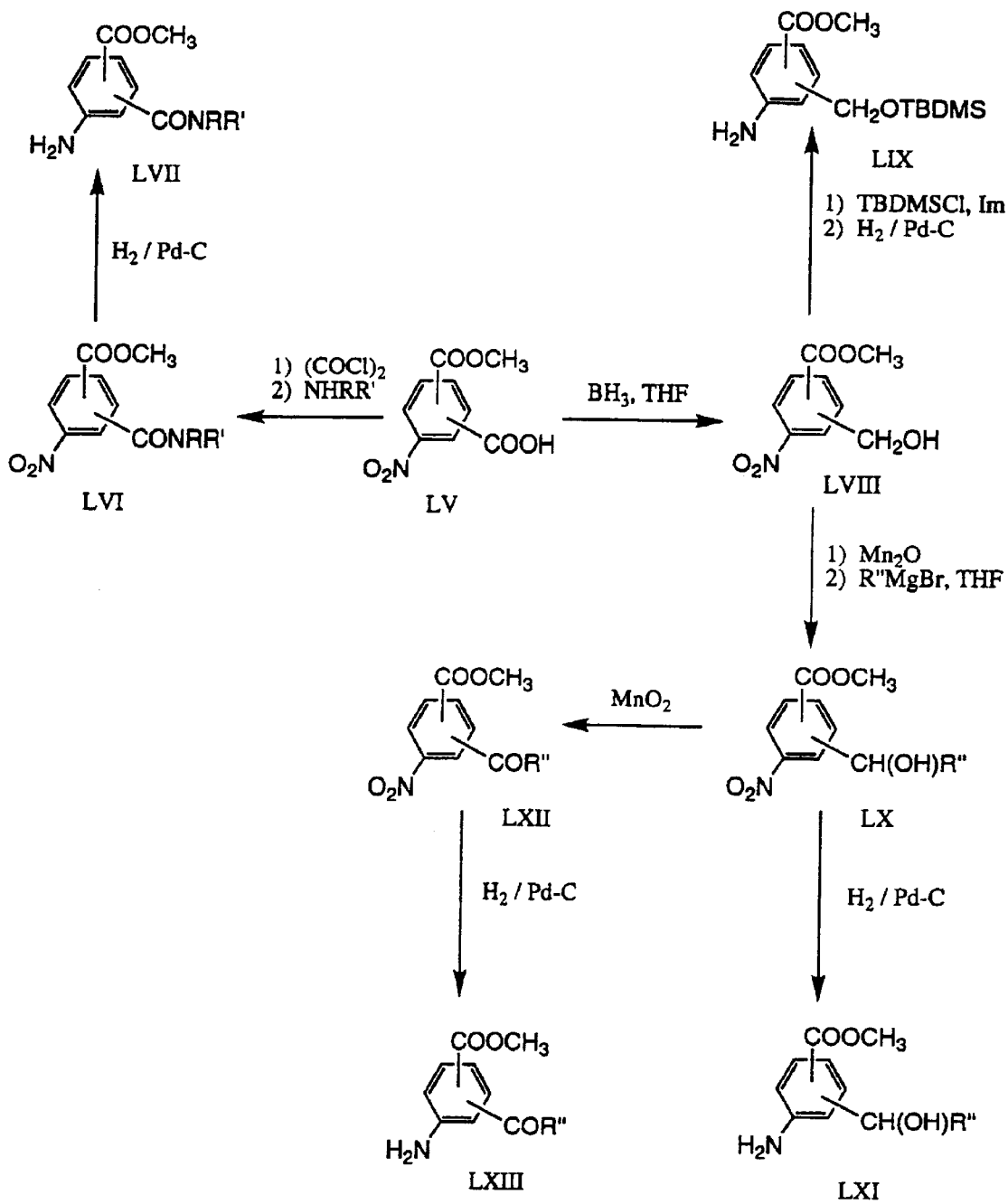
Figure 12:
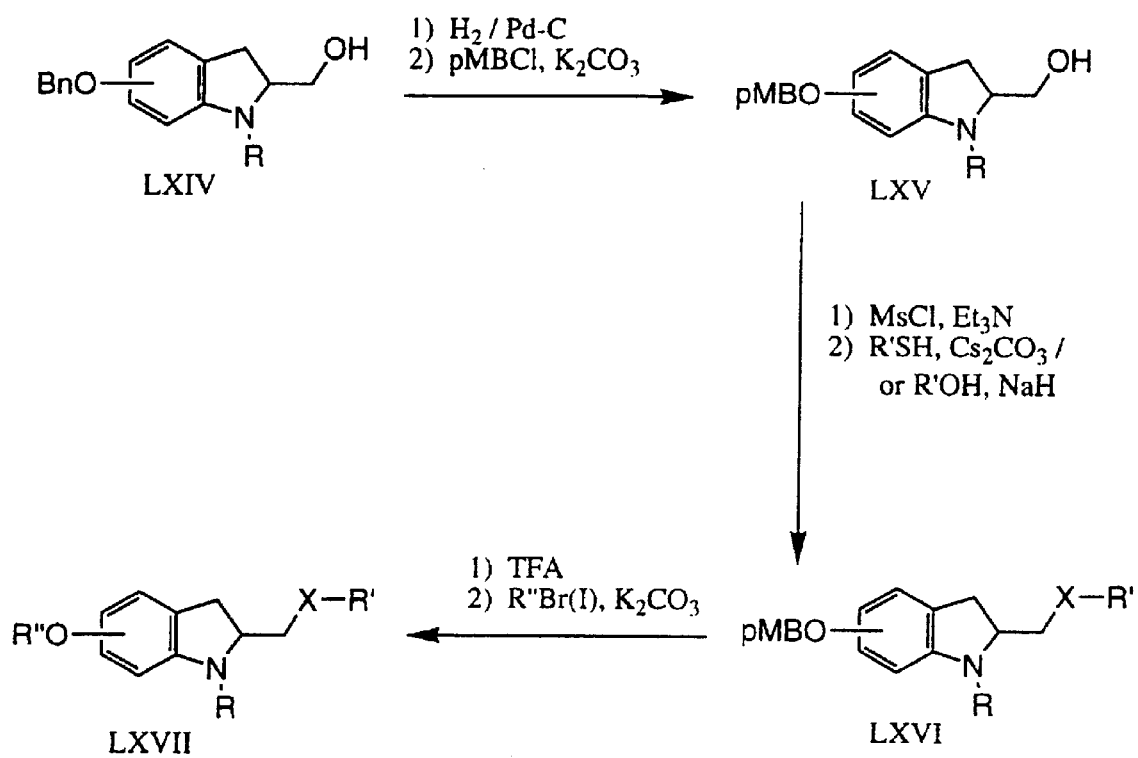
Figure 13:
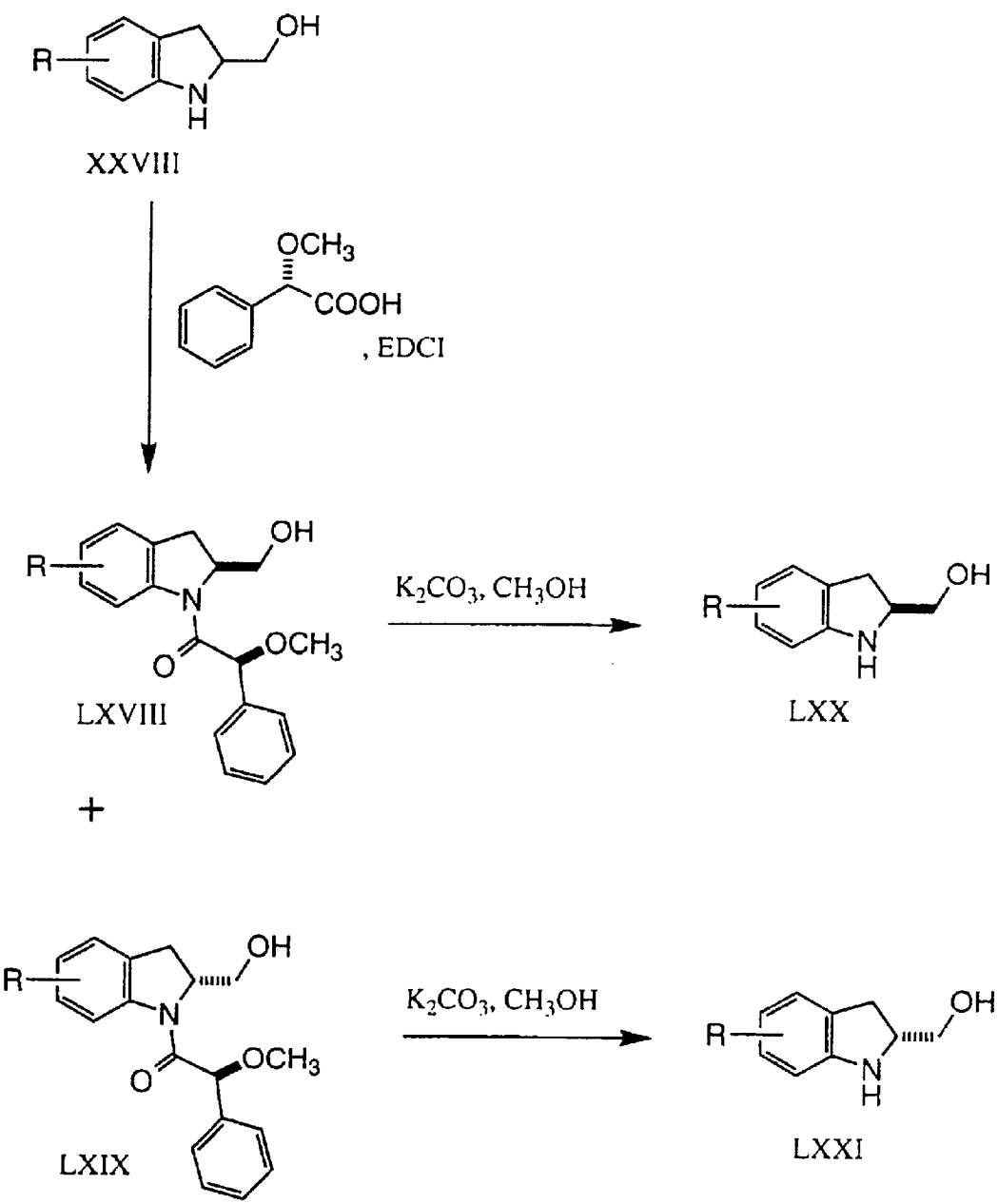

As used herein, the terms "aryl" and "substituted aryl" are understood to include monocyclic, particularly including five- and six-membered monocyclic, aromatic and heteroaromatic ring moieties and bicyclic aromatic and heteroaromatic ring moieties, particularly including those having from 9 to 10 ring atoms. Among these aryl groups are understood to be phenyl rings, including those found in phenoxy, benzyl, benzyloxy, biphenyl and other such moieties. The aryl and heteroaryl groups of this invention also include the following:

a) a five-membered heterocyclic ring containing one or two ring heteroatoms selected from N, S or O including, but not limited to, furan, pyrrole, thiophene, imidazole, pyrazole, isothiazole, isoxazole, pyrrolidine, pyrroline, imidazolidine, pyrazolidine, pyrazole, pyrazoline, imidazole, tetrazole, or oxathiazole; or b) a six-membered heterocyclic ring containing one, two or three ring heteroatoms selected from N, S or O including, but not limited to, pyran, pyridine, pyrazine, pyrimidine, pyridazine, piperidine, piperazine, tetrazine, thiazine, thiadizine, oxazine, or morpholine; or c) a bicyclic ring moiety optionally containing from 1 to 3 ring heteroatoms selected from N, S or O including, but not limited to benzofuran, chromene, indole, isoindole, indoline, isoindoline, napthalene, purine, indolizine, indazole, quinoline, isoquinoline, quinolizine, quinazoline, cinnoline, phthalazine, or napthyridine.

The "substituted aryl" groups of this invention include such moieties being optionally substituted by from 1 to 3 substituents selected from halogen, C1–C10 alkyl, preferably C1–C6 alkyl, C1–C10 alkoxy, preferably C1–C6 alkoxy, —CHO, —COOH or esters thereof, —NO2, —NH2, —CN, —CF3 or —OH or combinations thereof, such as —CH2CF3, —NH(CH3), etc.

A preferred subset of these groups, optionally substituted as just described, include moieties formed from benzene, pyridine, napthylene or quinoline rings. A further preferred group includes those of furan, pyrrole, thiophene, pyrimidine, and morpholine rings. A preferred group of bicyclic aromatic groups includes benzofuran, indole, napthalene, and quinoline rings.

The alkyl, alkenyl and alkinyl groups referred to herein indicate such groups having from 1 to 10, preferably 1 to 6 carbon atoms, and may be straight, branched or cyclic. Unless indicated otherwise, it is preferred that these groups be straight or branched. Halogens herein are understood to include F, Cl, Br and I.

Preferred compounds of the present invention are disclosed in Tables I–VI below. Methods for synthesis of the compounds listed in Tables I–VI are described below. Compound Nos. in the tables correspond to example numbers below describing synthesis of that particular compound.

Tables I–VI also report data for the listed compounds in the "LysoPC" assay and the Coumarine assay (see Example 88 below). In the data columns of the tables, assay results are reported as an "$IC_{50}$" value, which is the concentration of a compound which inhibits 50% of the activity of the phospholipase enzyme in such assay. Where no numerical $IC_{50}$ value appears, "NA" denotes that inhibitory activity was not detected from such compound in the corresponding assay and a blank box denotes that the compound was not tested in such assay as of the time of filing of the present application.

TABLE 1

| No. | R1 | R2 | R3 | R4 | IC$_{50}$ ($\mu$M) Lyso PC | IC$_{50}$ ($\mu$M) Coumarine |
|---|---|---|---|---|---|---|
| 1 | —O—CH$_2$—C$_6$H$_5$ | —C(O)O—CH$_2$—C$_6$H$_5$ | —H | —CH$_2$O—(2-COOH-C$_6$H$_4$) | 47 | |
| 2 | | | —H | —CH$_2$O—(4-COOH-C$_6$H$_4$) | 6 | |
| 3 | | | —H | —CH$_2$O—(3-COOH-C$_6$H$_4$) | 6.5 | 14 |
| 4 | | | —H | —CH$_2$O—(2-COCF$_3$-C$_6$H$_4$) | NA | |
| 5 | | —CH$_2$—C$_6$H$_5$ | —H | 3-(NHC(O)CH$_3$)-, 1-COOH-C$_6$H$_4$ | 4.3 | 52 |

TABLE 1-continued

| No. | R₁ | R₂ | R₃ | R₄ | IC₅₀ (μM) Lyso PC | IC₅₀ (μM) Cou-marine |
|---|---|---|---|---|---|---|
| 6 | | 2,4-di-tert-amyl-6-pentylphenyl | | 4-methoxy-3-(acylamino)benzoic acid (COOH) | 2.0 | 6 |
| 7 | | naphthalen-2-ylmethyl | | 3,5-bis(COOH)-phenyl acylamino | 2.1 | 15 |
| 8 | | | | 3-(COOH)-phenyl acylamino | 0.11 | 3.8 |
| 9 | | 4-((3,5-bis(trifluoromethyl)phenoxy)methyl)phenyl-CH₂ | | 3,5-bis(COOH)-phenyl acylamino | 0.081 | 6.5 |

TABLE 1-continued

| No. | R$_1$ | R$_2$ | R$_3$ | R$_4$ | IC$_{50}$ ($\mu$M) Lyso PC | IC$_{50}$ ($\mu$M) Coumarine |
|---|---|---|---|---|---|---|
| 10 | | 2,4-bis(CF$_3$)-benzyl | | 3-COOH-4-(6-chloropyridin-3-yloxy)phenyl-NHC(O)CH$_2$– | 0.33 | 28 |
| 11 | | | | 5-CF$_3$-2-(pyridin-2-ylthio)phenyl-NHC(O)CH$_2$– | | 33 |
| 12 | CH$_3$O– | –CH$_3$ | | 5-COOH-2-CH$_3$O-phenyl-NHC(O)CH$_2$-S-CH$_2$-C(O)CH$_2$-O-(2,4-di-tert-pentylphenyl) | 4 | 10 |

TABLE 1-continued
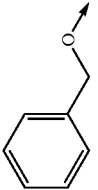
| No. | R₁ | R₂ | R₃ | R₄ | IC₅₀ (μM) Lyso PC | IC₅₀ (μM) Coumarine |
|-----|----|----|----|----|-------------------|---------------------|
| 13  |  | —CH₂CH₃ | | | 0.5 | 12 |
| 14  | | 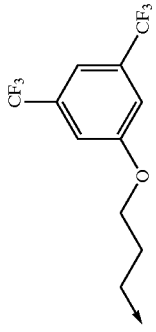 | —COCH₃ | | 1.9 | 14 |
| 15  | | 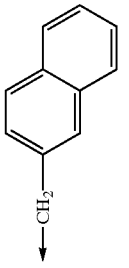 | | | 6.5 | 13 |
| 16  | | | | 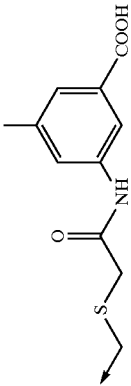 | 6.5 | 50 |

TABLE II
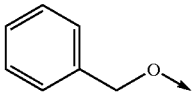
| No. | R₁ | R₂ | IC$_{50}$ ($\mu$M) Lyso PC | IC$_{50}$ ($\mu$M) Coumarine |
|---|---|---|---|---|
| 17 | 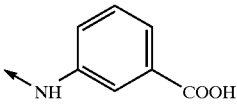 | 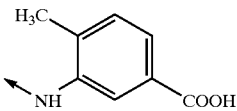 | 0.32 | 6 |
| 18 | | 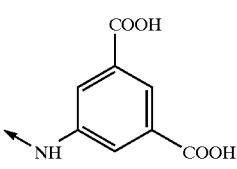 | 0.28 | 10 |
| 19 | | 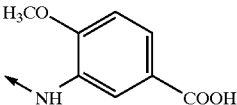 | 0.21 | 4 |
| 20 | | 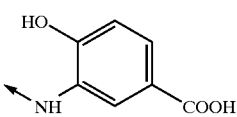 | 0.28 | 9 |
| 21 | | 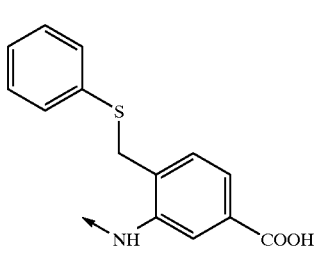 | 0.29 | 4.5 |
| 22 | | 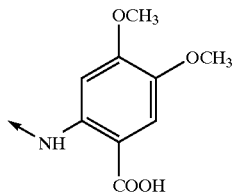 | 0.10 | 5 |
| 23 | |  | 0.95 | 5 |

TABLE II-continued

[Structure: 5-R₁-indoline with N-carboxylate linked via CH₂ to 2,4-di-tert-pentylphenyl group, and 2-CH₂-S-CH₂-C(=O)-R₂ substituent]

| No. | R₁ | R₂ | IC₅₀ (μM) Lyso PC | IC₅₀ (μM) Coumarine |
|-----|----|----|-------------------|---------------------|
| 24 |  | 3-NH-, 4-COOH, (4-COOH)-phenyl (HOOC, NH, COOH substituted benzene) | 1.6 | 2.5 |
| 25 |  | 4-OCH₃, 3-NH-phenyl-CH₂-COOH | 1.3 | 10 |
| 26 |  | 4-OCH₃, 3-NH-phenyl-CH(CH₃)-COOH | 1.2 | 18 |
| 27 |  | 4-OCH₃, 3-NH-phenyl-CH(COOH)-CH₂-CH=CH₂ | 2.3 | 13 |
| 28 |  | 4-OCH₃, 3-NH-phenyl-CH(OH)-COOCH₃ | — | — |
| 29 |  | 4-OCH₃, 3-NH-phenyl-CH(OCH₃)-COOCH₃ | — | — |

TABLE II-continued
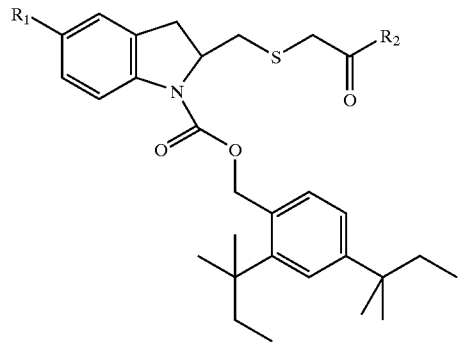
| No. | R₁ | R₂ | IC$_{50}$ ($\mu$M) Lyso PC | IC$_{50}$ ($\mu$M) Coumarine |
|---|---|---|---|---|
| 30 | | 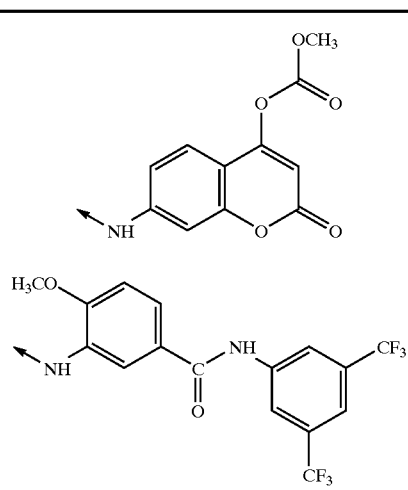 | 28 | |
| 31 | | 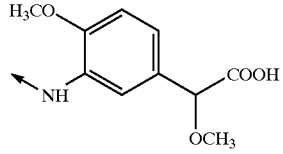 | 44 | |
| 32 | | 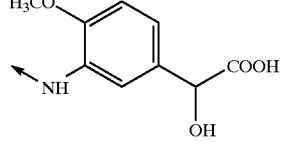 | 3.8 | 5 |
| 33 | | 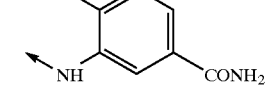 | 2.6 | 5 |
| 34 | | 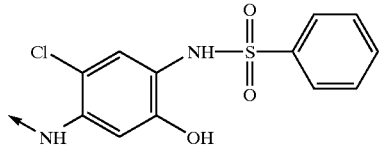 | 24 | >50 |
| 35 | | (structure with Cl, NH-SO₂-phenyl, OH, NH) | 9.1 | 28 |

TABLE II-continued
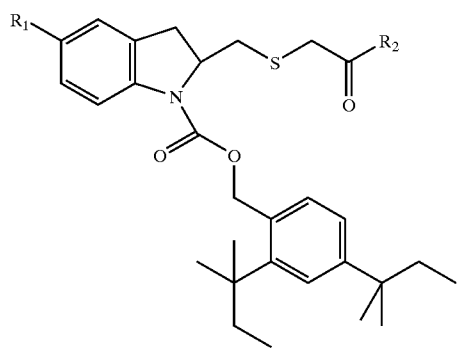
| | | | IC$_{50}$ ($\mu$M) | |
| No. | R$_1$ | R$_2$ | Lyso PC | Cou-marine |
| 36 | —H |  | 2.3 | 4 |
TABLE III
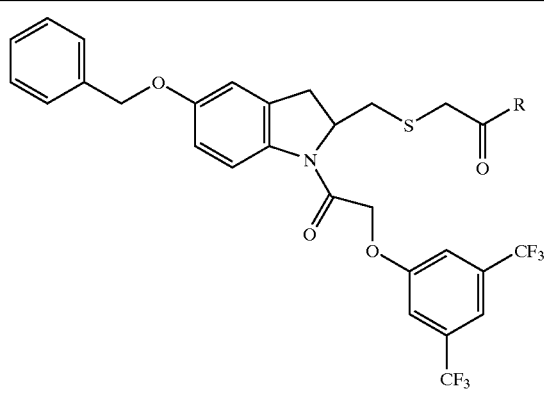
| | | IC$_{50}$ ($\mu$M) | |
| No. | R | Lyso PC | Cou-marine |
| 37 | —OH | 7.6 | >30 |
| 38 | 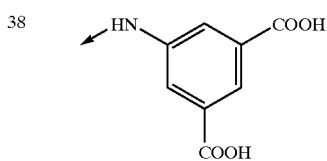 | 6.9 | >50 |
| 39 | 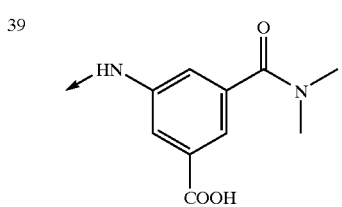 | 4.3 | 18 |
TABLE III-continued
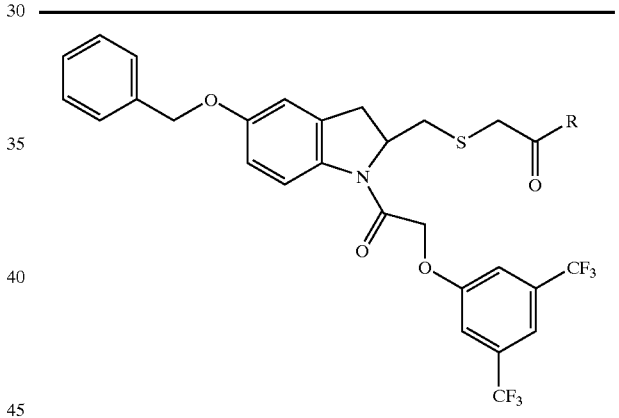
| | | IC$_{50}$ ($\mu$M) | |
| No. | R | Lyso PC | Cou-marine |
| 40 | 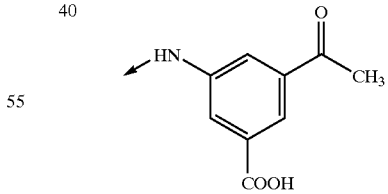 | 6.2 | 11 |
| 41 | 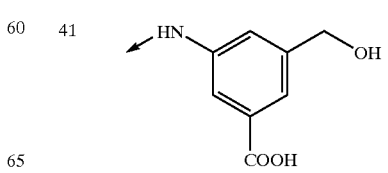 | 2.2 | 22 |

TABLE III-continued
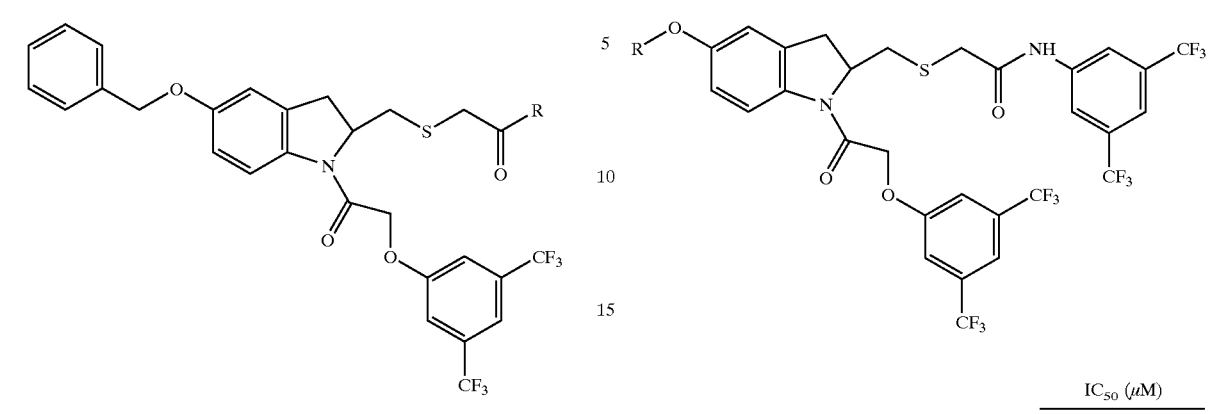
| No. | R | IC$_{50}$ ($\mu$M) Lyso PC | Cou-marine |
|---|---|---|---|
| 42 | (3-COOH, 5-CH(OH)CH$_3$ anilino) | 7.8 | 14 |
| 43 | (3-COOH, 5-C(O)NHCH$_3$ anilino) | 7.1 | 21 |
TABLE IV
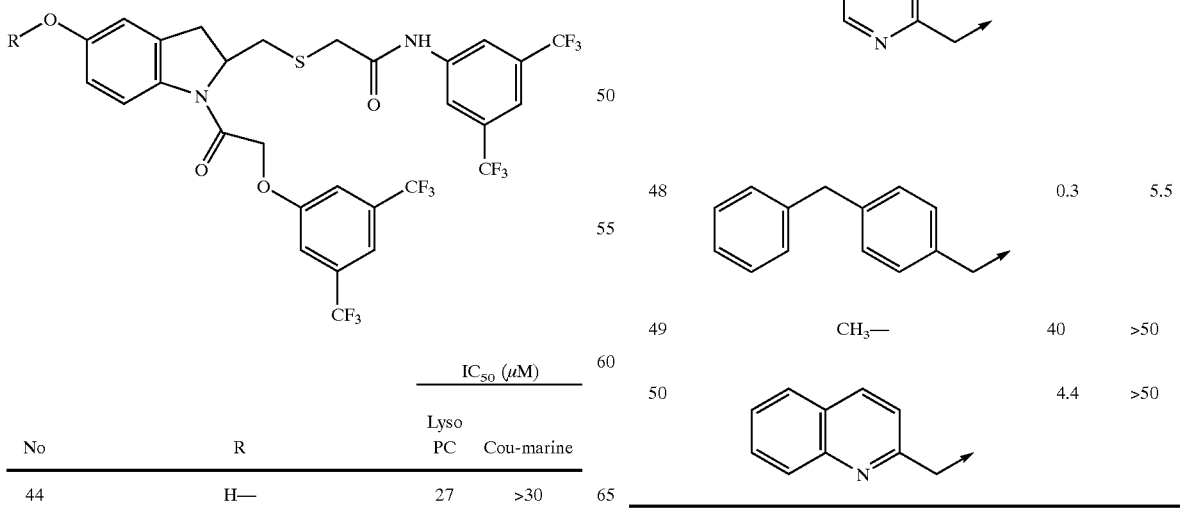
| No | R | IC$_{50}$ ($\mu$M) Lyso PC | Cou-marine |
|---|---|---|---|
| 44 | H— | 27 | >30 |
| 45 | 3,5-dibromobenzyl | 0.37 | 5 |
| 46 | 2-naphthylmethyl | 0.71 | 10 |
| 47 | (5-phenylpyridin-2-yl)methyl | 1.6 | 16 |
| 48 | 4-benzylbenzyl | 0.3 | 5.5 |
| 49 | CH$_3$— | 40 | >50 |
| 50 | quinolin-2-ylmethyl | 4.4 | >50 |

TABLE V
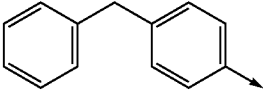
| No. | R₁ | R₂ | IC$_{50}$ ($\mu$M) Lyso PC | IC$_{50}$ ($\mu$M) Coumarine |
|---|---|---|---|---|
| 51 | 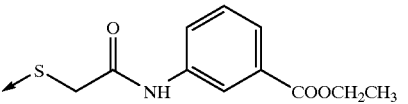 | 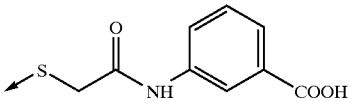 | 36 | |
| 52 | | 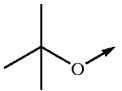 | 8.0 | 26 |
| 53 | 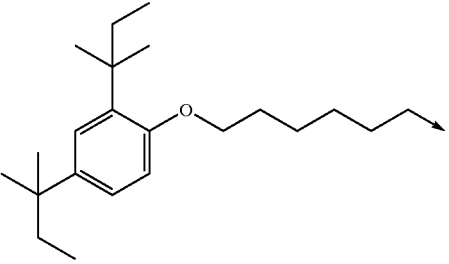 | | 15 | >64 |
| 53 | 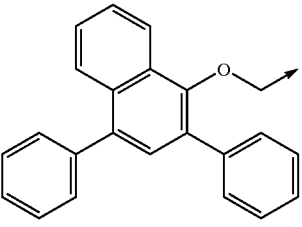 | | 0.23 | 14 |
| 55 | 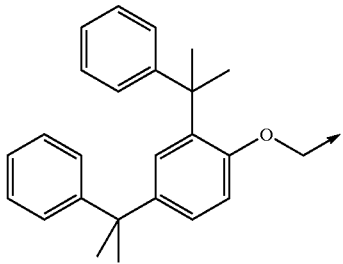 | | 0.45 | 12 |
| 56 |  | | 0.47 | 5 |

TABLE V-continued

| | | | IC$_{50}$ ($\mu$M) | |
|---|---|---|---|---|
| No. | R$_1$ | R$_2$ | Lyso PC | Coumarine |
| 57 | 3,5-di-tert-butyl-2-(4-methoxybenzyl)phenoxymethyl | | 0.26 | 8 |
| 58 | 2,4-di(cyclopent-2-enyl)phenoxymethyl | | 0.56 | 4 |
| 59 | naphthalen-2-yloxymethyl | -SCH$_2$C(O)NH-(4-methoxy-3-carboxyphenyl) | 8.7 | >30 |
| 60 | 4-benzylphenoxymethyl | | 4.6 | >30 |
| 61 | naphthalen-2-yl | | 12.1 | >20 |

TABLE V-continued
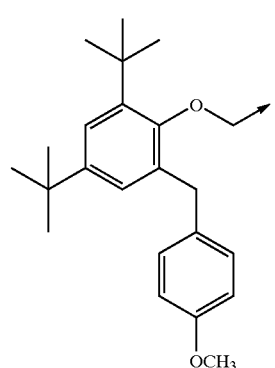
| No. | R₁ | R₂ | IC$_{50}$ ($\mu$M) Lyso PC | IC$_{50}$ ($\mu$M) Coumarine |
|---|---|---|---|---|
| 62 | 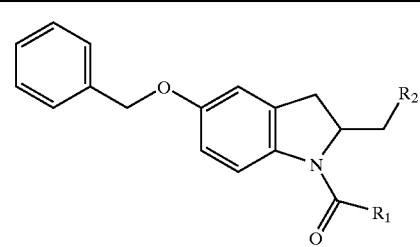 | | 1.7 | 8 |
| 63 | 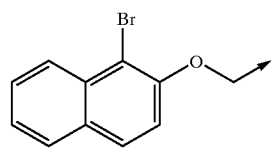 | | | |
| 64 | 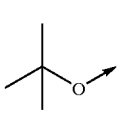 | 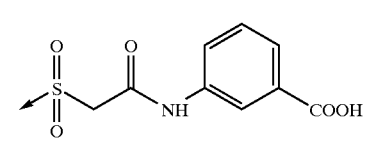 | 17.6 | >64 |
| 65 | CH₃(CH₂)₃O— | 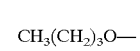 | | |
| 66 |  | | 2.3 | 6 |
| 67 | | 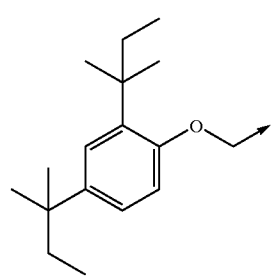 | 0.22 | 10 |

TABLE V-continued
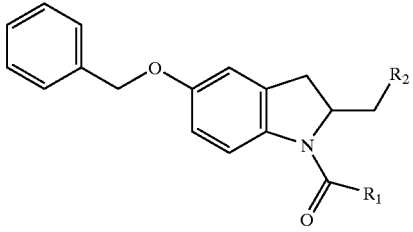
| No. | R₁ | R₂ | IC$_{50}$ ($\mu$M) Lyso PC | IC$_{50}$ ($\mu$M) Coumarine |
|---|---|---|---|---|
| 68 | | 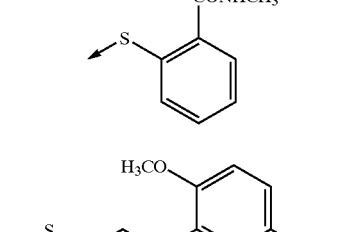 | >50 | >50 |
| 69 | | 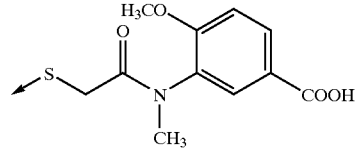 | 19.4 | 6 |
| 70 | | 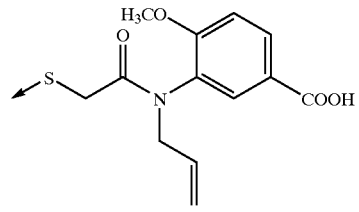 | 0.84 | 19 |
| 71 | | 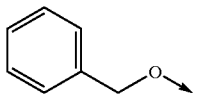 | 5.9 | 12 |
TABLE VI
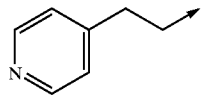
| No. | R₁ | R₂ | R₃ | IC$_{50}$ ($\mu$M) Lyso PC | IC$_{50}$ ($\mu$M) Coumarine |
|---|---|---|---|---|---|
| 72 | 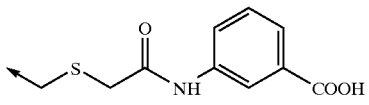 | 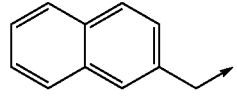 | | | >64 |
| 73 | | | | 1.9 | 6 |

TABLE VI-continued

| No. | R₁ | R₂ | R₃ | IC₅₀ (μM) Lyso PC | IC₅₀ (μM) Coumarine |
|---|---|---|---|---|---|
| 74 | | | 2,4-bis(CF₃)benzyl | 1.1 | 5 |
| 75 | | | 4-methoxy-3-[(carboxymethyl)thio-acetamido]benzoic acid (S-CH₂-C(O)-NH-Ar-COOH, 4-OMe) | 7.0 | 6.2 |
| 76 | | 2-naphthylmethyl | 2-(carboxyphenylthio)methyl | | 4.5 |
| 77 | | 4-methylbenzyl (CH₃-Ar-) | 3,5-bis(CF₃)phenoxymethyl-Ar | | 2.5 |
| 78 | | 4-benzylbenzyl | | | 3 |
| 79 | | | 2,4-bis(CF₃)benzyl | | 4.2 |
| 80 | | 4-carboxybenzyl | 2,4-bis(CF₃)benzyloxymethyl | | 16 |
| 81 | | | 2-naphthylmethoxymethyl | 3.2 | 15 |
| 82 | | | 4-[(3,5-bis(CF₃)phenoxy)methyl]benzyloxymethyl | 0.1 | 15 |

TABLE VI-continued

Structure: indoline with R1 at 5-position, R2 on N, R3 at 2-position

| No. | R1 | R2 | R3 | IC50 (μM) LysoPC | IC50 (μM) Coumarine |
|---|---|---|---|---|---|
| 83 | H— | 2,4-bis(CF3)-benzyl | 3,5-dicarboxyphenyl-NHC(O)- | >50 | >50 |
| 84 | | | CH3-S(O)2-NH-C(O)- | 23 | >50 |
| 85 | | | phenyl-S(O)2-NH-C(O)- | 21 | >50 |
| 86 | H3CO-C6H4-CH2-O- | | 3,5-dicarboxyphenyl-NH-C(O)-NH- | | 17 |
| 87 | | 4-(3,5-bis(CF3)-phenoxymethyl)benzyl | | | 6.5 |

Compounds of the present invention were also tested for in vivo activity in a rat paw edema test according to the procedure described in Example 89. The results are reported in Table VII.

TABLE VII

| Compound No. | % inhibition of rat carrageenan-induced footpad edema |
|---|---|
| 8 | 29 |
| 10 | 8.9 |
| 14 | 34.2 |
| 15 | 21.8 |
| 16 | 26.3 |
| 17 | 29.3 |
| 19 | 10.5 |
| 20 | 19.5 |
| 25 | 17.5 |
| 26 | 10.3 |
| 32 | 26.7 |
| 33 | 4.2 |
| 46 | 12.5 |
| 47 | 7.8 |
| 50 | 11.7 |
| 67 | 17.5 |
| 70 | 21.7 |
| 76 | 8.2 |
| 77 | 13.0 |

As used herein, "phospholipase enzyme activity" means positive activity in an assay for metabolism of phospholipids (preferably one of the assays described in Example 88 below). A compound has "phospholipase enzyme inhibiting activity" when it inhibits the activity of a phospholipase (preferably $cPLA_2$) in any available assay (preferably an assay described below in Example 88 or Example 89) for enzyme activity. In preferred embodiments, a compound has (1) an $IC_{50}$ value of less than about 25 μM, preferably less than about 6 μM, in the LysoPC assay; (2) an $IC_{50}$ value of less than about 50 μM in the vesicle assay; (3) an $IC_{50}$ value of less than about 1 μM in the PMN assay; (4) an $IC_{50}$ value of less than about 15 μM in the Coumarine assay; and/or (5)

measurable activity (preferably at least about 5% reduction in edema, more preferably at least about 10% reduction, more preferably at least about 15%, most preferably about 20–30%) in the rat carrageenan-induced footpad edema test.

Compounds of the present invention are useful for inhibiting phospholipase enzyme (preferably $cPLA_2$) activity and, therefore, are useful in "treating" (i.e., treating, preventing or ameliorating) inflammatory or inflammation-related responses or conditions (e.g., rheumatoid arthritis, psoriasis, asthma, inflammatory bowel disease, and other diseases mediated by prostaglandins, leukotrienes or PAF) and other conditions. such as osteoporosis, colitis, myelogenous leukemia, diabetes, wasting and atherosclerosis.

The present invention encompasses both pharmaceutical compositions and therapeutic methods of treatment or use which employ compounds of the present invention.

Compounds of the present invention may be used in a pharmaceutical composition when combined with a pharmaceutically acceptable carrier. Such a composition may also contain (in addition to a compound or compounds of the present invention and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition may further contain other anti-inflammatory agents. Such additional factors and/or agents may be included in the pharmaceutical composition to produce a synergistic effect with compounds of the present invention, or to minimize side effects caused by the compound of the present invention.

The pharmaceutical composition of the invention may be in the form of a liposome in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of a compound of the present invention is administered to a mammal having a condition to be treated. Compounds of the present invention may be administered in accordance with the method of the invention either alone or in combination with other therapies such as treatments employing other anti-inflammatory agents, cytokines, lymphokines or other hematopoietic factors. When co-administered with one or more other anti-inflammatory agents, cytokines, lymphokines or other hematopoietic factors, compounds of the present invention may be administered either simultaneously with the other anti-inflammatory agent(s), cytokine(s), lymphokine(s), other hematopoietic factor(s), thrombolytic or anti-thrombotic factors, or sequentially. If administered sequentially, the attending physician will decide on the appropriate sequence of administering compounds of the present invention in combination with other anti-inflammatory agent(s), cytokine(s), lymphokine(s), other hematopoietic factor(s), thrombolytic or anti-thrombotic factors.

Administration of compounds of the present invention used in the pharmaceutical composition or to practice the method of the present invention can be carried out in a variety of conventional ways, such as oral ingestion, inhalation, or cutaneous, subcutaneous, or intravenous injection.

When a therapeutically effective amount of compounds of the present invention is administered orally, compounds of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% compound of the present invention, and preferably from about 25 to 90% compound of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of compound of the present invention, and preferably from about 1 to 50% compound of the present invention.

When a therapeutically effective amount of compounds of the present invention is administered by intravenous, cutaneous or subcutaneous injection, compounds of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments which the patient has undergone. Ultimately, the attending physician will decide the amount of compound of the present invention with which to treat each individual patient. Initially, the attending physician will administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 μg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the attending physician will decide on the appropriate duration of intravenous therapy using the pharmaceutical composition of the present invention.

Methods of Synthesis for Examples 1–87

Compounds of the present invention can be prepared according to the following methods. Temperatures are in degrees Celsius.

Method A

Indol-2-carboxylic acid ethyl ester I is converted to aldehyde II in two steps: reduction with lithium aluminum hydride (LAH) or other hydride in a suitable solvent such as tetrahydrofuran (THF) at 0° C., and then oxidation with an oxidizing reagent such as manganese dioxide in a solvent such as THF. Deprotonation of aldehyde II with a strong base such as potassium hexamethyldisilyl amide (KHMDS) in THF, followed by reaction with a chloroformate in the presence of a base, such as triethyl amine, produces carbamate III. III is transformed into bromide IV in two steps: (1) reduction with sodium borohydride in an alcoholic solution and (2) reaction with carbon tetrabromide in the presence of a phosphine reagent such as bis (diphenylphosphino)propane in dichloromethane. Displacement of the bromine in IV with potassium phenoxide, prepared by reaction of a phenol with KHMDS, in a suitable solvent such as THF or DMF affords ether V. V can be converted to either trifluoromethyl ketone VII or to carboxylic acid IX in different procedures. Reaction of V with trifluoromethyl trimethylsilane (TMSCF$_3$) in the presence of tetrabutylammonium fluoride gives trifluoromethyl alcohol, which is then oxidized with periodinane (Dess-Martin reagent) in dichloromethane to afford ketone VI. In this stage the carbamate can be removed with either trifluoroacetic acid (TFA) or with a base such as sodium hydroxide. The indole nitrogen is then alkylated with a suitable alkyl bromide in the presence of a base such as sodium hydride to produce VII. Alternatively, V can be deprotected with TFA or aqueous base, and then reacted with alkyl bromide to give VIII, which is oxidized with sodium chlorite in an aqueous THF to yield acid IX.

Method B

2-Indolyl carboxylic acid ethyl ester I is deprotonated with a strong base such as sodium hydride (NaH) in THF, and then reacted with a suitable alkyl bromide to give X. Hydrolysis of X with a aqueous base such as sodium hydroxide and reaction with aniline or a substituted aniline in the presence of a carbodiimide such as dimethylaminopropyl ethylcarbodiimide hydrochloride (EDCI) in a suitable solvent such as dichloromethane affords amide XI. XI is hydrolyzed to corresponding acid XII in a aqueous base such as sodium hydroxide.

Method C

Indole I can be brominated on the 3-position by reaction with a bromine or N-bromosuccinimide in a suitable solvent such ascarbon tetrachloride or dichloromethane to yield bromide XIII. Reaction of XIII with a suitable alkyl bromide in the presence of a strong base such as NaH in THF or DMF affords indole XIV. Palladium mediated coupling of XIV with a suitable alkene in the presence of phosphine and a base such as triethyl amine produces 3-substituted indole XV. XV can be converted to amide XVII in two step reactions: (1) hydrolysis with aqueous base such as NaOH and (2) coupling with an amine in the presence of carbodiimide such as EDCI. Ester XIV can be transformed to lithium salt XVIII by hydrolysis with aqueous base and then reaction with lithium hydroxide in a suitable solvent such as ether. Lithiation with n-butyl lithium in a suitable solvent such as THF, and then acylation with an acyl chloride in THF affords ketone XIX. Carbodiimide (EDCI) catalyzed coupling of XIX and a suitable amine gives amide XX.

Method D

Indole I can be converted to XXI in two steps: (1) reduction with LAH in a solvent such as THF and (2) silylation with t-butyldimethylsilyl chloride (TBDMSC1) in a solvent such as dichloromethane or DMF in the presence of a base such as imidazole. Treatment of XXI with Grignard reagent such as ethyl magnesium bromide in a solvent such as THF at −60° C., acylation of the resulting magnesium salt with a suitable acyl chloride such as acetyl chloride in ether and finally, alkylation on the nitrogen with an alkyl halide such as ethyl bromide in the presence of a strong base such as NaH in DMF affords ketone XXII. The silyl group on XXII is removed using tetrabutylammonium fluoride in a solvent such THF, the resulting alcohol is then converted to bromide using carbon tetrabromide and bis (diphenylphosphino)ethane in a solvent such as dichloromethane to yield bromide XXIII. Displacement of the bromine of XXIII with a thiol compound in the presence of a base such as Cs$_2$CO$_3$, or with an alcohol in the presence of a strong base such as NaH in DMF affords XXIV (sulfide, or ether respectively).

Method E

Aldehyde II, prepared by Method A, can be alkylated by a suitable alkyl bromide (or iodide), such as benzyl bromide or ethyl iodide in the presence of a strong base such as sodium hydride or KHMDS in a solvent such as DMF to yield XXV. XXV can be converted to an unsaturated acid XXVI by two steps: (1) Wittig reaction with a suitable reagent such as trimethyl phosphonoacetate in the presence of a base such as sodium hydride in a solvent such as THF and (2) Hydrolysis by aqueous sodium hydroxide. Coupling reaction of XXVI with an amine catalyzed by a diimide such as EDCI (dimethylaminopropyl ethylcarbodiimide hydrochloride), followed by hydrolysis with aqueous base such as sodium hydroxide affords XXVII.

Method F

Indole I is reduced with LAH in a solvent such as THF. A second reduction with sodium cyanoborohydride in a solvent such as acetic acid to yield alcohol XXVIII. Protection of the nitrogen of XXVIII with t-butoxycarbonyl (BOC) using di-t-butyldicarbonate ((BOC$_2$)O) in the presence of a base such as triethylamine affords carbamate XXIX. The hydroxyl group in XXIX is mesylated using mesyl chloride and triethylamine in a solvent such as dichloromethane, and then displaced by either a thiol or an alcohol as described in METHOD D to produce indoline XXX. Deprotection of XXX using trifluoroacetic acid affords XXXI, which is either acylated (acyl chloride, triethylamine, dichloromethane) or alkylated (alkyl halide, K$_2$CO$_3$, DMF) to afford XXXII, or XXXIII respectively.

Method G

Carboxylic acid XXXIV is converted to aldehyde XXXV in two steps: (1) reaction with N,O-dimethylhydroxy amine in the presence of EDCI in a solvent such as dichloromethane, and (2) reduction with diisobutyl aluminum hydride (DIBAL) in a solvent such as THF. Treatment of XXXV with trimethyl phosphonoacetate in the presence of a strong base such as KHMDS in a solvent such as THF results in the formation of ester XXXVI. Reduction of XXXVI with tin in hydrogen chloride, followed by cyclization in a heated inert solvent such as toluene gives XXXVII. Alkylation on nitrogen of XXXVII under conditions described in METHOD F, and then hydrolysis of the ester with aqueous base such as NaOH affords acid XXXVIII. XXXVIII can be converted to an amide XXXIX by coupling with a suitable amine such as benzylamine in the presence of EDCI.

Method H

Aldehyde XXXV, prepared in METHOD G, is subjected to a Wittig reaction using methyl triphenylphosphonium iodide in the presence of a strong base such as KHMDS or NaH in a solvent such as THF to afford alkene XL. Reduction of the nitro group of XL with iron powder in an ammonium chloride solution, followed by treatment with benzyl chloroformate in the presence of a base such as triethyl amine produces carbamate XLI. XLI is treated with iodine in a basic solution such as aqueous $NaHCO_3$ in THF to yield iodide XLII. Displacement of the iodine on XLII with lithium benzoate in a solvent such as DMF, followed by hydrolysis with NaOH affords alcohol XLIII.

Method I

Indoline XXVIII, prepared in METHOD F or METHOD H, can be either acylated by reaction with an acyl chloride in the presence of a base such as triethyl amine or alkylated using alkyl halide in the presence of $K_2CO_3$ in a solvent such as DMF to produce alcohol XLIV. Treatment of XLIV with mesyl chloride and triethyl amine in a solvent such as dichloromethane, followed by displacement with a thiol such as methyl mercaptoacetate in the presence of a base such as $Cs_2CO_3$ in a solvent such as acetonitrile yields ester XLV. Hydrolysis of XLV with an aqueous base such as NaOH gives acid XLVI, which can be coupled with an amine catalyzed by a diimide such as EDCI in a solvent such as dichloromethane to afford amide XLVII. XLVII can be alkylated on the amide nitrogen by treatment with alkyl halide and strong base such as NaH in DMF. Hydrolysis of the resulting amide with aqueous base such as NaOH gives acid XLIX. XLIV can also be directly hydrolyzed with NaOH to a carboxylic acid XLVIII.

Method J

METHOD J illustrates the synthesis of alpha-substituted aminophenylacetic acid esters. Ester L can be deprotonated with a strong base such as lithium diisobutylamide (LDA) in a solvent such as THF, and subsequently alkylated with an alkyl halide such as methyl iodide to give LI. Reduction of LI to amine LIII can be accomplished using hydrogenation catalyzed by palladium in a solvent such as ethanol. L can be oxidized to alcohol LII using LDA and oxaziridine in a solvent such as THF. Alkylation of LII with a alkylating reagent such as methyl iodide in the presence of a strong base such as NaH in DMF, followed by catalytic hydrogenation in the presence of palladium produces amine LIV.

Method K

METHOD K illustrates the synthesis of substituted aminobenzoic acid esters. Mono-acid LV can be converted to amide LVI by the following steps: (1) reaction with oxalyl chloride in dichloromethane to form acid chloride and (2) treatment with a suitable amine such as dimethyl amine. Reduction of the nitro group to the amine is accomplished with hydrogenation catalyzed by palladium as described in METHOD J. LV can be reduced to alcohol LVIII with hydroborane-THF complex in THF. Protection of the hydroxy group as a silyl ether using TBDMSC1 in the presence of imidazole and subsequently, reduction of the nitro group ($H_2$/Pd—C) to the amine affords LIX. LVIII can be converted to the secondary alcohol LX in two steps: (1) oxidation with a suitable reagent such as manganese dioxide ($MnO_2$) in ethyl acetate and (2) addition of a desired Grignard reagent such as methyl magnesium bromide in THF. Oxidation of LX with $MnO_2$ in THF and reduction of the nitro group ($H_2$/Pd—C) produces ketone LXIII. Reduction of LVII ($H_2$/Pd—C) yields LXI.

Method L

Alcohol LXIV, prepared in METHOD I, can be debenzylated by hydrogenolysis catalyzed by palladium on carbon in a solvent such as ethanol. The resulting alcohol is treated with p-methoxybenzyl chloride in the presence of $K_2CO_3$ in a solvent such as THF to afford LXV. Alcohol LXV can be transformed into ether or sulfide LXVI by the procedures described in METHOD D. Deprotection of the p-methoxybenzyl group with TFA in a solvent such as dichloromethane, and subsequent alkylation on oxygen with a suitable reagent such as 4-benzylbenzyl bromide in the presence of $K_2CO_3$ in a solvent such as THF affords LXVII.

EXPERIMENTAL SECTION

The Examples which follow further illustrate the invention. All temperatures set forth in the Examples are in degrees Celsius. All the compounds were characterized by proton magnetic resonance spectra taken on a Varian Gemini 300 spectrometer or equivalent instruments.

EXAMPLE 1

2-(2-(1-Phenylmethoxycarbonyl-5-phenylmethoxy) indolyl)methoxybenzoic Acid

Step 1: 2-(5-Phenylmethoxy)indolyl Aldehyde 12.3 g (42 mmol) of ethyl 2-(5-(phenylmethoxy)indolyl) carboxylate was dissolved in 100 mL of THF, to which was added 130 mL (130 mmol) of 1 M solution of lithium aluminum hydride in THF at 0° C. The reacton was stirred at this temperature for 2 hours and quenched by adding 65 mL of 6 N NaOH solution slowly. The product was extracted with ethyl acetate, and the organic phase was washed with aqueous ammonium chloride. Evaporation of the solvent afforded crude alcohol, which without further purification was dissolved in 400 mL of THF, 52 g of manganese(IV) oxide was added, and the mixture was stirred at room temperature overnight. Removal of manganese oxide by filtration and flash chromatographic purification using 3:1 hexane:ethyl acetate yielded 8.15 g of the title compound.

Step 2: Benzyl (1-(2-Formyl-5-phenylmethoxy)indolyl) formate

To a solution of 6.9 g (27.5 mmol) of the aldehyde of step 1in 140 mL of THF was slowly added 61 mL (30.5 mmol) of 0.5 M solution of potassium bis(trimethylsilyl)amide in toluene at −35° C. After stirring at this temperature for 10 min, 4.4 mL (29.5 mmol) of benzyl chloroformate was added at −35° C., and the mixture was then warmed from −35° C. to 0° C. for 3.5 hours. The reaction was quenched by pouring into aqueous ammonium chloride.

Aqueous work up and flash chromatography using 12:1 toluene:ethyl acetate afforded 4.8 g of the title compound.

Step 3: Benzyl (1-(2-Hydroxymethyl-5-phenylmethoxy) indolyl)formate

To a solution of 2.9 g (7.5 mmol) of the aldehyde of step 2 in 40 mL of THF and 20 mL of trifluoroethanol was added 760 mg (20 mmol) of sodium borohydride at 0° C. The mixture was stirred at 0° C. for 30 min and then quenched by adding aqueous ammonium chloride. Flash chromatography using 2:1 hexane-ethyl acetate afforded 2.2 g of the title compound.

Step 4: Benzyl (1-(2-Bromomethyl-5-phenylmethoxy)indolyl)formate

To a solution of 2.2 g (5.7 mmol) of the alcohol of step 3 and 2.05 g (5.0 mmol) of 1,3-bis(diphenylphosphino)propane in 60 mL of dichloromethane was added a solution of 2.0 g (6 mmol) of carbon tetrabromide in 4 mL of dichloromethane at 15° C. The mixture was stirred at room temperature for 2 hours and 1 g (3 mmol) of 1,3-bis(diphenylphosphino)propane was added at room temperature. After 1 hour stirring, the reaction was quenched by adding aqueous ammonium chloride. Aqueous work up and flash chromatography using 4:1 hexane:ethyl acetate afforded 1.7 g of the title compound.

Step 5: Benzyl (1-(2-(2-Formylphenoxy)methyl-5-phenylmethoxy)indolyl)formate

To a solution of 439 mg (3.6 mmol) of methyl 2-hydroxybenzoate in 18 mL of THF was added 6 mL (3 mmol) of 0.5 M solution of potassium bis(trimethylsilyl)amide in toluene at 0° C. The solution was stirred at 0° C. for 10 min, to which was added a solution of 1.25 g (2.8 mmol) of the bromide, prepared in step 4, in THF at 0° C. The reaction was warmed to room temperature and stirred at this temperature for 2 hours. After aqueous work up ($NH_4Cl$/ethyl acetate), the organic solvent was collected, dried over sodium sulfate and evaporated. The product was solidified and washed with ethyl acetate:hexane 1:1. Yield 690 mg (51%).

Step 6:

120 mg (0.24 mmol) of the aldehyde of step 5 was dissolved in 11 mL of 5:1:5 THF-acetonitrile-2,2-dimethylethanol. To this solution was added a solution of 56 mg (0.5 mmol) of sodium chlorite in 0.5 mL water and 1 drop of aqueoues hydrogen peroxide solution. After 4 hours, another 56 mg (0.5 mmol) of sodium chlorite was added. The mixture was stirred at room temperature for three days. Aqueous work up and flash chromatography using 2.5:1:0.05 hexane:ethyl acetate-acteic acid afforded 110 mg of the title compound.

EXAMPLE 2

4-(2-(1-Phenylmethoxycarbonyl-5-phenylmethoxy)indolyl)methoxybenzoic Acid

The title compound was prepared according to the procedure described in Example 1, but using 4-hydroxybenzaldehyde.

EXAMPLE 3

3-(2-(1-Phenylmethoxycarbonyl-5-phenylmethoxy)indolyl)methoxybenzoic Acid

The title compound was prepared according to the procedure described in Example 1, but using 3-hydroxybenzaldehyde.

EXAMPLE 4

Benzyl (1-(2-(2-(1-Oxo-2,2,2-trifluoroethyl)phenoxy)methyl-5-phenylmethoxy)indolyl)formate Step 1: Benzyl (1-(2-(2-(1-Hydroxy-2,2,2-trifluoroethyl)phenoxy)methyl-5-phenylmethoxy)indolyl)-formate A solution of 0.4 g (0.8 mmol) of the aldehyde, prepared in step 1 of Example 1, in 4 mL of THF was cooled to 0° C. To this were added 0.24 mL (1.6 mmol) of trifluoromethyl trimethylsilane and 5 mg of tetrabutylammonium fluoride trihydrate. The reaction was stirred for 2.5 hpurs at 0° C., and additional 0.2 mL (1.3 mmol) of trifluoromethyl trimethylsilane and 5 mg of tetrabutylammonium fluoride trihydrate were added. After stireed at 0° C. for 2 hours, the reaction was worked up with aqueous ammonium chloride and ethyl acetate. Silica gel chromatographic purification using 4:1 hexane-ethyl acetate afforded corresponding TMS ether. Treatment of TMS ether with 1.3 mL of IN Hcl solution at room temperature, aqueous woukup using brine and ethyl acetate and chromatographic purification using 3:1 hexane-ethyl acetate gave 230 mg of the titled compound.

Step 2:

To a solution of 150 mg (0.27 mmol) of trifluoroethanol, prepared in step 1, in 5.5 mL of dichloromethane was added 255 mg (0.6 mmol) of the Dess-Martin's periodinate. The mixture was stirred at room temperature for 1 hour, and then partitioned between aqueous $NaHCO_3$ and ethyl acetate. The organic phase was washed once with aqueous $NaHCO_3$ and purified with chromatography using 3:1 hexane-ethyl acetate to yield 150 mg of the titled compound.

EXAMPLE 5

3-(2-(1-Benzyl-5-benzyloxy)indolecarboxamido)benzoic Acid

Step 1: Ethyl 2-(1-Benzyl-5-benzyloxy)indolecarboxylate

To a solution of 1 g (3.4 mmol) of ethyl 5-benzyloxyindole-2-carboxylate in 12 ml of DMF, sodium hydride (0.163 g, 60% oil dispersion, 4.07 mmol) was added at room temperature. The reaction was stirred for 30 minutes. Benzyl bromide (0.44 mL, 3.73 mmol) was added at this time and the reaction stirred for another hour. On completion of the reaction (monitored by TLC=0.5 Rf in 3:1 Hexane:Ethyl acetate) it was quenched with water, extracted with ethyl acetate (3x). Organic layers were dried over magnesium sulfate, concentrated and used for the next step.

Step 2: 2-(1-Benzyl-5-benzyloxy)indolecarboxyic Acid

The ester (3.4 mmol), prepared in step 2, was dissolved in THF (20 mL), methanol (20 mL) and then 1N NaOH (15 mL) was added. The reaction mixture was stirred at room temperature over night at which time it was concenterated, diluted with water, acidified to pH 5 with 10% HCl and extracted with ethyl acetate (3x), the organic extracts were dried over magnesium sulfate and concentrated to give the indole acid (1.14 g, 94.2%, TLC=0.5 Rf in 1:1 Hexane:Ethyl acetate with 1% acetic acid).

Step 3: Ethyl 3-(2-(1-Benzyl-5-benzyloxy)indolecarboxamido)benzoate

The acid (0.54 g, 1.5 mmol) of step 2, 1-(3-dimethylaminopropyl)-3-ethylcarbodiimide (EDCI) (0.32 g, 1.66 mmol), 4-dimethylaminopyridine (DMAP) (0.018 g, 0.15 mmol) and ethyl 3-aminobenzoate (0.27 g, 1.66 mmol) were stirred in tetrahydrofuran (9 mL) at room temperature overnight. The next day the reaction was diluted with ethyl acetate and water, extracted with ethyl acetate (3x), dried over magnesium sulfate and concentrated. The crude material was purified on silica gel using 3:1 hexane:ethyl acetate to give pure amide (0.578 g, 76%, TLC=0.4 Rf in 3:1 Hexane:Ethyl acetate).

Step 4:

The ester (0.578 g, 1.15 mmol), prepared in step 3, was dissolved in THF (13.6 mL), methanol (13.6 mL) and then 1N NaOH (9.6 mL) was added. The reaction mixture was stirred at room temperature overnight at which time it was concenterated, diluted with water, acidified to pH 5 with 10% HCl and extracted with ethyl acetate (3×), the organic extracts were dried over magnesium sulfate and concentrated to give the titled compound (0.437 g, 80%, TLC=0.5 Rf in 3:1 hexane:ethyl acetate with 1% acetic acid).

THE EXAMPLES 6, 7, 8, 9, 10 AND 11 IN TABLE I WERE PREPARED BY THE PROCEDURE OF EXAMPLE 5 USING SUITABLE AMINES AND ALKYL HALIDES

EXAMPLE 12

3-(2-(3-(2,4-bis(1,1-Dimethypropyl)phenoxyacetyl)- 5-methoxy-1-methyl)indolyl)methylthioacetamido- 4-methoxybenzoic Acid Step 1: 2-(5-Methoxy)indolylmethanol Ethyl 5-methoxy-2-indolcarboxylate (30 g, 102 mmol) is dissolved in 250 mL of THF and cooled to 0° C. and Lithium Aluminum Hydride (LAH) (255 mL of a 1.0 M solution in THF) is added via addition funnel over 40 minutes. The reaction was stirred a further 2 hours at 0° C. and then worked up by the addition of 4N NaOH (190 mL). The resulting salts are filtered and washed with ethyl acetate (3×400 mL), the filtrates are combined and dried over $MgSO_4$ and concentrated to yield 24.8 g of alcohol, which was used for the next reaction directly.

Step 2: 2-(5-Methoxy)indolylmethoxy-tert-buthyldimethylsilane

The crude indole alcohol prepared in step 1(6.2 g, 32.6 mmol) was dissolved in DMF (10.5 mL). To this solution was added imidazole (5.5 g, 81.5 mmol) and t-butyldimnethylsilyl chloride (5.4 g, 35.8 mmol). The mixture was stirred at room temperature overnight. The reaction was poured into water and extracted with ethyl acetate (3×). Organic layers were dried over magnesium sulfate and concentrated. The crude material was purified on a silica gel column using 19:1 hexane:ethyl acetate to give pure product (9.5 g, 31 mmol, 94% yield, TLC: 0.8 Rf in toluene:ethyl acetate 2:1)

Step 3: 3-(2-tert-Butydimethylsilyloxymethyl-5-methoxy) indolyl (2,4-bis(1,1-Dimethylpropyl)phenoxy)methyl Ketone 2.32 g (7.95 mmol) of 2,4-Bis-tert-amylphenoxyacetic acid was dissolved in dichloromethane (21 mL), oxalyl chloride (1.4 mL 16.1 mmol) was added, followed by dimethyl formamide (0.5 mL) at room temperature. After one hour the reaction is concentrated and azeotroped with toluene and left on the high vacuum for two hours.

In another reaction vessel, a solution of the silyl protected indole, prepared in step 2, (2 g, 6.56 mmol) in ether (20 mL) was added dropwise to ethyl magnesium bromide (2.4 mL of a 3M solution in ether, 7.2 mmol) in ether (10 ml), the latter maintained at –78° C. The reaction was stirred at –60° C. for 2 hr. To this reaction solution, the above prepared acid chloride in ether (4 mL) was added slowly. The reaction was maintained between –50° C. and –60° C. for another 2 hrs. The reaction was then quenched with saturated sodium bicarbonate. Extracted with ethyl acetate (3×). Organic layers were dried over magnesium sulfate and concentrated. The crude material was purified on a silica gel column using 19:1 Hexane:Ethyl acetate to give pure product (2.36 g, 50%, TLC: 0.15 Rf in hexane:ethyl acetate 19:1.

Step 4: 3-(2-tert-Butydimethylsilyloxymethyl-5-methoxy-1-methyl)indolyl (2,4-bis(1,1-Dimethypropyl)phenoxy) methyl Ketone To the ketone (1.97 g, 3.4 mmol) of in step 3 in 12 ml of DMF, sodium hydride (0.163 g, 60% oil dispersion, 4.07 mmol) was added at room temperature. The reaction was stirred for 30 minutes. Methyl iodide (0.23 mL, 3.73 mmol) was added at this time and the reaction stirred for another hour. On completion of the reaction (monitored by TLC) it was quenched with water, extracted with ethyl acetate (3×). Organic layers were dried over magnesium sulfate, concentrated and the crude product was used for the next step.

Step 5: 3-(2-Hydroxymethyl-5-methoxy-1-methyl)indolyl (bis-2,4-(1,1-Dimethypropyl)phenoxy)methyl Ketone A mixture of N-methyl indole, prepared in step 4, (2.01 g, 3.4 mmol) and tetra-butyl ammoniumfluoride (TBAF) (8.5 mL of a 1M solution in THF, 8.5 mmol) in THF (17.9 mL) were stirred at room temperature for one hour. At this time the reaction was diluted with ethyl acetate and water, extracted with ethyl acetate (3×), dried over magnesium sulfate and concentrated. The crude material was purified on silica gel using hexane:ethyl acetate 2:1 to yield pure alcohol (0.82 g, 60%, TLC: 0.3 Rf in 2:1 hexane:ethyl acetate).

Step 6: Methyl 3-(2-(3-(2,4-bis(1,1-Dimethypropyl) phenoxy)acetyl-5-methoxy-1-methylindolyl) methylthioacetamido)-4-methoxybenzoate The indole alcohol, prepared in step 5, (0.20 g, 0.43 mmol) was dissolved in dichloromethane (0.7 mL) and treated with triethylamine (0.1 mL, 0.64 mmol) and cooled to 0° C. at which time mesyl chloride (0.04 mL 0.52 mmol) was added over 5 minutes, followed by addition of two drops of DMF. The reaction was stirred for a further 2 hour at 0° C., it was then concentrated and used directly for the next reaction.

The above prepared mesylate was dissolved in DMF (0.8 mL). The solution was degassed by bubbling nitrogen through for ten min. Cesium carbonate (0.25 g, 1.29 mmol) was added and then thiol (0.11 g, 0.43 mmol), prepared in Intermediate 1, was added. The mixture was stirred overnight, then poured into saturated ammonium chloride and extracted with ethyl acetate (3×), dried, concentrated. The crude material was purified on a silica gel column using hexane:ethyl=2:1 acetate to give pure product (0.12 g, 40%, TLC: 0.3 Rf in hexane:ethyl acetate 1:1).

Step 7:

The ester, prepared in step 6, (0.12 g, 0.17 mmol) was dissolved in THF (1.0 mL), methanol (1.0 mL) and then 1N NaOH (0.4 mL) was added. The reaction mixture was stirred at room temperature overnight at which time it was concenterated, diluted with water, acidified to pH 5 with10% HCl and extracted with ethyl acetate (3×), the organic extracts were dried over magnesium sulfate and concentrated to give the titled compound (85 mg, 72%, TLC=0.3 Rf in 1:1 Hexane:Ethyl acetate with 1% acetic acid).

EXAMPLES 13, 14, 15 AND 16 IN TABLE 1 WERE PREPARED BY THE PROCEDURES OF EXAMPLE 12 USING ETHYL 2-(5-BENZYLOXY)INDOLECARBOXYLATE, ACETYL CHLORIDES AND SUITABLE ALKYL HALIDES

EXAMPLE 17

3-(2-(-5-Benzyloxy-1-(2,4-bis(1,1-dimethy)propyl) phenoxyacetyl)indolinyl) methylthioacetamidobenzoic Acid Step 1: 2-(5-Benzyloxy)indolinylmethanol Ethyl 5-benzyloxy-2-indolecarboxylate (30 g, 102 mmol) was dissolved in 250 mL of THF and cooled to 0° C., to which Lithium Aluminum Hydride (LAH) (255 mL of a 1.0 M solution in THF) was added via addition funnel over 40 minutes. The reaction was stirred a for 2 hours at 0° C. and then worked up by the addition of 4N NaOH (190 mL). The resulting salts were filtered and washed with ethyl acetate (3×400 mL), the filtrates were combined, dried over MgSO$_4$ and concentrated to yield 24.8 g. This crude material was then dissolved in glacial acetic acid (260 mL) and the resulting yellow solution was cooled to 15° C., sodium cyanoborohydride (18.5 g, 294 mmol) was added portionwise over 10 minutes, and the resulting mixture was stirred for 3 hours. The reaction was quenched by pouring slowly into 1.5 liters of nearly saturated NaHCO$_3$, extracted with ethyl acetate (3×), dried over MgSO$_4$ and concentrated to yield a orange solid (29.6 g).

Step 2: tert-Butyl 1-(5-Benzyloxy-2-Hydroxymethyl) lindolinylformate 25 g (85 mmol) of crude alcohol, prepared in step 1, and 4-dimethylamino pyridine (DMAP) (1.19 g, 9.78 mmol) were dissolved in dichloromethane (180 mL). The solution was cooled to 0° C. and then triethylamine (13.6 mL, 98 mmmol) was added to it. After 10 minutes of stirring a solution of di-tert-butyl dicarbonate (21.3 mL, 98 mmol) dissolved in dichloromethane (20 mL) was added via syringe pump over 2 hours. After 1 hour of stirring the reaction was quenched by the addition of 1/2 saturated NH$_4$Cl solution and extracted with CH$_2$Cl$_2$ (3×), dried over MgSO$_4$ and concentrated to yield 36.3 g of a yellow oil, which was purified by column chromatography using a hexane:ethyl acetate gradient of 9:1 to 4:1 to 1:1 to deliver the product (15.25 g, 44%).

Step 3: Ethyl 2-(5-Benzyloxy-1-tert-butoxycarbonyl) indolinylmethylthioacetate

The carbamate, prepared in step 2, (15.25 g, 43 mmol) was dissolved in dichloromethane (180 mL) and treated with triethylamine (9.0 mL, 64.4 mmol). The solution was cooled to −10° C. at which time mesyl chloride (4.3 mL. 56 mmol) was added over 5 minutes. The reaction was stirred for a further 2 hour at −10° C., it was then concentrated and used directly for the next displacement reaction.

The above prepared mesylate was dissolved in DMF (85 mL), degassing the solvent is strongly reccomended) cesium carbonate (35 g, 107.3 mmol) was added and then ethyl thioacetate (4.70 mL, 42.9 mmol) was added. The mixture was stirred for 1 day, then poured into 1/2 sturated ammonium chloride and extracted with ethyl acetate (3×), dried, concentrated and chromatographed (hexane:ethyl acetate gradient 10:1 to 4: 1) to yield 8.55 g of a yellow oily product.

Step 4: 2-(5-Benzyloxy-1-tert-butoxycarbonyl) indolinylmethylthioacetic Acid

To a solution of the indoline ester prepared in step 3, (5 g, 11 mmol) in 1M potassium hydroxide in methanol (100 mL), water (10 mL) was added. The reaction was stirred at room temperature for two hours at which time it was diluted with water, acidified to pH 5 with10% HCl and extracted with ethyl acetate (3×), the organic extracts were dried over magnesium sulfate and concentrated to give the indoline acid (4.5 g, 95.5%, TLC=0.5 Rf in 2:1 hexane:ethyl acetate with 1% acetic acid). The crude material was used for the next step directly.

Step 5: Ethyl 3-(2-(5-Benzyloxy-1-tert-butoxycarbonyl) indolinyl)methylthioacetamidobenzoate The acid (3 g, 7 mmol), prepared in step 4, 1-(3-dimethylaminopropyl)-3-ethylcarbodiimide (1.6 g, 8.4 mmol), 4-dimethylaminopyridine (0.85 g, 7 mmol) and ethyl 3-aminobenzoate (1.27 g, 7.7 mmol) were stirred in tetrahydrofuran (43 mL) at room temperature overnight. On next day the reaction was diluted with ethyl acetate and water, extracted with ethyl acetate (3×), dried over magnesium sulfate and concentrated. The crude material was purified on silica gel using 3:1 hexane:ethyl acetate to give the product (3.4 g, 85%, TLC=0.3 Rf in 3:1 hexane:ethyl acetate).

Step 6: Ethyl 3-(2-(5-Benzyloxy)indolinyl) methylthioacetamidobenzoate

To the indoline (3.4 g, 5.9 mmol) of step 5, trifluoroacetic acid (24 mL) was added and the reaction stirred for 1 hour at 0° C. The reaction was quenched by the addition of water and the TFA neutralized by the addition of sodium bicarbonate, the aqueous layer was extracted with ethyl acetate (3×), dried over magnesium sulfate and concentrated. The crude material was purified on silica gel using 2:1 hexane:ethyl acetate to yield product (2.7 g, 96%, TLC=0.3 Rf in 2:1 hexane:ethyl acetate).

Step 7: Ethyl 3-(2-(5-Benzyloxy-1-(2,4-bis(1,1-dimethyl) propyl)phenoxyacetyl)indolinyl) methylthioacetamidobenzoate The 2,4-bis(1,1-dimethylpropyl)phenoxyacetic acid (0.228 g, 0.78 mmol) was dissolved in dichloromethane (2 mL), to which oxalyl chloride (0.14 mL 1.6 mmol) was added followed by dimethyl formamide (0.1 mL) at room temperature. After one hour the reaction is concentrated and azeotroped with toluene and left on the high vacuum for two hours. The indoline ester (0.308 g, 0.65 mmol), prepared in step 6, and 4-dimethylaminopyridine (0.008 g, 0.066 mmol) were dissolved in dichloromethane (1.2 mL) and then the above prepared acid chloride in dichloromethane (0.5 mL) was added followed by the addition of triethylamine (0.28 mL, 1.95 mmol). The reaction was stirred at room temperature overnight, and then diluted with ethyl acetate and water, extracted with ethyl acetate (3×), dried over magnesium sulfate and concentrated. The crude material was 5 purified on silica gel using 2:1 hexane:ethyl acetate to yield product (0.291 g, 60%, TLC=0.4 Rf in 2:1 hexane:ethyl acetate).

Step 8:

The ester (0.231 g, 0.31 mmol) of step 7 was dissolved in THF (4.3 mL), methanol (4.3 mL) and than 1N NaOH (3.2 mL) was added. The reaction mixture was stirred at room temperature overnight at which time it was concenterated, diluted with water, acidified to pH 5 with 10% HCl and extracted with ethyl acetate (3×), the organic extracts were dried over magnesium sulfate and concentrated to give the titled product (0.207 g, 93.2%, TLC=0.3 Rf in 2:1 hexane:ethyl acetate with 1.5% acetic acid).

EXAMPLE 18

3-(2-(-5-Benzyloxy-1-(2,4-bis(1,1-dimethy)propyl) phenoxyacetyl)indolinyl)methylthioacetamido-4-methylbenzoic Acid Step 1: Ethyl 2-(5-Benzyloxy)indolinylmethylthioacetate The N-tert-butoxycarbonyl indoline (3.0 g, 6.6 mmol), prepared in step 3 of Example 17, was added to a flask and cooled to 0° C. To this reaction mixture trifluoroacetic acid was added (35 mL) and the reaction was stired for 1 hour at 0° C. and then 1 hour at rt. The reaction was quenched by the addition of water, and the TFA was neutralized by the addition of solid sodium bicarbonate, the aqueous layer was extracted with ethyl acetate (4×) and dried over magnesium sulfate and concentrated to an orange oil (1.85 g, 79%) that was used directly for the next step.

Step 2: Ethyl 2-(5-Benzyloxy-1-(2,4-bis(1,1-dimethy) propyl)phenoxyacetyl)-indolinylmethylthioacetate 2,4-Bis(1,1-dimethy)propyl)phenoxyacetic acid (2.0 g, 6.8 mmol), dichloromethane (15 mL), oxalyl chloride (1.2 mL, 13.6 mmol), dimethylformamide (0.1 mL) were stirred at 0° C. for 45 minutes at which time the reaction is concentrated and azeotroped with toluene (1×) and concentrated on the high vac for 2 hours before use. The indoline ester (1.85 g, 5.2 mmol), prepared in step 1, and 4-dimethylaminopyridine (0.08 g) were dissolved in dichloromethane (15 mL) and then the above generated acid chloride in dichloromethane (5 mL) was added followed by the addition of triethylamine (0.95 mL, 6.8 mmol). The reaction was stirred 16 hours at rt, worked up and concentrated (4.0 g, orange oil), chromatographed using a 9:1 to 6:1 gradient of hexane:ethyl acetate to yield the product (2.5 g, 75%) that was used for the next step without further purification.

Step 3: 2-(5-Benzyloxy-1-(2,4-bis(1,1-dimethy)propyl) phenoxyacetyl)indolinylmethylthioacetic Acid The ester (2.5 g, 3.9 mmol), prepared in step 2, was dissolved in THF (20 mL), methanol (6 mL) and then 1N sodium hydroxide (12 mL) was added. The resulting mixture was stirred 24 hours at which time it was concentrated, diluted with water, acidified to pH 4 with concentrated HCl and extracted with ethyl acetate (4×), the organic extracts were dried over magnesium sulfate, concentrated, and purified via chromatography (3:1 hexane:ethyl acetate with 1% acetic acid) to yield 1.17 g (50%) of the product as white solid.

Step 4: Methyl 3-(2-(5-Benzyloxy-1-(2,4-bis(1,1-dimethy) propyl)phenoxyacetyl)indolinyl)methylthioacetamido-4-methylbenzoate The acid (0.20 g, 0.33 mmol), prepared in step 3, EDCI (0.08 g, 0.43 mmol), DMAP (4 mg, 0.03 mmol) and methyl 3-amino-4-hydroxy benzoate (0.06 g, 0.33 mmol) were dissolved in THF (3 mL) and refluxed 16 hours. Aqueous workup with ammonium chloride and ethyl acetate and purification via silica gel chromatography (hexane:ethyl acetate 3:1) yielded 0.13 g (52%) of the product as a white solid.

Step 5:

The titled compound was prepared from ester, prepared in step 4, according to the procedure described in step 3.

EXAMPLE 17 TO 36 IN TABLE 2 WERE PREPARED ACCORDING TO THE PROCEDURE DESCRIBED IN EITHER EXAMPLE 17 OR EXAMPLE 18

EXAMPLE 37

2-(5-Benzyloxy-1-(3,5-bis(trifluoromethyl) phenoxyacetyl)indolinyl)methylthioacetic Acid Step 1: 2-(5-Benzyloxy-1-(3,5-bis(trifluoromethyl) phenoxyacetyl)indolinyl)methanol A 1-L oven-dried round bottom flask fitted with a magnetic stirring bar and equalizing dropping funnel was charged with 17.0 g (59 mmol) of 3,5-bis(trifluoromethyl) phenoxyacetic aci, DMF (5 drops) and anhydrous $CH_2Cl_2$ (300 mL). Oxalyl chloride (23 mL, 263 mmol) was added dropwise over 10 min. After stirring for 2.5 h at room temperature solvent, excess oxalyl chloride were removed in vacuo to afford acid chloride as a white solid. This was used immediately in the next reaction.

A 1-L oven-dried round bottom flask fitted with a magnetic stirring bar and equalizing dropping funnel was charged with 15.3 g (60 mmol) of 2-(5-Benzyloxy) indolinylmethanol, prepared in step 1 of Example 17, DMAP (0.73 g, 6 mmol) and anhydrous $CH_2Cl_2$ (300 mL). After cooling to 0° C., a solution of above prepared acid chloride (59 mmol) in anhydrous $CH_2Cl_2$ (100 mL) was added dropwise, followed by $NEt_3$ (9 mL, 64.7 mmol). After stirring for 1 h at 0° C. the reaction mixture was washed with saturated $NaHCO_3$ solution (100 mL), 1 N HCl solution (100 mL) and $H_2O$ (100 mL), dried over $Na_2SO_4$ and filtered. The solvent was removed in vacuo. Purification by column chromatography in silica gel using 25–40% AcOEt in hexane afforded product as a light yellow solid. Yield 22.0 g (71%).

Step 2: Ethyl 2-(5-Benzyloxy-1-(3,5-bis(trifluoromethyl) phenoxyacetyl)indolinyl)methylthioacetate A 500-mL oven-dried round bottom flask fitted with a magnetic stirring bar was charged with alcohol (19.0 g, 36.15 mmol), prepared in step 1, anhydrous $CH_2Cl_2$ (300 mL), and $NEt_3$ (7.5 mL, 54.23 mmol). MsCl was added dropwise over 2 min and the reaction mixture was stirred at room temperature for 10 min. The solution was diluted with $CH_2Cl_2$ (500 mL) and washed with 1N HCl solution (100 mL) and saturated $NaHC_3$ solution (100 mL). The $CH_2Cl_2$ solution was dried over $Na_2SO_4$ and filtered. The solvent was removed and the mesylate was used in the next step without further purification.

A 500-mL oven-dried round bottom flask fitted with a magnetic stirring bar was charged with ethyl thioacetate (4.2 mL, 38.5 mmol), and anhydrous THF (75 mL). After cooling in a dry ice/acetone bath $NaN(SiMe_3)_2$ (1 M solution in THF, 50 mL, 50 mmol) was added. After 15 min a solution of above prepared mesylate (21 g, 35 mmol) in anhydrous THF (60 mL) was added. After 15 min the reaction mixture was allowed to warm to room temperature. After stirring at room temperature for 100 min the reaction was heated at reflux for 4 h. The solution was allowed to cool to room temperature. It was diluted with $CHCl_3$ (500 mL), washed with saturated $Na_2CO_3$ solution (200 mL) and 1N HCl solution (200 mL). The organic solution was dried over $Na_2SO_4$ and filtered. The solvent was removed in vacuo. The crude material was purified by column chromatography on silica gel using 15% AcOEt in hexane to afford 13.8 g (63%) of product.

Step 3:

A 250-mL round bottom flask fitted with a magnetic stirring bar was charged with ester (12.45 g, 19.8 mmol), prepared in step 2, THF (100 mL), MeOH (33 mL) and $H_2O$ (33 mL). $LiOH.H_2O$ (1.08 g, 25.7 mmol) was added and the reaction mixture was stirred at room temperature for 3 h. The solvents were removed in vacuo. The residue was taken into 1N HCl solution (200 mL) and extracted with AcOEt (2×400 mL). The combined extracts were washed with 1 N HCl solution (100 mL), dried over $Na_2SO_4$ and filtered. The solvent was removed in vacuo to afford the titled compound. Yield 11.9 g (100%).

EXAMPLE 38

5-(2-(-5-Benzyloxy-1-(3,5-bis(trifluoromethyl) phenoxyacetyl)indolinyl)methylthioacetamido) benzene-1,3-dicarboxylic Acid Step 1: 5-(2-(-5-Benzyloxy-1-(3,5-bis(trifluoromethyl) phenoxyacetyl)indolinyl)methylthioacetamido)benzene-1, 3-dicarboxylate A 100-mL oven-dried round bottom flask fitted with a magnetic stirring bar was charged with acid (1.2 g, 2 mmol), prepared in step 3 of Example 37, anhydrous THF (40 mL), EDCI (0.544 g, 2.8 mmol), DMAP (0.024 g, 0.2 mmol), and 5-amino-1,3-benzenedicarboxylic acid (0.46 g, 2.2 mml). The reaction mixture was heated at reflux until no change was detected by TLC. The solvent was removed in vacuo. The residue was dissolved in $CH_2Cl_2$ (200 mL), washed with 1 N HCl solution (25 mL), dried over $Na_2SO_4$ and filtered. The solvent was removed in vacuo. The crude material was purified by column chromatography on silica gel using 1–2% MeOH in $CH_2Cl_2$ to afford 1.2 g (77%) of product.

Step 2:

A 25-mL round bottom flask fitted with a magnetic stirring bar was charged with ester (0.6 g, 0.76 mmol), prepared in step 1, THF (7.5 mL), MeOH (2.5 mL) and H2O (2.5 mL). LiOH.H$_2$O (0.084 g, 2 mmol) was added, and the reaction mixture was stirred at room temperature for 6 h. The solvents were removed in vacuo. The residue was taken into 1N HCl solution (10 mL) and extracted with AcOEt (2×50 mL). The combined extracts were dried over Na2SO4 and filtered and removed in vacuo. The crude material was purified by column chromatography on silica gel (eluant: 5% MeOH in CHCl3+0.5–0.7% AcOH) to yield 0.28 g (46%) of the titled compound.

EXAMPLES 39, 40, 43 IN TABLE 3 WERE PREPARED ACCORDING TO THE PROCEDURE DESCRIBED IN EITHER EXAMPLE 38

EXAMPLE 41

5-(2-(-5-Benzyloxy-1-(3,5-bis(trifluoromethyl) phenoxyacetyl)indolinyl)methylthioacetamido)-3-hydroxymethylbenzoic Acid Step 1: Methyl 5-(2-(-5-benzyloxy-1-(3,5-bis (trifluoromethyl)phenoxyacetyl)indolinyl) methylthioacetamido)-3-tert-butyldimethylsilyloxymethylbenzoate This compound was prepared according to the procedure described in step 1 of Example 38.

Step 2: Methyl 5-(2-(-5-Benzyloxy-1-(3,5-bis (trifluoromethyl)phenoxyacetyl)indolinyl) methylthioacetamido)-3-hydroxymethylbenzoate A 25-mL oven-dried round bottom flask fitted with a magnetic stirring bar was charged with silyl propected ester (1.32 g, 1.5 mmol), prepared in step 1, anhydrous THF (10 mL), and TBAF (1 M solution in THF, 2.5 mol equiv.). The reaction mixture was stirred at room temperature for 3 hours. The solvent was removed in vacuo. The oily residue was purified by column chromatography on silica gel using 0–30% AcOEt in CH$_2$Cl$_2$ to afford 0.94 g (92%) of desired product.

Step 3:

The titled compound was prepared according to the procedure described in step 2 of Example 38.

EXAMPLE 42 IN TABLE 3 WAS PREPARED ACCORDING TO THE PROCEDURES DESCRIBED IN EXAMPLE 41

EXAMPLE 44

5-(2-(-5-Hydroxy-1-(3,5-bis(trifluoromethyl) phenoxyacetyl)indolinyl)methylthioacetamido) benzene-1,3-dicarboxylic Acid Step 1: 2-(5-Hydroxy-1-(3,5-bis(trifluoromethyl) phenoxyacetyl)indolinyl)methanol A 500-mL Parr Hydrogenation bottle was charged with 2-(5-Benzyloxy-1-(3,5-bis(trifluoromethyl)phenoxyacetyl) indolinyl)methanol (10 g, 19.1 mmol), prepared in step 1 of Example 37, 5% Pd on carbon (1.0 g), AcOEt (150 mL) and MeOH (100 mL) and subsequently hydrogenated at 50 psi for 18 h. The reaction mixture was filtered through Celite and concentrated in vacuo to afford crude product. This was used in the next step reaction without further purification.

Step 2: 2-(5-(4-Methoxy)benzyloxy-1-(3,5-bis (trifluoromethyl)phenoxyacetyl)indolinyl)methanol A 1-L oven-dried round bottom flask fitted with a magnetic stirring bar and reflux condenser was charged with alcohol (8.56 g, 19.7 mmol), prepared in step 1, 200 mesh K$_2$CO$_3$ (6.53 g, 47.2 mmol), KI (3.91 g, 23.6 mmol) and finally the p-methoxy benzyl chloride (3.2 mL, 23.6 mmol) in 450 mL of anhydrous acetonitrile. The reaction mixture was heated at reflux for 4 h. The reaction mixture was partitioned between AcOEt (500 mL) and H$_2$O (200 mL). The aqueous layer was extracted with AcOEt(3×500 mL). The combined AcOEt extracts were washed with brine (500 mL), dried over Na$_2$SO$_4$ and filtered. The solvents were removed in vacuo. Purification of the residue by column chromatography on silica gel (eluant: 40% AcOEt in hexane) afforded desired product. Yield 8.7 g (83%).

Step 3: Methyl 5-(2-(-5-(4-Methoxy)benzyloxy-1-(3,5-bis (trifluoromethyl)phenoxyacetyl)indolinyl) methylthioacetamido)benzene-1,3-dicarboxylate A 100-mL oven-dried round bottom flask fitted with a magnetic stirring bar was charged with alcohol (3.2 g, 5.77 mmol), prepared in step 2, and anhydrous CH$_2$Cl$_2$ (44 mL). The reaction mixture was cooled to 0° C. and added anhydrous Et$_3$N (1.2 mL, 8.61 mmol) followed by MsCl (0.53 mL, 6.84 mmol). The reaction mixture was stirred at 0° C. for 5 min. The reaction mixture was partitioned between CH$_2$Cl$_2$ (100 mL) and H$_2$O (50 mL). The aqueous layer was extracted with CH$_2$Cl$_2$ (3×100 mL). The combined CH$_2$Cl$_2$ extracts were washed with 1 N HCl solution (100 mL), saturated NaHCO$_3$ solution (100 mL), H$_2$O (100 mL), brine (100 mL), dried over Na$_2$SO$_4$ and filtered. The solvents were removed in vacuo to afford mesylate. This was used in the next step reaction without further purification.

A 100-mL oven-dried round bottom flask fitted with a magnetic stirring bar and reflux condenser was charged with above prepared mesylate (3.60 g, 5.70 mmol), anhydrous Cs$_2$CO$_3$ (5.19 g, 15.9 mmol) and anhydrous DMF (20 mL). The reaction solution was passed through N$_2$ for 15 min. Methyl 5-thioacetamido-1,3-benzenedicarboxylate, prepared in Intermediate 2, was added in one portion and the reaction mixture was heated at 50° C. for 18 h. The reaction mixture was partitioned between AcOEt (500 mL) and H$_2$O (200 mL). The aqueous layer was extracted with AcOEt(3× 100 mL). The combined AcOEt extracts were washed with saturated Na$_2$CO$_3$ solution (100 mL), H$_2$O (100 mL), brine (500 mL), dried over Na$_2$SO$_4$ and filtered. The solvents were removed in vacuo. Purification of the residue by column chromatography on silica gel (eluant: 5% AcOEt in CH$_2$Cl$_2$) afforded product. Yield 2.5 g (53%).

Step 4: Methyl 5-(2-(-5-Hydroxy-1-(3,5-bis (trifluoromethyl)phenoxyacetyl)indolinyl) methylthioacetamido)benzene-1,3-dicarboxylate A 100-mL oven-dried round bottom flask fitted with a magnetic stirring bar was charged with ester (2.60 g, 3.17 mmol), prepared in step 3, and anhydrous CH$_2$Cl$_2$ (30 mL). To the reaction mixture was added TFA (25 mL) in several portions over 1 min. The reaction mixture was poured onto 500 mL saturated NaHCO$_3$ solution and extracted with CH$_2$Cl$_2$ (3×100 mL). The combined CH$_2$Cl$_2$ extracts were washed with saturated Na$_2$CO$_3$ solution (200 mL), H$_2$O (200 mL), brine (500 mL), dried over Na$_2$SO$_4$ and filtered. The solvents were removed in vacuo. Purification of the residue by column chromatography on silica gel (eluant: 12.5%–20% AcOEt in CH$_2$Cl$_2$) afforded the product. Yield 1.5 g (68%).

Step 5:

A 25-mL round bottom flask fitted with a magnetic stirring bar was charged with ester (270 mg, 0.40 mmol), prepared in step 4, LiOH hydrate (3.3 equiv.), THF (3.6 mL), MeOH (1.2 mL) and H$_2$O (1.2 mL). The reaction mixture was heterogeneous with white solid suspended in the solution. After stirring for 4 h, more solvents were added in 3:1:1=THF: MeOH: H$_2$O to make a clear solution. The reaction mixture was stirred at room temperature for 18 h and monitored by TLC. The reaction mixture was acidified with 1 N HCl solution to pH=2 or with acetic acid to pH=4 and then partitioned between AcOEt (20 mL) and H$_2$O (20 mL). The aqueous layer was extracted with AcOEt(3×20 mL). The combined AcOEt extracts were washed with H$_2$O (20 mL), brine (20 mL), dried over Na$_2$SO$_4$ and filtered. The solvents were removed in vacuo. Purification of the residue by column chromatography on silica gel followed by recrystallization from acetone/hexane afforded 130 mg of the titled compound (50%).

EXAMPLE 45

5-(2-(5-(3,5-Dibromo)benzyloxy-1-(3,5-bis (trifluoromethyl)phenoxyacetyl)indolinyl) methylthioacetamido)benzene-1,3-dicarboxylic Acid Step 1: Methyl 5-(2-(5-(3,5-Dibromo)benzyloxy-1-(3,5-bis (trifluoromethyl)phenoxyacetyl)indolinyl) methylthioacetamido)benzene-1,3-dicarboxylate A 25-mL oven-dried round bottom flask fitted with a magnetic stirring bar and reflux condenser was charged with methyl 5-(2-(-5-Hydroxy-1-(3,5-bis(trifluoromethyl) phenoxyacetyl)indolinyl)methylthioacetamido)benzene-1, 3-dicarboxylate (0.19 g, 0.27 mmol), prepared in step 4 of Example 4, 200 mesh K$_2$CO$_3$ (2.4 equiv.) and 3,5-dibromobenzyl bromide (1.2 equiv.) in 7.5 mL of anhydrous acetonitrile. The reaction mixture was heated at 70° C. for 2 h. The reaction mixture was partitioned between AcOEt (30 mL) and H$_2$O (20 mL). The aqueous layer was extracted with AcOEt(3×30 mL). The combined AcOEt extracts were washed with brine (50 mL), dried over Na$_2$SO$_4$ and filtered. The solvents were removed in vacuo. Purification of the residue by column chromatography on silica gel using 15% EtOAc in dichloromethane afforded 0.20 g of the product (77%).
Step 2:
The titled compound was prepared from the ester, prepared in step 1, according to the procedure described in step 5 of Example 44.

EXAMPLES 46 to 50 IN TABLE 4 WERE PREPARED ACCORDING TO THE PPROCEDURE DESCRIBED IN EXAMPLE 44, BUT USING CORRESPONDING ALKYLATING REAGENT

EXAMPLE 51

Methyl 3-(2-(5-Benzyloxy-1-(4-benzylbenzoyl) indolinyl)methylthioacetamido)benzoate 4-Benzylbenzoic acid (0.19 g, 0.91 mmol) was dissolved in dichloromethane (2.3 ml), next oxalyl chloride (0.16 mL, 1.82 mmol) was added followed by dimethylformamide (0.5 mL) at room temperature. After one hour the reaction was concentrated and azeotroped with toluene and left on high vaccum for two hours.

Ethyl 3-(2-(5-benzyloxy)indolinyl) methylthioacetamidobenzoate (0.308 g, 0.65 mmol), prepared in step 6 of Example 17, and 4-dimethylaminopyridine (8 mg, 0.066 mmol) were dissolved in dichloromethane (1.2 mL) and then the above prepared acid chloride in dichloromethane (0.5 mL) was added followed by the addition of triethylamine (0.28 mL, 1.95 mmol). The reaction was stirred at room temperature overnight. The reaction was diluted with ethyl acetate and water, extracted with ethyl acetate (3×), dried over magnesium sulfate and concentrated. The crude material was purified on silica gel using 2:1 hexane:ethyl acetate to yield 0.354 g of the titled product (81.7%, TLC=0.4 Rf in 2:1 hexane:ethyl acetate).

EXAMPLE 52

3-(2-(5-Benzyloxy-1-(4-benzylbenzoyl)indolinyl) methylthioacetamido)benzoic Acid The ester (0.354 g, 0.53 mmol), prepared in Example 51, was dissolved in THF (5.6 mL), methanol (5.6 mL) and than 1N NaOH (4.2 mL) was added. The reaction mixture was stirred at room temperature overnight at which time it was concentrated, diluted with water, acidified to pH 5 with10% HCl and extracted with ethyl acetate (3×). The organic extracts were dried over magnesium sulfate and concentrated to give the titled product (0.32 g, 94.4%, TLC=0.3 Rf in 2:1hexane:ethyl acetate with 1.5% acetic acid).

EXAMPLES 53 TO 58 IN TABLE 5 WERE PREPARED ACCORDING TO THE PROCEDURES DESCRIBED IN EXAMPLES 51 AND 52

EXAMPLE 59

3-(2-(5-Benzyloxy-1-(2-naphthoxyaceiyl)indolinyl) methylthioacetamido)4-methoxybenzoic Acid Step 1: Methyl 3-(2-(5-Benzyloxyindolinyl) methylthioacetamido)4-methoxybenzoate This compound was prepared according to the procedures described in step 6 of Example 17, but with methyl 4-methoxybenzoate.
Step 2: Methyl 3-(2-(5-Benzyloxy-1-(2-naphthoxyacetyl) indolinyl)methylthioacetamido)4-methoxybenzoate The indole ester (0.22 g, 0.45 mmol), prepared in step 1, 2-naphthoxyacetic acid (0.11 g, 0.53 mmol), EDCI (0.10 g, 0.53 mmol) and DMAP (5 mg, 0.04 mmol) were weighed into a flask that was equipped with a condenser, flushed with nitrogen, and then tetrahydrofuran (5 mL) was added and the reaction was brought to reflux for 18 hours; the reaction was diluted with 1/2 saturated ammonium chloride and ethyl acetate, extracted 3× with ethyl acetate, dried over magnesium sulfate, concentrated to yield (0.30 g, 100% crude) a white solid that was used without purification.
Step 3:
The ester (0.12 g, 0.20 mmol), prepared in step 2, was dissolved in THF/methanol and then 1N sodium hydroxide (0.8 mL) was added and the resulting mixture was stirred 16 hours at RT and a further 5 hours at 45° C., workup yielded 0.12 g of a yellow solid that was purified via preparative TLC (1:1 hexane:ethyl acetate with 1% acetic acid) to yield 0.12 g of the titled product (95%).

EXAMPLES 60 TO 63 IN TABLE 5 WERE PREPARED ACCORDING TO THE PROCEDURES DESCRIBED EITHER IN EXAMPLE 59 OR IN EXAMPLES 51 AND 52

EXAMPLE 64

3-(2-(5-Benzyloxy-1-tert-butoxycarbonyl)indolinyl) methylsulfonylacetamidobenzoic Acid Step 1: Ethyl 3-(2-(5-Benzyloxy-1-tert-butoxycarbonyl) indolinyl)methylsulfonylacetamidobenzoate To a solution of Ethyl 3-(2-(5-benzyloxy-1-tert-butoxycarbonyl)indolinyl)methy lthioacetamidobenzoate (0.05 g, 0.09 mmol), prepared in step 5 of Example 17, in dichloromethane (0.1 mL) at room temperature, m-chloroperbenzoic acid (0.06 g of 60% m-cPBA, 0.21 mmol) was added and the reaction stirred overnight. Next day the reaction was quenched with an aqueous solution of sodium bicarbonate, extracted with ethyl acetate (3×), dried over magnesium sulfate and concentrated. The crude sulfone (0.52 g, 98%, TLC=0.3 Rf in 1:1 hexane:ethyl acetate) was used for the next reaction directly.
Step 2:
The titled compound was prepared according to the procedure described in step 3 of Example 59.

EXAMPLES 66 AND 65 WERE PREPARED ACCORDING TO THE PROCEDURES DESCRIBED IN EXAMPLE 18

EXAMPLE 67

2-(2-(-5-Benzyloxy-1-(2,4-bis(1,1-dimethy)propyl) phenoxyacetyl)indolinyl)methylthiobenzoic Acid Step 1: 5-Benzyloxy-1-(2,4-bis(1,1-dimethy)propyl) phenoxyacetyl)-2-hydroxymethyiindoline The diisopropylethylamine (3.5 mL, 20.5 mmol), DMAP (0.25 g, 2.05 mmol) and the indoline alcohol (4.53 g, 17.7 mmol), prepared in step 1 of Example 17, were weighed into a flask which was flushed with nitrogen and cooled to 0° C. at which time a 0° C. solution of di-tert-amylphenoxyacetyl chloride (20.5 mmol) in $CH_2Cl_2$ (50 mL) was added via cannula. The resulting solution was left to warm to room temperature overnight and then quenched by the addition of 1/2 saturated ammonium chloride and $CH_2Cl_2$, the solution was extracted with $CH_2Cl_2$ (3×), the combined layers were dried over magnesium sulfate and concentrated to yield (10.4 g) of a yellow foam that was purified via chromatography using a gradient (hexane:ethyl acetate 7:1 to 3:1 to 1:1) to yield 3.62 g of the product.

Step 2: 2-(5-Benzyloxy-1-(2,4-bis(1,1-dimethy)propyl) phenoxyacetyl)indolinyimethylmethyisulfonate To a solution of alcohol (1.2 g, 2.26 mmol) in $CH_2Cl_2$ (15 mL), prepared in step 1, is added triethylamine (0.44 mL, 3.16 mmol). The solution is brought to −50° C. and then mesyl chloride (0.23 mL, 2.93 mmol) is added. The mixture is stirred 2 h at −50° C., quenched with saturated ammonium chloride and allowed to come to rt. The mixture is taken up in $CHCl_3$ (50 mL), washed with saturated sodium bicarbonate (1×10 mL), brine (1×10 mL), dried (MgSO4), filtered and concentrated to afford the product (1.19 g, 86%).

Step 3: Methyl 2-(2-(-5-Benzyloxy-1-(2,4-bis(1,1-dimethy) propyl)phenoxyacetyl)indolinyt)methylthiobenzoate To a solution of mesylate (0.54 g, 0.89 mmol), prepared in step 2, in degassed DMF (2 mL) is added $CsCO_3$ (0.724 g, 2.22 mmol) and methyl thiosalicylate (0.134 mL, 0.98 mmol). The mixture is stirred 4 h, taken up in ethyl acetate (20 mL), washed with brine (3×3 mL), dried ($MgSO_4$), filtered and concentrated. Chromatography (gradient, hexane:ethyl acetate 15:1 to 4:1) afforded 0.53 (86%) of the title compound as a yellow oil.

Step 4:
The titled compound was prepared according to the procedure described in step 3 of Example 59.

EXAMPLE 68 WAS PREPARED ACCORDING TO THE PROCEDURES DESCRIBED IN EXAMPLE 67

EXAMPLE 69

3-(N-(2-(-5-Benzyloxy-1-(2,4-bis(1,1-dimethy) propyl)phenoxyacetyl)indolinyl)methylthioethyl) aminobenzoic Acid The titled product was prepared according to the procedures described in step 3 of Example 59, but using Intermediate 15.

EXAMPLE 70

3-N-Methyl-(2-(-5-benzyloxy-1-(2,4-bis(1,1-dimethy)propyl)phenoxyacetyl)indolinyl) methylthioacetamido-4-methoxybenzoic Acid An oven-dried 100 mL, 3-neck round bottom flask, equipped with a stir bar and nitrogen inlet, was charged with methyl 3-(2-(-5-Benzyloxy-1-(2,4-bis(1,1-dimethy)propyl)-phenoxyacetyl)indolinyl)methylthioacetamido4-methoxybenzate (581 mg, 0.757 mmol), prepared in the synthesis of Example 20 using the procedures described in Example 18, and 10 mL of THF was added via syringe. To the resulting yelllow solution was added NaH (60% suspension in mineral oil, 39 mg, 0.975 mmol). The reaction mixture was stirred at 25° C. for 1.5 h to afford a pale suspension. Methyl iodide (161 mg, 1.14 mmol) was added, and the reaction mixture was stirred at 25° C. for 2 days. After chilling to 0° C., water was added (10 mL), followed by 50 mL of half saturated ammonium chloride, and 100 mL of EtOAc. The layers were separated, and the aqueous phase was extracted once with EtOAc (50 mL). The combined organic phases were dried (sodium sulfate), filtered, and concentrated to afford 0.6 g of crude product as an orange oil. This material was dissolved in 15 mL of THF and 10 mL of methanol, and 7 mL of 1N NaOH solution was added, under nitrogen. After being stirred for 2 h at 25° C., the reaction mixture was concentrated to dryness on the rotary, and 100 mL of 1N HCl, and 100 mL of EtOAc were added. The layers were separated, and the organic phase was dried (magnesium sulfate), filtered, and concentrated. The crude material obtained (0.565 g) was purified by column chromatography on silica gel (eluant: chloroform to 3% MeOH in chloroform) to afford the titled compound (0.415 g, 70% yield).

EXAMPLE 71 WAS PREPARED ACCORDING TO THE PROCEDURES DESCRIBED IN EXAMPLE 70, BUT USING ALLYL BROMIDE

EXAMPLE 72

3-(2-(5-Benzyloxy-1-(2-(4-pyridinyly)ethyl) indolinyly)methylthioacetamidobenzoic Acid Step 1: Ethyl 3-(2-(5-Benzyloxy-1-(2-(4-pyridinyl)ethyl) indolinyl)methylthioacetamidobenzoate To a solution of ethyl 3-(2-(5-benzyloxy)indolinyl) methylthioacetarnidobenzoate (0.30 g, 0.63 mmol), prepared in step 6 of Example 17, in dichloromethane (3.0 mL) and acetic acid (2.0 mL), 4-vinylpyridine (0.08 mL, 0.75 mmol) was added. The reaction was stirred at room temperature overnight. The reaction was quenched with half saturated sodium bicarbonate, extracted with ethyl acetate (3×), dried over magnesium sulfate and concentrated. The crude material was purified on silica gel using a gradient of 2:1 hexane:ethyl acetate to 100% ethyl acetate to yield 0.023 g of product (25%, TLC=0.7 Rf in ethyl acetate).

Step 2:
The titled compound was prepared according to the procedure described in step 3 of Example 59.

EXAMPLE 73

3-(2-(5-Benzyloxy-1-(2-naphthyl)methy)indolinyl) methylthioacetamidobenzoic Acid Step 1: Ethyl 3-(2-(5-Benzyloxy-1-(2-naphthyl)methy) indolinyl)methylthioacetamidobenzoate A mixture of 3-(2-(5-benzyloxy)indolinyl) methylthioacetamidobenzoate (0.2 g, 0.42 mmol), prepared in step 6 of Example 17, 2-(bromomethyl)naphthalene (0.1 g, 0.42 mmol) and potassium carbonate (0.17 g, 1.26 mmol) in N,N-dimethylformamide (2 mL) was stirred at room temperature overnight. Next the reaction was diluted with ethyl acetate and water, extracted with ethyl acetate (3×), dried over magnesium sulfate and concentrated. The crude material was purified on silica gel using 2:1 hexane:ethyl acetate to yield 0.22 g of product (85%, TLC=0.5 Rf in 2:1 hexane:ethyl acetate).

Step 2:

The titled compound was prepared according to the procedure described in step 3 of Example 59.

EXAMPLES 74 AND 75 IN TABLE 6 WERE PREPARED ACCORDING TO THE PROCEDURES DESCRIBED IN EXAMPLE 73

EXAMPLE 76

2-(2-(-5-Benzyloxy-1-(2-naphthyflmethyl)indolinyl) methylthiobenzoic Acid

Step 1: 2-(2-(-5-Benzyloxy-1-(1,1-dimethyl) ethoxycarbonyl)indolinyl)methylmethylsulfonate tert-Butyl 1-(5-benzyloxy-2-hydroxymethy) lindolinylformate (6.72 g, 19 mmol), prepared in step 2 of Example 17, was dissolved in $CH_2Cl_2$ (80 mL, dried over $MgSO_4$ before use). The clear yellow solution was cooled in a dry-ice bath. $Et_3N$ (4.0 mL) was then added followed by methanesulfonyl chloride (2.0 mL). The reaction mixture was stirred for 2 h at −40° C. then quenched with $H_2O$. It was washed with satuarated $NaHCO_3$ (300 mL) and the aqueous layer extracted twice with $CH_2Cl_2$. The combined $CH_2Cl_2$ layers were dried over $MgSO_4$, filtered and evaporated to dryness to give the product (7.30 g, 89.1% yield), which was used for the next reaction directly.

Step 2: Methyl 2-(2-(5-Benzyloxy-1-(1,1-dimethyl) ethoxycarbonyl)indoinyl)methylthiobenzoate Mesylate (7.2 g, 1.8 mmol), prepared in step 1, was dissolved in DMF (50 mL). The clear light brown solution was degassed by vigorously bubbling with Ar for 30 min. Cesium carbonate (13.8 g) was added followed by methyl thiosalicylate (2.4 mL). The solution changed to a bright yellow and the suspension was stirred overnight. Methyl thiosalicylate (0.15 mL) was added to complete the reaction and the mixture was stirred overnight. The reaction was then quenched by the addition of saturated $NaHCO_3$ (400 mL). The mixture was extracted with $CH_2Cl_2$ (3×) and the combined $CH_2Cl_2$ solution was back-washed with $H_2O$ (200 mL). The organic layer was dried over $MgSO_4$, filtered and evaporated to dryness to give the product (9.71 g, 99%).

Step 3. Methyl 2-(2-(5-Benzyloxy)indolinyl) methylthiobenzoate

Ethyl acetate (75 mL, dried over MgSO4 before use) was charged in a 500 mL round bottom flask. HCl gas was bubbled through and the EtOAc/HCl solution was cooled in an ice bath. Methyl ester (8.4 g), prepared in step 2, was dissolved in EtOAc (25 mL, dried over MgSO4 before use). This solution was transferred to the HCl/EtOAc solution by syringe. The solution turned to red and was stirred in an ice bath. A white precipitate appeared in 1 h and the solution was stirred overnight to complete the reaction. The solid was collected by filtration, washed with dry EtOAc, suspended in saturated $NaHCO_3$ (175 mL) and stirred with EtOAc (400 mL). The milky emulsion gradually dissolved and the mixture changed to a clear solution. The layers were separated and the aqueous laver was extracted (2×) with EtOAC, while the combined EtOAC layers were dried over MgSO4, filtered and evaporated to dryness to give the product (6.06 g, 90% yield).

Step 4: Methyl 2-(2-(5-Benzyloxy-1-(4-benzyl)benzyl) indolinyl)methylthiobenzoate In a 50 mL round bottom flask, ester (1 g), prepared in step 3, was dissolved in DMF (6 mL). p-Benzylbenzyl bromide was added (1 eq) followed by $K_2CO_3$ (1 eq). The reaction mixture was stirred overnight at room temperature. To complete the reaction additional p-benzylbenzyl bromide (0.5 eq) was added and the reaction was stirred for another 2 hours. After its completion, the reaction was diluted with $H_2O$ and extracted with EtOAc (2×). The organic layers were combined and dried over $MgSO_4$. The $MgSO_4$ was filtered and the solvent was evaporated to give an oily material which was dried overnight on high vacuum to give the product (1.59 g, 109% yield).

Step 5:

The ester (1.52 g), prepared in step 4, was dissolved in THF (10 mL) in a 50 mL round bottom flask. To it was added NaOH (1 eq, 2N) followed by MeOH (3 mL) and the reaction mixture was stirred overnight. Additional NaOH (0.3 eq) was added to complete the reaction and the mixture was stirred throughout the weekend. Then it was acidified and diluted with $H_2O$ and extracted with EtOAc (2×). The organic layers were combined and dried over $MgSO_4$. The $MgSO_4$ was filtered and the solvent was evaporated and dried on high vacuum to give a crude reddish solid. This solid was dissolved in EtOAc and hexane was added to precipitated the product. The resulting solid was filtered and the impure filter cake was combined with the filtrate and evaporated to dryness. This material was treated with EtOAc and EtOH. The resulting solid was filtered then suspended in EtOH, with stirring and heating at a low temperature. Then it was allowed to cool to room temperature. The suspension was filtered and washed with EtOH to give the titled product (280 mg, 19% yield).

EXAMPLES 77, 78 AND 79 IN TABLE 6 WERE PREPARED ACCORDING TO THE PROCEDURES DESCRIBED IN EXAMPLE 76

EXAMPLE 80

4-(1-(5-Benzyloxy-2-(bis-2,4-trifluoromethyl) benzyloxymethyl)indolinyl)methylbenzoic Acid Step 1: Methyl 1-(5-Benzyloxy-2-(hydroxymethyl) indolinyl)methylbenzoate 2-(5-Benzyloxy)indolinylmethanol (3.21 g, 12.6 mmol), prepared in DMF (20 mL), methyl 4-(bromomethyl) benzoate (2.88 g, 14.5 mmol) and potassium carbonate (1.77 g, heated to 125° C. before use) were mixed and stirred at room temperature for 2 h. The reaction was diluted with 100 mL of $H_2O$ and extracted three times with EtOAc. The combined EtOAc layers were evaporated to dryness to give the crude product (5.66 g). The crude material was purified on a silica gel column using hexane:ethyl acetate 3:1 to 2:1. The appropriate fractions were combined, evaporated to dryness and further dried on high vacuum to the product (3.00 g, 64%).

Step 2: Methyl 4-(1-(5-Benzyloxy-2-(bis-2,4-trifluoromethyl)benzyloxymethyl)indolinyl)methylbenzoate Ester (700 mg), prepared in step 1, and bis-(2,4-trifluoromethyl)benzyl bromide (0.35 mL) were dissolved in DMF (5 mL). The resulting clear yellow solution was cooled in an ice bath and then NaH (85 mg) was added in small portions over a period of 5 minutes. The suspension was stirred at 0° C. for 4 h. To complete the reaction, another 0.35 mL of 2,4-bis(trifluoromethyl)-benzyl bromide was added and the stirring was continued for another 3 h 40 min. The reaction was then diluted with $H_2O$ and extracted three times with EtOAc. The combined EtOAc layers were evaporated to give a crude product which was then purifed on a silica gel columnusing hexane:ethyl acetate 8:1. The appropriate fractions were combined and evaporated to dryness to give the product (0.417 g, 38.2% yield).
Step 3:
The titled compound was prepared according to the prodedure described in step 5 of Example 76.

EXAMPLES 81 AND 82 IN TABLE 6 WERE PREPARED ACCORDING TO THE PROCEDURES DESCRIBED IN EXAMPLE 80

EXAMPLE 83

5-(2-(1-(2,4-bis(Trifluoromethyl)benzyl)indolinyl) carboxamido-1,3-benzenedicarboxylic Acid Step 1: 2-(1-(2,4-bis(Trifluoromethyl)benzyl)indolinyl) carboxylic Acid 2-Indolinylcarboxylic acid (0.43 g, 2.6 mmol) was dissolved in DMF (5 mL), placed under $N_2$, and cooled to 0° C., the sodium hydride (0.26 g of a 60% dispersion, 6.5 mmol) was added and stirring was continued for 1 hour at this temperature. 2,4-Bis(trifluoromethyl)benzyl bromide (1.22 mL, 6.5 mmol) was next added and the reaction was warmed to room temperature overnight. The reaction was then diluted with 1/2 saturated ammonium chloride/ethyl acetate, the aqueous layer was extracted with ethyl acetate (3×), the organic layers were dried over magnesium sulfate and concentrated. The crude product was purified via chromatography (hexane:ethyl acetate 9:1) to yield 0.96 g of the ester. The resulting ester (0.87 g, 0.1.41 mmol) was dissolved in THF/methanol and then 1N sodium hydroxide (4.21 mL) was added and the resulting mixture was stirred 2 hours at RT, workup and purification via Chromatography (7:1 hexane:ethyl acetate with 1% acetic acid) yielded 0.58 g of the product.
Step 2:
The acid (0.25 g, 0.64 mmol), prepared in step 1, EDCI (0.16 g, 0.83 mmol), DMAP (7 mg, 0.06 mmol) and dimethyl 5-aminoisophthalate (0.16 g, 0.77 mmol) were dissolved in THF (2 mL) and refluxed 16 hours which yielded after aqueous workup 0.33 g of a crude product. The ester (0.29 g, 0.50 mmol) was dissolved in THF/methanol and then 1N sodium hydroxide (1.5 mL) was added and the resulting mixture was stirred 16 hours at RT, workup and purification via Chromatography (1:1 hexane:ethyl acetate with 1% acetic acid) yielded 0.22 g of the titled compound.

EXAMPLE 84

N-Methylsulfonyl-2-(1-(2,4-bis(trifluoromethyl) benzyl)indolinyl)carboxamide

The acid (0.13 g, 0.32 mmol), prepared in step 1 of Example 83, EDCI (0.07 g, 0.39 mmol), DMAP (4 mg, 0.03 mmol) and methylsulfonanilide (0.04 g, 0.39 mmol) were dissolved in THF (5 mL) and refluxed 16 hours which yielded after workup (0.16 g), purification via Chromatography (98:2 dichloromethane:methanol) yielded 0.04 g of the titled compound (29%).

EXAMPLE 85

N-Phenylsulfonyl-2-(1-(bis-2,4-trifluoromethyl) benzyl)indolinyl)carboxamide

The titled compound was prepared according to the prodedure described in Example 84, but using phenylsulfonylamide.

EXAMPLE 86

5-(2-(5-Methoxybenzyloxy-1-(2,4-bis (trifluoromethyl)benzyl)indolinyl) methylaminocarboxamido-1,3-benzenedicarboxylic Acid Step 1: 2-Trimethylsilylethyl 1-(5-Benzyloxy-2-hydroxymethyl)indolinylformate An oven-dried 1 L round bottom flask, equipped with a stir bar was charged with 2-(5-benzyloxy)indolinylmethanol (33.2 g, 130 mmol), prepared in step 1 of Example 17, 2-(trimethylsilyl)ethyl p-nitrophenyl carbonate 36.8 g, 130 mmol), $NEt_3$ (38 ml, 273 mmol), and 300 mL of anhydrous DMF. The reaction mixture was stirred at 6° C. for 28 hours and at room temperature overnight. The resulting solution was concentrated to dryness in vacuo, and 1 L of $CHCl_3$ and 200 mL of saturated $NaHCO_3$ solution were added. The layers were separated, and the organic phase was dried ($Na_2SO_4$), filtered, and concentrated. The crude material obtained (55.7 g) was purified by column chromatography on silica gel (eluant: 0–5% MeOH in dichloromethane) to afford product (33.5 g, 60% yield).
Step 2: 2-Trimethylsilylethyl 1-(5-Hydroxy-2-hydroxymethyl)indolinylformate An oven-dried 500 mL Parr pressure flask was charged with the alcohol (30 g, 75 mmol), prepared in step 1, Pd/C (10%, 2.2 g), 100 mL of MeOH, and 300 mL of EtOAc. After being shaken overnight in a Parr apparatus under $H_2$ atmosphere (50 psi), the reaction mixture was filtered through Florisil. The filtrate was concentrated to dryness on the rotary. The crude material obtained (24 g) was purified by column chromatography on silica gel (eluant: 0–3% MeOH in dichloromethane) to afford product (20.9 g, 90% yield).
Step 3: 2-Trimethylsilylethyl 1-(5-(4-Methoxy)benzyloxy-2-hydroxymethyl)indolinylformate An oven-dried 1 L round bottom flask, equipped with a stir bar was charged with the diol (27.1 g, 87.7 mmol), prepared in step 2, 4-methoxybenzyl chloride (Aldrich, 15 mL, 110 mmol), $K_2CO_3$ (200 mesh, 30.4 g, 220 mmol), KI (Aldrich, 18.3 g, 110 mmol), and 800 mL of anhydrous acetonitrile. The reaction mixture was heated at reflux for 4 h. The solution was allowed to cool to room temperature and water (800 mL) and $CHCl_3$ (1.5 L) were added. The layers were separated, and the aqueous phase was extracted with $CHCl_3$ (800 mL). The combined extracts were washed with water (200 mL), dried ($Na_2SO_4$), filtered, and concentrated. The crude material obtained (45 g) was purified by column chromatography on silica gel (eluant: 20–25% EtOAc in hexane), and recrystallization from EtOAc/Hexane to afford product (22.2 g, 59% yield).
Step 4: 2-Trimethylsilylethyl 1-(5-(4-Methoxy)benzyloxy-2-bromomethyl)indolinylformate To a solution of 3.0 g (6.4 mmol) of the alcohol, prepared in step 3, in 30 mL of dichloromethane was added 2.53 g (7.6 mmol) of carbon tetrabromide and 3.15 g (7.6 mmol) of 1,3-bis(diphenylphosphino)propane. The reaction was stirred at room temperature for 18 h. The reaction was quenched with saturated aqueous $NH_4Cl$, and the product was extracted with dichloromethane. The combined organic extracts were washed with brine and dried over $MgSO_4$. The crude product was purified by flash chromatography using hexane:ethyl acetate 3:2 to afford 1.51 g of the product.
Step 5: 2-Trimethylsilylethyl 1-(5-(4-Methoxy)benzyloxy-2-azidomethyl)indolinylformate To a solution of 1.4 g (2.6 mmol) of the bromide, prepared in step 4, in 15 mL of dimethylformamide was added 0.51 g (7.9 mmol) of sodium azide. The reaction was heated to 75° C., and was stirred for 18 h. The reaction was quenched with water, and the product was extracted with ethyl acetate. The combined organic layers were washed with water, brine and dried over MgSO$_4$. The crude product was purified by flash chromatography using hexane:ethyl acetate 4:1 to afford 1.08 g of the product.

Step 6: 2-Trimethylsilylethyl 1-(5-(4-Methoxy)benzyloxy-2-aminomethyl)indolinylformate To a solution of 0.88 g (1.9 mmol) of the azide, prepared in step 5, in 20 mL of ethanol was added 90 mg (10%/wt) of Pd/CaCO$_3$. The mixture was placed under atmospheric hydrogen, and was stirred for 18 h. The reaction was then filtered through a pad of celite and the organic phase was concentrated. The crude product was purified by flash chromatography using 10% MeOH/CH$_2$Cl$_2$ to afford 0.717 g of the product.

Step 7: Methyl 5-(2-(5-Methoxybenzyloxy-1-(2-trimethylsilyloxy)ethoxycarbony)indolinyl)methylaminocarboxamido-1,3-benzenedicarboxylate To a solution of 0.164 g (0.6 mmol) of triphosgene in 5 mL of dichloromethane was added a solution of 0.31 g (1.5 mmol) of dimethyl-5-aminoisophthalate and 0.39 g (3.0 mmol) of diisopropylethylamine in 20 mL of dichloromethane over a 30 minute period via a syringe pump. The reaction was stirred for 1 h at room temperature following the addition, and then a solution of 0.64 g (1.5 mmol) of the amino, prepared in step 6, in 5 mL of dichloromethane was added in one portion. The reaction was stirred for 2 h, and then quenched with water. The product was extracted with ethyl acetate, and the combined organic layers were washed with water, saturated aqueous NaHCO$_3$, brine and dried over MgSO$_4$. The crude product was purified by flash chromatography using 10% MeOH/CH$_2$CL$_2$ to afford 0.78 g of the product.

Step 8: Methyl 5-(2-(5-Methoxybenzyloxy)indolinyl)methylaminocarboxamido-1,3-benzenedicarboxylate To a solution of 0.485 g (0.7 mmol) of the ester, prepared in step 7, in 20 mL of acetonitrile was added 2.2 mL (2.2 mmol) of a 1.0 M tetrabutylammonium fluoride solution in THF. The reaction was stirred at room temperature for 18 h. The reaction was quenched with brine, and the product was extracted with ethyl acetate. The combined organic extracts were washed with saturated aqueous NH$_4$Cl, brine and dried over MgSO$_4$. The crude product was purified by flash chromatography using 5% MeOH/CH$_2$Cl$_2$ to afford 0.342 g of the product.

Step 9: Methyl 5-(2-(5-Methoxybenzyloxy-1-(bis-2,4-trifluoromethyl)benzyl)indolinyt)methylaminocarboxamido-1,3-benzenedicarboxylate To a solution of 0.15 g (0.3 mmol) of the indoline diester, prepared in step 8, in 5 mL of dimethylformamide was added 0.097 g (0.3 mmol) of 2,4-bis(trifluoromethyl)benzyl bromide and 0.12 g (0.9 mmol) of potassium carbonate. The reaction was stirred at room temperature for 18 h. The reaction was quenched with water, and the product was extracted with ethyl acetate. The combined organic extracts were washed with water, brine and dried over MgSO$_4$. The crude product was purified by flash chromatography using hexane:ethyl acetate 1:1 to afford 0.066 g of the product.

Step 10:

To a solution of 0.063 g (0.1 mmol) of the diester, prepared in step 9, in 5 mL of tetrahydrofuran was added 0.8 mL (0.8 mmol) of a 1.0 N NaOH solution and 0.5 mL of methanol. The reaction was stirred at room temperature for 18 h. The organic solvents were evaporated, and the resulting solid was suspended in water and acidified to pH 3 with 10% HCl. The product was extracted with ethyl acetate, and the combined organic extracts were washed with water, brine and dried over MgSO$_4$. The crude product was purified by flash chromatography using 5% MeOH/CH$_2$Cl$_2$ to afford 0.049 g of the titled compound.

EXAMPLE 87 WAS PREPARED ACCORDING TO THE PROCEDURE DESCRIBED IN EXAMPLE 86, BUT USING 4-(3,5-BIS (TRIFLUOROMETHYL)PHENOXYMETHYL) BENZYL BROMIDE

INTERMEDIATE 1

Methyl 4-Methoxy-3-thioacetamidobenzoate

Step 1: bis(Methyl 4-Methoxy-3-dithioacetamidobenzoate)

A 2-L oven-dried round bottom flask fitted with a magnetic stirring bar was charged with Dithioacetic acid (10.2–15.5 g, 56–85 mmol) and anhydrous CH$_2$Cl$_2$ (50 mL). Oxalyl chloride (2.1 mol equiv.) was added dropwise over 10 min. The reaction mixture was stirred at room temperature for 4–5 h. Methyl 4-methoxy-3-amidobenzoate (2.1 mol equiv.) in anhydrous CH$_2$Cl$_2$ (300–500 mL) and DMAP (0.1 mol equiv.) were added at room temperature. NEt$_3$ (4.2 mol equiv.) was added dropwise over 30 min. After stirring overnight at room temperature the reaction mixture was washed with 1 N HCl solution (2×300 mL), dried over Na$_2$SO$_4$ and filtered. The solvent was removed in vacuo. Purification of the residue by column chromatography on silica gel using hexane:ethyl acetate=5:1 afford desired product in 56% yield.

Step 2:

A 1-L round bottom flask fitted with a magnetic stirring bar was charged with disulfide, prepared in step 1, (15.7–26.3 g, 36.6–57.5 mmol) and PPh$_3$ (1.1 mol equiv.). The reactants were suspended in dioxane/H$_2$O (4/1, 375–500 mL) and concentrated HCl solution (5 drops) was added. The reaction mixture was heated at 40° C. until all disulfide was consumed. Solvents were removed in vacuo. The residue was purified immediately by column chromatography on silica gel using hexane:ethyl acetate 2:1 to afford the titled product in 89% yield.

INTERMEDIATE 2

Methyl 5-Thioacetamido-1,3-benzenedicarboxylate

The titled compound was synthesized according to the procedures described in Intermediate 1 using 5-amino-1,3-benzenedicarboxylate.

UNINTERMEDIATE 3

Methyl 2-(3-Amino4-methoxyphenyl)-2-methoxyacetate

Step 1: Methyl 2-(3-Nitro4-methoxyphenyl)acetate

An oven-dried 2-L, 3-neck round bottom flask, equipped with a mechanical stir motor, a low-temperature thermometer and an equalizing dropping funnel, was charged with acetic anhydride (631 mL) and subsequently cooled to −78° C. Fuming nitric acid (Baker, 90%, 27 mL) was added dropwise via the dropping funnel protected with a drying tube filled with CaCl$_2$. After addition was completed, the reaction temperature was allowed to warm to 20° C. over 1 h. The reaction mixture was cooled to −78° C. again and added 4-methoxyphenylacetic acid (50 g, 0.28 mol) dropwise via the dropping funnel. After stirring at −50° C. for 1 h., the reaction mixture was allowed to warm to −30° C. over 20 min. and then cooled to −50° C. again. The reaction mixture was quenched with H$_2$O (500 mL) at −50° C. and warmed up to room temperature and stirred for 0.5 h. The reaction mixture was partitioned between $CH_2Cl_2$ (500 mL) and $H_2O$. The aqueous layer was extracted with $CH_2Cl_2$ (3×500 mL). The combined $CH_2Cl_2$ extracts were concentrated in vacuo to give a yellow oil. This was added slowly to a 2 M solution of NaOH (2 L) cooled at 0° C. and stirred at room temperature overnight. The reaction mixture was partitioned between $CH_2Cl_2$ (500 mL) and $H_2O$. The aqueous layer was extracted with $CH_2Cl_2$ (3×500 mL). The combined $CH_2Cl_2$ extracts were stirred with 2 M NaOH solution (1 L) for 1 h. The layers were separated and the organic layer was washed with $H_2O$ (500 mL), brine (500 mL), dried over $Na_2SO_4$ and filtered. The solvents were removed in vacuo to afford crude product as a light yellow solid (56 g). Purification by recrystallization from MeOH (600 mL) gave product. Yield 48 g (77%).

Step 2: Methyl 2-(3-Nitro-4-methoxyphenyl)-2-hydroxyacetate

A 25-mL oven-dried round bottom flask fitted with a magnetic stirring bar was charged with ester (2.3 g, 10 mmol), prepared in step 1, and anhydrous THF (100 mL). The reaction mixture was cooled to −78° C. and a solution of $NaN(SiMe_3)_2$ (1.0 M in THF, 12 mL, 12 mmol) was added dropwise over 10 min. After stirring at −78° C. for 30 min., the deep purple solution was added dropwise a solution of racemic camphor sulfonyloxaziridine (3.4 g, 15 mmol), prepared by mixing the commercially available (IS)-(+)-(10-camphorsulfonyl)oxaziridine (1.7 g) and (IR)-(−)-(10-camphorsulfonyl)oxaziridine (1.7 g) in 50 mL THF. After stirring at −78° C. for 30 min., the reaction mixture was quenched with sat. $NH_4Cl$ solution (45 mL) at −78° C. and then allowed to warm to room temperature. The reaction mixture was partitioned between ether (250 mL) and $H_2O$ (50 mL). The aqueous laver was extracted with ether(3×250 mL). The combined ether extracts were washed with brine (250 mL), dried over $Na_2SO_4$ and filtered. The solvents were removed in vacuo. Purification by column chromatography on silica gel (eluant: 50% AcOEt in hexane) afforded desired product. Yield 2.2 g (88%).

Step2 3: Methyl 2-(3-Nitro-4-methoxyphenyl)-2-methoxyacetate

A 10-mL oven-dried round bottom flask fitted with a magnetic stirring bar was charged with alcohol (0.30 g, 1.24 mmol), prepared in step 2, AgO (0.68 g, 3.0 mmol) and toluene (3 mL). To this was added $CH_3I$ (0.36 g, 5.75 mmol) dropwise. The reaction flask was capped tightly and placed into a sonication chamber. The reaction mixture was sonicated for 18 h while stirring at room temperature. The reaction mixture was filtered through Celite and concentrated in vacuo to dryness. The residue was purified by column chromatography on silica gel (eluant: 30% AcOEt in hexane) to afford desired product. Yield 0.26 g (82%).

Step 4:

A 100-mL oven-dried round bottom flask fitted with a magnetic stirring bar and a three way adapter, connecting to a hydrogen balloon and a water aspirator was charged with nitro compound (0.7 g, 2.6 mmol), 5% Pd on Carbon (10% by weight) and MeOH (20 mL). The reaction flask was placed under vacuum via the water aspirator and subsequently filled with $H_2$. This was repeated three times. The reaction mixture was stirred for 18 hours under positive $H_2$ pressure until all starting material was reacted. The reaction mixture was filtered through Celite and concentrated in vacuo to dryness. The residue was purified by column chromatography on silica gel using 10% ethyl acetate in dichloromethane to afford the titled compound (0.57 g, 97%)

INTERMEDIATE 4

Methyl 2-(3-Amino-4-Methoxylphenyl)-2-tert-bultydimethylsilyloxyacetate

A 25-mL oven-dried round bottom flask fitted with a magnetic stirring bar was charged with alcohol (0.30 g, 1.24 mmol), prepared in step 2 of Intermediate 3 and anhydrous $CH_2Cl_2$ (10 mL). The reaction mixture was cooled to 0° C. and added 2,6-lutidine (dried over NaOH pellet, 0.36 mL, 3.11 mmol) followed by addition of $BuMe_2SiOTf$ (0.43 mL, 1.87 mmol) dropwise. After stirring at 0° C. for 30 min., the reaction mixture was partitioned between $CH_2Cl_2$ (20 mL) and $H_2O$ (15 mL). The aqueous layer was extracted with $CH_2Cl_2$ (3×20 mL). The combined $CH_2Cl_2$ extracts were washed with brine (20 mL), dried over $Na_2SO_4$ and filtered. The solvents were removed in vacuo. Purification by column chromatography on silica gel (eluant: 30% AcOEt in hexane) afforded desired product. Yield 0.42 g(95%).

Step 2:

The titled compound was prepared from nitro compound of step 1 according to the procedure described in step 4 of Intermediate 3.

INTERMEDIATE 5

Methyl 2-(3-Amino4-methoxyphenyl)acetate

The titled compound was prepared from nitro compound, prepared in step 1 of Intermediate 3, according to the procedure described in step 4 of Intermediate 3.

INTERMEDIATE 6

Methyl 2-(3-Amino-4-methoxyphenyl)-2-methylacetate

Step 1 Methyl 2-(3-Nitro4-methoxyphenyl)-2-methylacetate

A 25-mL oven-dried round bottom flask fitted with a magnetic stirring bar was charged with redistilled diisopropylamine (0.84 mL, 6.0 mmol) and anhydrous THF (10 mL) and cooled to 0° C. A solution of n-BuLi (2.5 M in hexane, 2.4 mL, 6.0 mmol) was added dropwise over 5 min. After stirring at 0° C. for 15 min., the reaction temperature was allowed to cool to −78° C. and added a solution of easter (1.13 g, 5.0 mmol), prepared in step 1 of Intermediate 3, in 10 mL THF dropwise. After stirring at −78° C. for 45 min., dimethylsulfate (1.60 g, 12.5 mmol) was added dropwise and the reaction mixture was allowed to warm to room temperature and stirred overnight. The reaction mixture was partitioned between $CH_2Cl_2$ (50 mL) and $H_2O$ (50 mL). The aqueous layer was extracted with $CH_2Cl_2$ (3×50 mL). The combined $CH_2Cl_2$ extracts were washed with brine (50 mL), dried over $Na_aSO_4$ and filtered. The solvents were removed in vacuo. Purification by column chromatography on silica gel (eluant: 30% AcOEt in hexane) afforded 0.7 g of product (58%).

Step 2:

The titled compound was prepared from nitro compound, prepared in step 1, according to the procedure described in step 4 of Intermediate 3.

INTERMEDIATE 7

Methyl 2-(3-Amino4-methoxyphenyl)-2-allylacetate

Step 1: Methyl 2-(3-Nitro-4-methoxyphenyl)-2-allylacetate

This compound was synthesized form ester, prepared in step 1 of Intermediate 3, according to the procedure described in step 1 of Intermediate 6, but using allyl bromide.

Step 2:

A 25-mL oven-dried round bottom flask fitted with a magnetic stirring bar was charged with ester (0.30 g, 1.13 mmol), prepared in step 1, $SnCl_2$ $2H_2O$ (1.28 g, 5.66 mmol) and EtOH (5 mL). The reaction mixture was heated at 70°

C. for 30 min. The reaction mixture was cooled to room temperature and poured onto ice/water (20 mL) and basified with saturated $Na_2CO_3$ solution to pH=8. AcOEt (50 mL) was added. The resulting emulsion was filtered through Celite. The filtrate was partitioned between AcOEt (20 mL) and $H_2O$ (15 mL). The aqueous layer was extracted with AcOEt(3×50 mL). The combined AcOEt extracts were washed with brine (50 mL), dried over $Na_2SO_4$ and filtered. The solvents were removed in vacuo. Purification of the residue by column chromatography on silica gel (eluant: 10% AcOEt in $CH_2Cl_2$) afforded the titled compound. Yield 0.16 g (60%).

INTERMEDIATE 8

2,4-bis(1,1-Dimethypropyl)phenoxyacetic Acid

The 2,4-bis(1,1-dimethy)propylphenol (12 g, 51.2 mmol) in dimethylformamide (100 mL) was cooled to −30° C., treated with solid potassium bis(trimethylsilyl)amide (12.3 g, 61.5 mmol), stirred for 30 minutes and then methyl bromoacetate (5.7 mL, 61.5 mmol) was added, the reaction was stirred 1 hour at this temperature and five hours after removal of the cooling bath, workup yielded (16.6 g, ≈100%) a yellow oil. The oil was dissolved in THF/methanol and treated with 1N sodium hydroxide (155 mL) and stirred for 48 hours. The reaction was concentrated, diluted with water, acidified to pH 4 with concentrated HCl, extracted with ethyl acetate (4×), dried over magnesium sulfate and concentrated. Crystallization from ethyl acetate and hexane yielded 12.85 g of the titled compound. (86%).

INTERMEDIATE 9

4-Benzylphenoxyacetic Acid

The titled compound was prepared from 4-benzylphenol according to the procedure described in of Intermediate 8.

INTERMEDIATE 10

2-Naphthoxyacetic Acid

The titled compound was prepared from 2-naphthol according to the procedure described in of Intermediate 8.

INTERMEDIATE 11

3,5-bis(Trifluoromethyl)phenoxyacetic Acid

The titled compound was prepared from 3,5-bis(trifluoromethyl)phenol according to the procedure described in of Intermediate 8.

INTERMEDIATE 12

Methyl 5-Amino-3-(N,N-dimethyl)carbamoylbenzoate

Step 1: Methyl 5-Nitro-3-(N,N-dimethyl)carbamoylbenzoate

A 100-mL oven-dried round bottom flask fitted with a magnetic stirring bar was charged with 5-nitro-3-methoxycarbonylbenzoic acid (3.15 g, 10 mmol), DMF (1 drop), anhydrous $CH_2Cl_2$ (70 mL), and oxalyl chloride (3.7 mL, 42.3 mmol). The reaction mixture was stirred at room temperature for 2 h. The solvent was removed in vacuo to afford acid chloride as a white solid. This was used immediately in the next step without further purification.

An oven-dried round bottom flask fitted with a magnetic stirring bar was charged with above prepared acid chloride (14 mmol), anhydrous $CH_2Cl_2$ (50 mL), and dimethylamine hydrochloride (70 mmol). $NEt_3$ (2 mL, 144 mmol) was added dropwise. After stirring at room temperature for 30–60 min excess $NEt_3$ (1 mL, 72 mmol) was added and stirring was continued. After 30–60 min the solution was washed with saturated $Na_2CO_3$ solution (2×20 mL), dried over $Na_2SO_4$ and filtered. The solvent was removed in vacuo to afford 3.3 g of product. This was used in the next step without further purification.

Step 2:

The titled compound was prepared from nitro compound, prepared in step 1, according to the procedure described in step 4 of Intermediate 3.

INTERMEDIATE 13

Methyl 5-Amino-3-acetylbenzoate

Step 1: Methyl 5-Nitro-3-acetlylbenzoate

A 250-mL oven-dried round bottom flask fitted with a magnetic stirring bar was charged with di-tert-butyl malonate (2.16 g, 10 mmol), anhydrous toluene (50 mL), and NaH (60% suspension in mineral oil, 0.88 g, 22 mmol). The reaction mixture was heated at 8° C. for 1 h. A solution of methyl 5-nitro-3-chloroformylbenzoate (10 mmol), prepared in step 1 of Intermediate 12, in anhydrous toluene (20 mL) was added and heating was continued for 2 h. The reaction mixture was cooled to room temperature and p-toluenesulfonic acid (0.21 g, 1.2 mmol) was added. The resulting mixture was filtered and the oily residue was washed with toluene until a white solid was left. The filtrates were combined and the solvent was removed in vacuo. The resulting oil was dissolved in anhydrous toluene (50 mL) and p-toluenesulfonic acid (0.3 g, 1.74 mmol) was added. After heating to reflux for 18 h the reaction mixture was allowed to cool to room temperature, washed with saturated $Na_2CO_3$ solution (2×25 mL), dried over $Na_2SO_4$ and filtered. The solvent was removed in vacuo. The crude material was purified by column chromatography on silica gel (eluant: $CH_2Cl_2$) to afford product. Yield 1.06 g (50%).

Step 2:

The titled compound was prepared from nitro compound, prepared in step 1, according to the procedure described in step 4 of Intermediate 3.

INTERMEDIATE 14

Methyl 5-Amino-3-(1-tert-butyldimethylsilyloxy)ethylbenzoate

Step 1: Methyl 5-Nitro-3-(1-hydroxy)ethylbenzoate

An oven-dried round bottom flask fitted with a magnetic stirring bar was charged with compound methyl 5-nitro-3-acetylbenzoate (0,5 g), prepared in step 1 of Intermediate 13, $BH_3THF$ (1 M solution in THF, 5 mol equiv.), and anhydrous THF. After stirring at room temperature for 24 h, $H_2O$ (20 mL) was added and the solution was concentrated in vacuo. The residue was taken in $H_2O$ (20 mL) and extracted with $CHCl_3$ (3×100 mL). The combined $CH_2Cl_2$ extracts were washed with saturated $Na_2CO_3$ solution (20 mL), dried over $Na_2SO_4$ and filtered. The solvent was removed in vacuo to afford product. This was used in the next step without further purification.

Step 2: Methyl 5Nitro-3-(1-tert-butyldimethylsilyloxy)ethylbenzoate

An oven-dried round bottom flask fitted with a magnetic stirring bar was charged with alcohol (0.5 g, 5 mmol), prepared in step 1, tert-$BuMe_2SiCl$ (1.3 mol equiv.), imidazole (2.15 mol equiv.), and anhydrous THF. After stirring at room temperature for 28 hours the solvent was removed in vacuo. The residue was taken in H₂O (50 mL) and extracted with CH₂Cl₃ (2×100 mL). The combined CHCl₃ extracts were washed with H₂O (50 mL), dried over Na₂SO₄ and filtered. The solvent was removed in vacuo. The crude material was purified on silica gel using 25%–50% diclo-romethane in hexane to afford the product (0.69 g, 91%).
Step 3:
The titled compound was prepared from nitro compound, prepared in step 2, according to the procedure described in step 4 of Intermediate 3.

INTERMEDIATE 15

Methyl 4-Methoxy-3-(2-thioethyl)aminobenzoate
Step 1: bis(2-Bromoethyl)disulfide
The dithioethanol (0.79 mL, 6.48 mmol), carbon tetra-bromide (4.3 g, 13.0 mmol) and 1,3 bis(diphenylphosphino)propane (5.34 g, 13.0 mmol) were weighed into a flask and flushed with nitrogen and then taken up in CH₂Cl₂ (15 mL) and stirred for 16 hours, workup consisted of pouring into 1/2 saturated ammonium chloride and extracted with CH₂Cl₂ (3×) dry magnesium sulfate and concentrated to yield (9.0 g) of a crude product that was chromatographed (Hexane:Ethyl acetate9:1) to yield 1.49 g of product.
Step 2: bis-(Methyl 4-methoxy-3-(2-dithioethyl) aminobenzoate
Bromide (0.39 mg, 1.387 mmol), prepared in step 1, and methyl 3-amino4-methoxy benzoate (1.00 g, 5.51 mmol) were added into a flask, flush with nitrogen and take up in DMF (5 mL) and then heat to 60° C. for 24 hours at which time the reaction was diluted with ethyl acetate and quenched into water, extracted with ethyl acetate (3×), the combined organic layers were washed with water (3×), dried and concentrated to yield 1.27 g of a product that was purified by chromatography (hexane:ethyl acetate 5:1 to 3:1) to yield 0.15 g of the desired product.
Step 3:
The disulfide (0.15 g, 0.24 mmol), prepared in step 2, and the triphenylphoshpine (0.14 g, 0.53 mmol) were taken up in THF (3 mL). H₂O (0.3 mL) and two drops of conc. HCl were added and the resulting mixture was stirred at 400° C. for 2 hours, the reaction was diluted with water and ethyl acetate, extracted with ethyl acetate (3×) and dried over magnesium sulfate to yield 0.27 g of a crude product that was purified by chromatography (hexane:ethyl acetate 9:1 to 6:1) to yield 0.11 g of the titled compound.

Methods of Synthesis for Examples 88–135

Additional compounds of the invention can be made according to the following methods. Specific examples of synthesis of compounds pursuant to these methods are also disclosed below.
Method A
The aldehyde is reacted with the alpha-carbon of a heterocycle such at 2,4-thiazolidinedione or rhodanine or 2-thiohydantoin in the presence of a base such a potassium carbonate or potassium hydroxide in a solvent system such a water:ethanol or ethanol. The resulting product may then be N-alkylated with a base such a sodium hydride in a solvent such a DMF or DMSO. The final acid may then be realized by cleavage of the ester with hydrogen fluoride in a solvent such as acetonitrile.
Method B
Indole-2-carboxylic acid was alkylated with an appropriate alkyl bromide which was then subjected to Suzuki coupling conditions using Pd(PPh₃)₄ as a catalyst in a mixed solvent (ethanol-benzene-water) at elevated temperature to give the 1-alkyl-5-substituted indole.

Method C
The starting material for the inhibitors in this class, 2-Ethoxycarbonyl-5-benzyloxyindole I, was deprotonated with a suitable base such as sodium hydride and alkylated on the nitrogen atom with selected electrophiles such as alkyl or benzyl halides to provide compounds II. Saponification of the ester functionality with a base such as aqueous sodium hydroxide in miscible solvents such as tetrahydrofuran and methanol gave inhibitors III. Further extensions at the 2-position were carried out through amide formation of the acid functionality via acid chloride formation with a suitable reagent such as oxalyl chloride and reaction with an amino-ester in the presence of a base such as pyridine in a suitable solvent such as methylene chloride. Saponification provided the chain extended acid moiety V.
Method D
Acid isosteres such as tetrazole were prepared from the carboxylic acids I via the nitrites III. Conversion to the nitrites was accomplished through primary amide formation of the acid functionality via the acid chloride with a suitable reagent such as oxalyl chloride and reaction with ammonia followed by a dehydration sequence using a suitable reagent such as oxalyl chloride and a base such as pyridine. The nitrites such as III could be converted to the tetrazoles by reaction with an azide source such as sodium azide in an appropriate high boiling point solvent such as N-methyl pyrrolidinone to give compounds such as IV.
Method E
Other acid isosteres such as the thiazolidinedione group with longer carbon atom bridges were prepared through a sequence involving the unsaturated aldehyde moiety at the 2-position such as compound IV. Partial reduction of the ester group in I with a suitable reagent such as diisobutyl aluminum hydride or reduction to a hydroxy group with a suitable reagent such as lithium aluminum hydride followed by oxidation to the aldehyde with a suitable oxidizing agent gave the aldehyde II. A Horner-Wittig reaction with tri-methoxyphosphonoacetate in a suitable solvent such as tetrahydrofuran gave the unsaturated ester III, which was converted to the aldehyde IV under the conditions described for II. The aldehyde could then be transformed to the thiazolidinedione V using a base such as piperdine and isolated with an acid such as acetic acid.
Method F
2-Indolyl carboxylic acid ethyl ester I is deprotonated with a strong base such as sodium hydride (NaH) in THF, and then reacted with a suitable alkyl bromide to give. VI. Hydrolysis of VI with a aqueous base such as sodium hydroxide and reaction with aniline or a substituted aniline in the presence of a carbodjimide such as dimethylamino-propylethyl carbodimide hydrochloride (EDCI) in a suitable solvent such as dichioromethane affords amide VII. Amide VII is hydrolyzed to corresponding acid VIII in a aqueous base such as sodium hydroxide.
Method G
Aldehyde IX is prepared from Indol-2-carboxylic acid ethyl ester I in two steps: (1) Reduction with lithium aluminium hydride or other hydride in a suitable solvent such as THF at 0° C. and (2) oxidation with an oxidizing reagent such as manganese dioxide in a solvent such as THF. Aldehyde IX can be alkylated by a suitable alkyl bromide (or iodide), such as benzyl bromide or ethyl iodide in the presence of a strong base such as sodium hydride or KHMDS in a solvent such as DMF to yield indole X. Indole X can be converted to an unsaturated acid XI in two steps: (1) Wittig reaction with a suitable reagent such as trimethyl phosphonoacetate in the presence of a base such as sodium hydride in a solvent such as THF and (2) Hydrolysis by aqueous sodium hydroxide.

Method H

Indole I can be converted to II in two steps: (1) reduction with LAH in a solvent such as THF and (2) silylation with t-butyldimethylsilyl chloride (TBDMSCl) in a solvent such as dichloromethane or DMF in the presence of a base such as imidazole. Treatment of II with Grignard reagent such as ethyl magnesium bromide in a solvent such as THF at −60° C., acylation of the resulting magnesium salt with a suitable acyl chloride such as acetyl chloride in ether and finally, alkylation on the nitrogen with an alkyl halide such as ethyl bromide in the presence of a strong base such as NaH in DMF affords ketone III. The silyl group on mi is removed using tetrabutylammonium fluoride in a solvent such as THF, the resulting alcohol is then converted to bromide using carbon tetrabromide and bis(diphenylphosphino) ethane in a solvent such as dichloromethane to yield bromide IV. Displacement of the bromine of IV with a thiol compound in the presence of a base such as cesium carbonate, or with an alcohol in the presence of a strong base such as NaH in DMF affords V (sulfide or ether respectively).

Method A

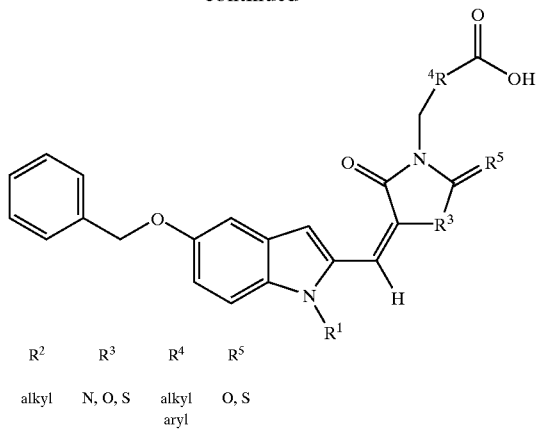

| $R^1$ | $R^2$ | $R^3$ | $R^4$ | $R^5$ |
|---|---|---|---|---|
| alkyl aryl | alkyl | N, O, S | alkyl aryl | O, S |

Method B

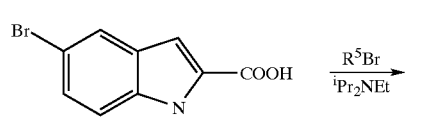

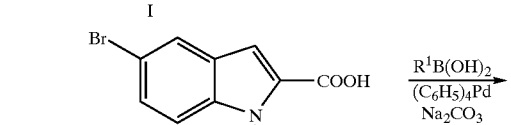

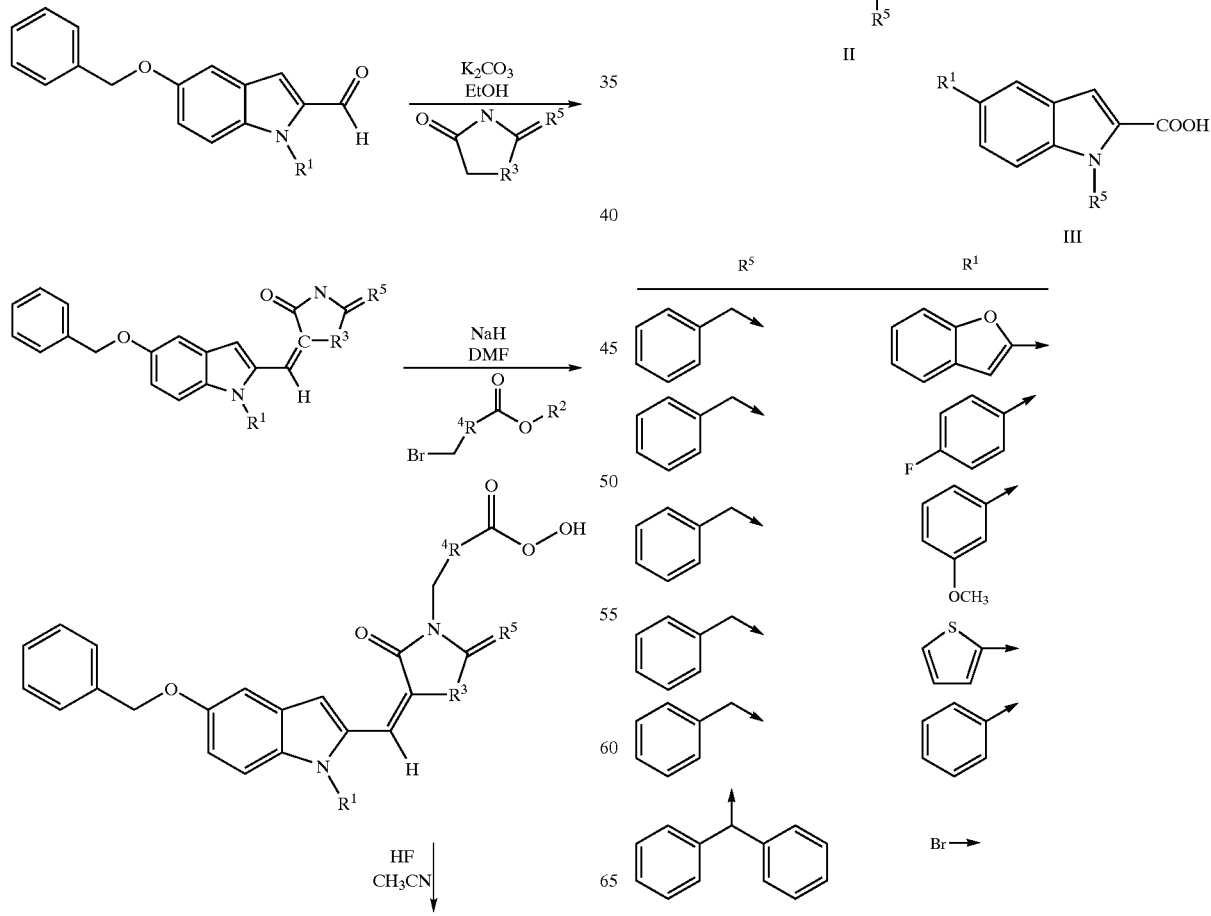

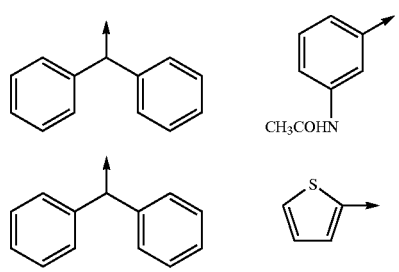
5
10
Method C
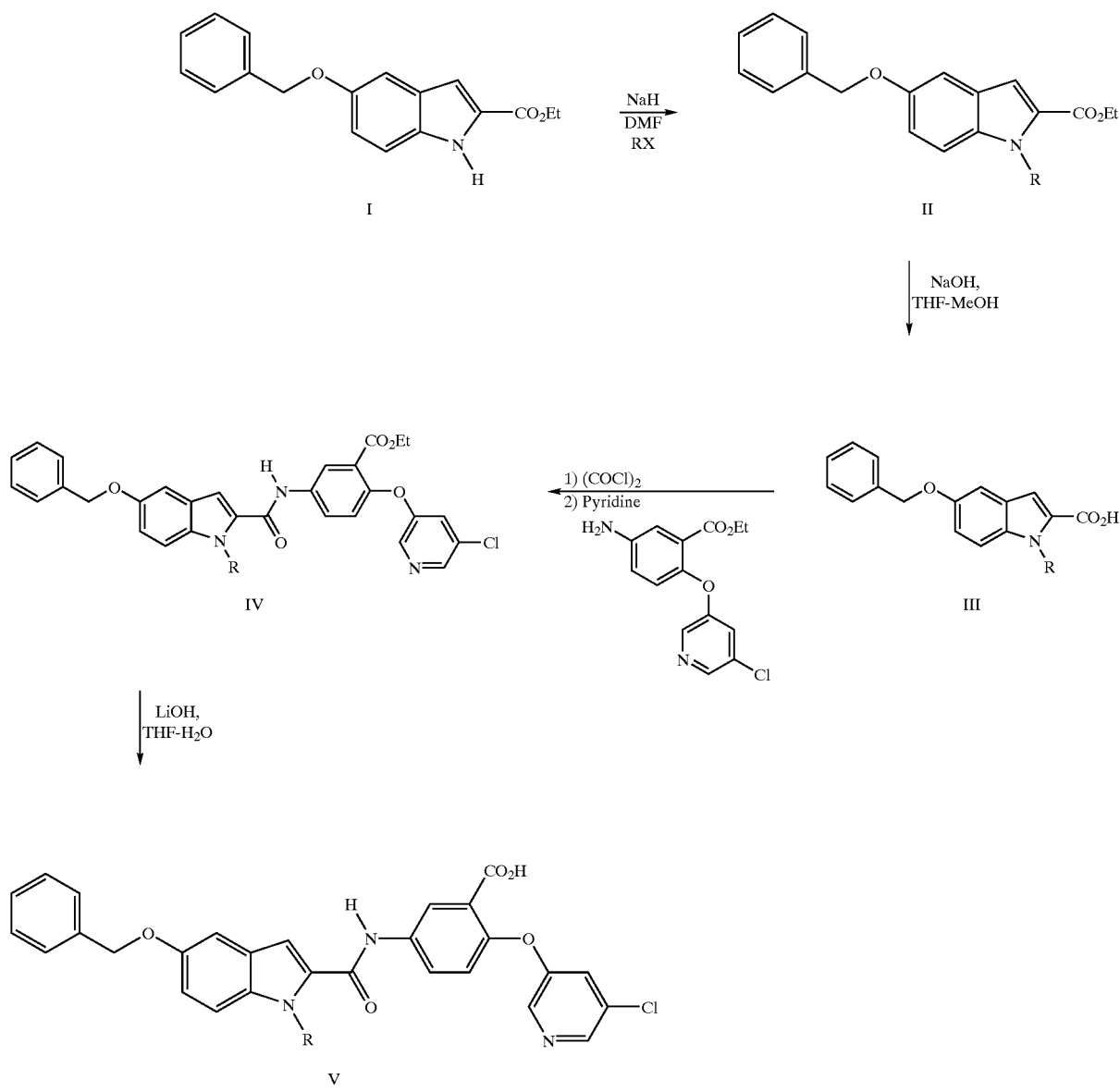

R = 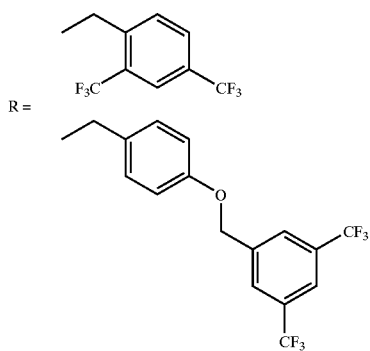
Method D
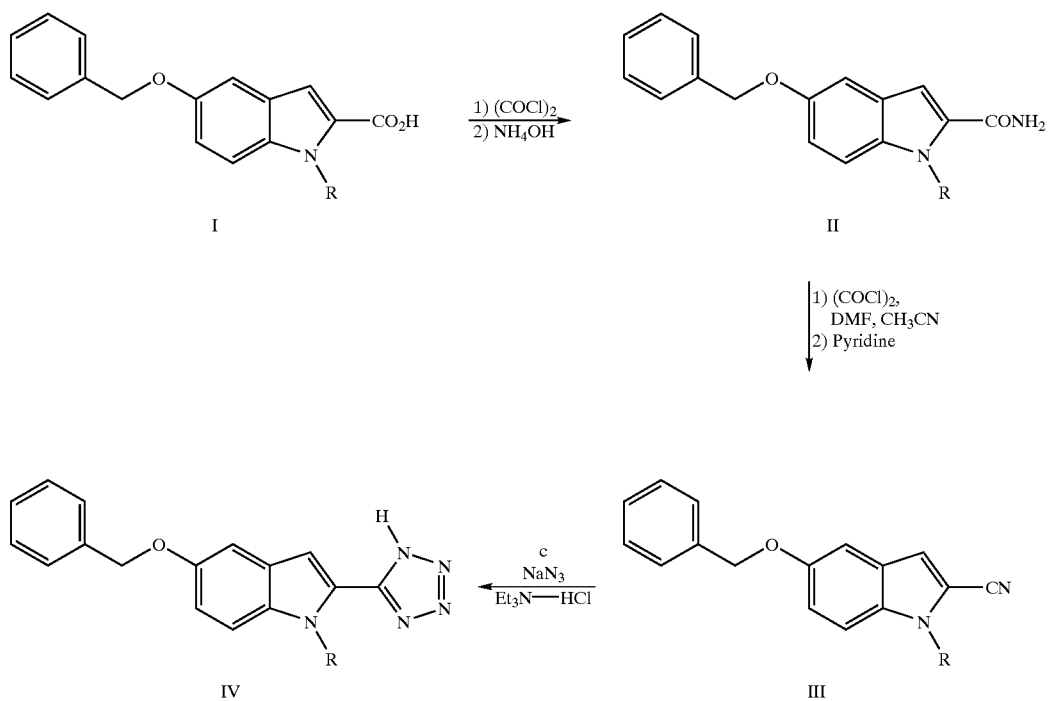
R = 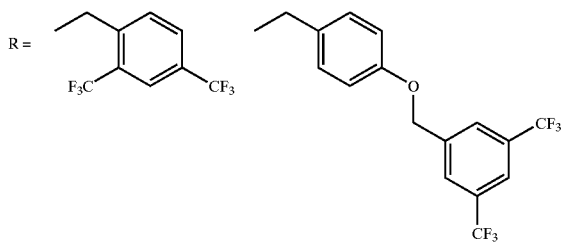

Method E
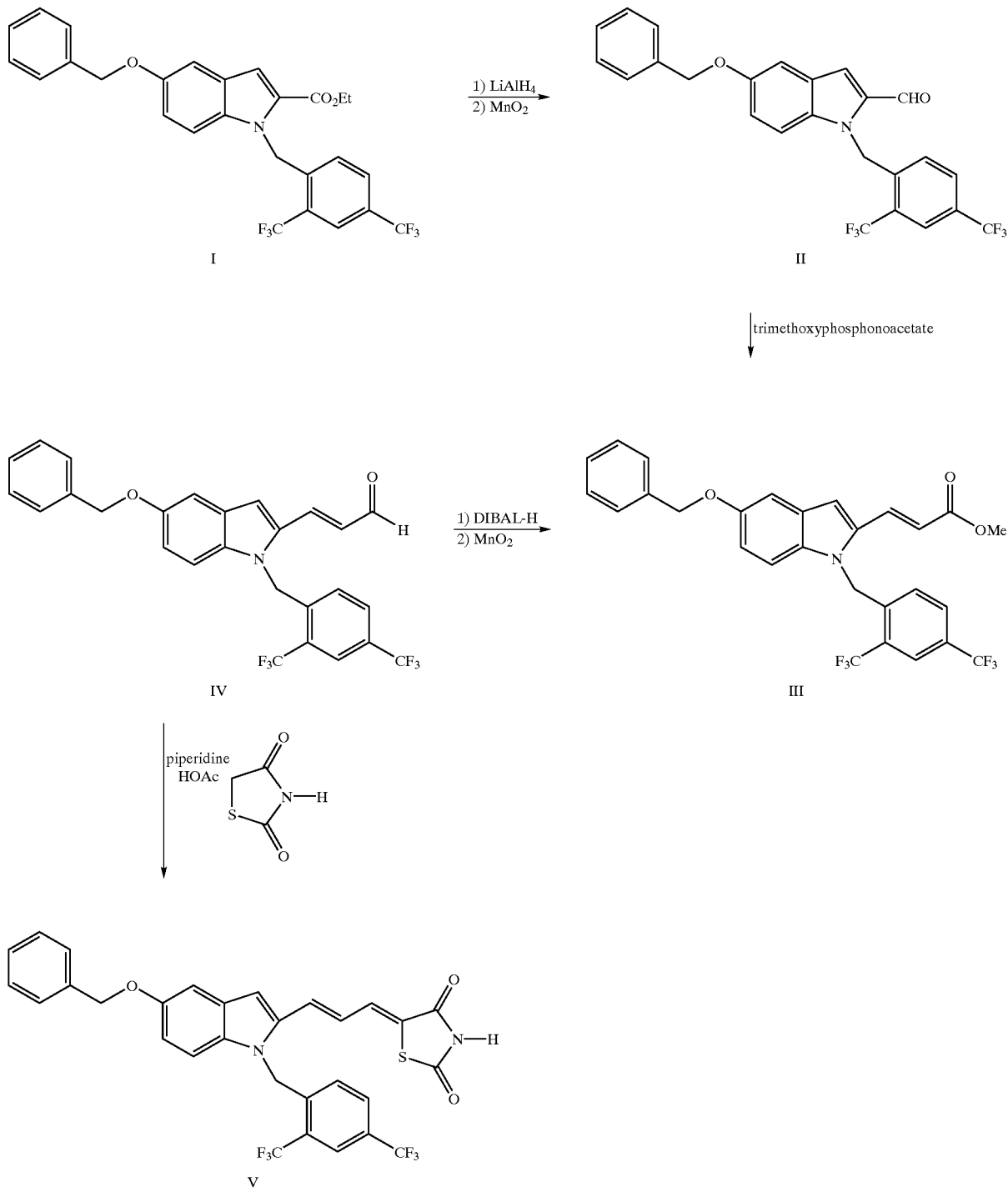
METHOD F
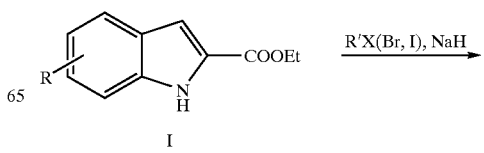

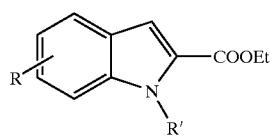
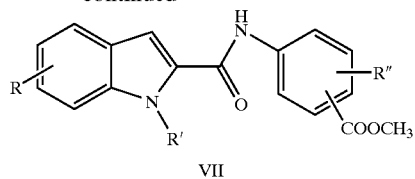
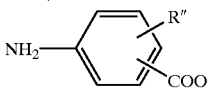
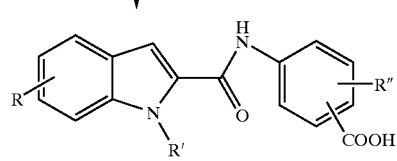
R = alkoxy, benzyloxy, phenoxy, halogen, CN, NO$_2$, alkyl or aryl
R' = alkyl, benzyl, alkenyl, alkynyl
R'' = halogen, CN, alkyl, alkoxy, alkoxycarbonyl, amido, acyl, H, OH
Method G
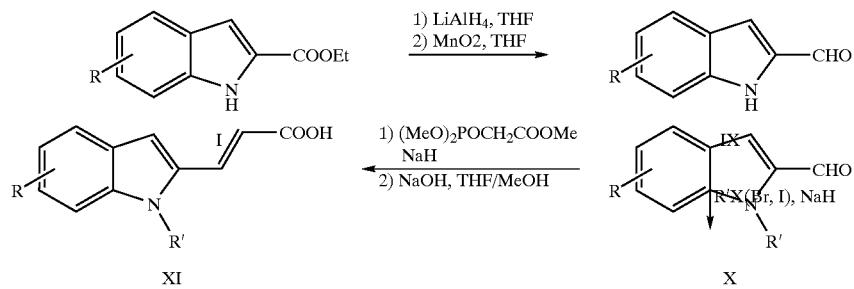
R = alkoxy, benzyloxy, phenoxy, halogen, CN, NO$_2$, alkyl or aryl
R' = alkyll, aryl
Method H
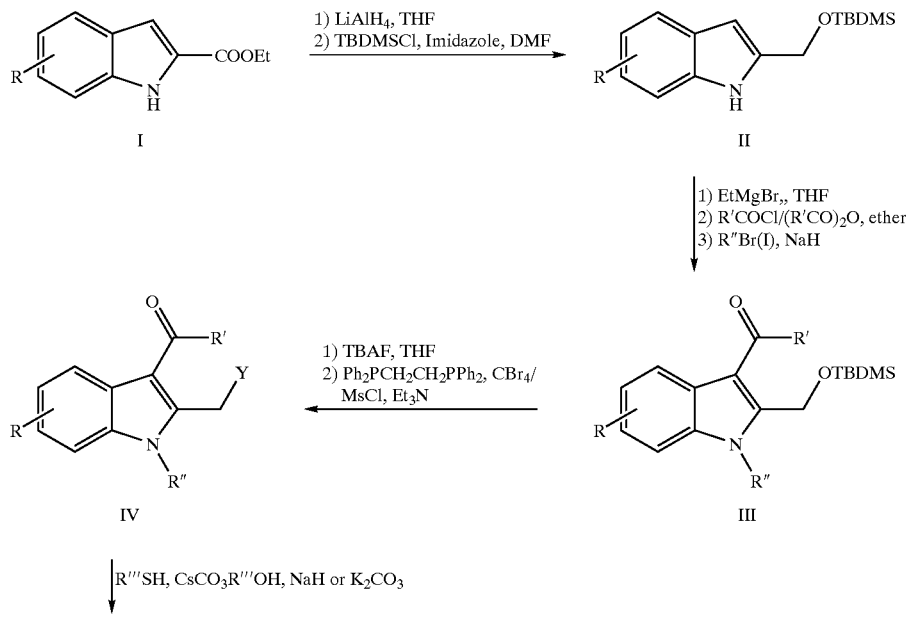

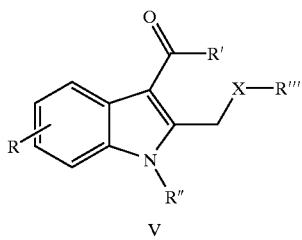

V

R = alkoxy, benzyloxy, phenoxy, halogen, CN, NO₂, alkyl or aryl
R' = alkyl, aryl
R" = alkyl, benzyl, alkenyl, alkynyl
R''' = alkyl, aryl
X = O, S
Y = halogen, mesylate

EXAMPLE 88

4-[(5-{(E)[5-(Benzyloxy)-1-(4-{[3,5-bis(trifluoromethyl)phenoxyl]methyl}benzyl)-1H-indol-2-yl]methylidene}-2,4-dioxo-1,3-thiazolan-3-yl)methyl]benzoic Acid Step 1—The aldehyde from Example 124, (5.2 g) was suspended in ethanol (150 mL). To the thick slurry was added 2,4-thiazolidinedione (1.28 g) and potassium carbonate (6.1 g). The mixture was heated in a bath at 60° C. (later dropped to 45° C.). After 1 h TLC showed no reaction. Sodium hydroxide (2.1 g) was added and the mixture was heated at 58° C. After 45 minutes the TLC showed reaction progress. Additional 2,4-thiazolidinedione (0.1 g) was added. The mixture was stirred overnight at room temperature. The mixture was poured into water (500 mL) and acidified to pH 2 with 6 N HCl, extracted with ethyl acetate, dried (MgSO4) and filtered. Trituration from ethanol afforded an orange solid which was filtered and washed with ethanol to give the desired product (5.74 g, 94%) as an orange solid.

Step 2—To the material prepared in step 1 (1.1 g) in DMF (15 mL) at 0° C. was added sodium hydride (0.08 g. 60% dispersion in mineral oil). The suspension was stirred for 30 minutes. To the reaction mixture was added the benzyl bromide (0.54 g) and the reaction was stirred overnight. Water was added and the mixture was extracted with ethyl acetate. The combined organic layers were concentrated. Column chromatography (1:6 ethyl acetate:hexane to 1:4 ethyl acetate:hexane) afforded the desired product (1.18 g, 75%) as a yellow solid.

Step 3—To the material prepared in step 2 (0.34 g) in acetonitrile (15 mL) was added HF (48% aqueous, 3.7 mL) via syringe. The reaction was stirred overnight. The reaction was not complete by TLC therefore THF was added to dissolve the starting material and additional HF (0.6 mL) was added. The reaction was stirred for 2 h after which the TLC showed reaction completion. Water was added which resulted in the formation of a yellow solid. The yellow solid was dissolved in ethyl acetate, washed with brine, dried over MgSO₄ and concentrated. The resulting crude solid was suspended in ethanol and stirred for 30 min, filtered and dried to afford the title compound (140 mg, 48%) as a yellow solid.

EXAMPLE 89

5-[(E)-(5-(Benzyloxy)-{3-[3,5-bis(trifluoromethyl]phenoxylpropyl}-1H-indol-2-yl)methylidene]-1,3-thiazolane-2,4-dione The title compound was prepared as illustrated in Example 88, step 1, starting with the appropriate indole.

EXAMPLE 90

5-((E)-{5-(Benzyloxy)-1-[2,4-bis(trifluoromethyl)benzyl]-1-1H-indol-2-yl}methylidene)-1,3-thiazolane-2,4-dione The title compound was prepared as illustrated in Example 88, step 1, starting with the appropriate indole.

EXAMPLE 91

5-{(E)-[5-(Benzyloxy)-1-(4-chlorobenzyl)-1H-indol-2-yl]methylidene}-1,3-thiazolane-2,4-dione The title compound was prepared as illustrated in Example 88, step 1, starting with the appropriate indole.

EXAMPLE 92

5-{(E)-[5-(Benzyloxy)-1-(2-naphthylmethyl)-1H-indol-2-yl]methylidene}-1,3-thiazolane-2,4-dione The title compound was prepared as illustrated in Example 88, step 1, starting with the appropriate indole.

EXAMPLE 93

5-{(E)-[1-(4-Benzylbenzyl)-5-(benzyloxy)-1H-indol-2-yl]methylidene}-1,3-thiazolane-2,4-dione The title compound was prepared as illustrated in Example 88, step 1, starting with the appropriate indole.

EXAMPLE 94

5-{(E)-[5-(Benzyloxy)-1-(4-chlorobenzyl)-1H-indol-2-yl]methylidene}-1,3-thiazolane-2,4-dione The title compound was prepared as illustrated in Example 88, step 1, starting with the appropriate indole.

EXAMPLE 95

5-((E)-{5-(Benzyloxy)-1-[2,4-bis(trifluoromethyl)benzyl]-1H-indol-2-yl}methylidene)-1,3-thiazolane-2,4-dione The title compound was prepared as illustrated in Example 88, step 1, starting with the appropriate indole.

EXAMPLE 96

2-(5-{(E)-[5-(Benzyloxy)-1-(4-{[3,5-bis(trifluoromethyl)phenoxy]methyl}benzyl)-1H-indol-2-yl]methylidene}-2,4-dioxo-1,3-thiazolan-3-yl) acetic Acid Step 1—The desired intermediate was prepared as illustrated in Example 88, step 1, starting with the appropriate indole.

EXAMPLE 97

4-[(5-{(E)-[5-(Benzyloxy)-1-(4-chlorobenzyl)-1H-indol-2yl]methylidene}2,4-dioxo-1,3-thiazolan-3-yl)methyl]benzoic Acid Step 1—The desired intermediate was prepared as illustrated in Example 88, step 1, starting with the appropriate indole.

Step 2—The desired intermediate was prepared from the above intermediate as illustrated in Example 88, step 2, using the appropriate alkylating agent.

Step 3—The title compound was prepared from the above intermediate as illustrated in Example 88, step 3.

EXAMPLE 98

2-(5-{(E)-[5-(Benzyloxy)-1-(2-naphthylmethyl)-1H-indol-2yl]methyllidene}-2,4-dioxo-1,3-thiazolan-3-yl)acetic Acid Step 1—The desired intermediate was prepared as illustrated in Example 88, step 1, starting with the appropriate indole.

Step 2—The desired intermediate was prepared from the above intermediate as illustrated in Example 88, step 2, using the appropriate alkylating agent.

Step 3—The title compound was prepared from the above intermediate as illustrated in Example 88, step 3.

EXAMPLE 99

4-[(5-{(E)-[5-(Benzyloxy)-1-(2-naphthylmethyl)-1H-indol-2-yl]methylidene}-2,4-dioxo-1,3-thiazolan-3-yl)methyl]benzoic Acid Step 1—The desired intermediate was prepared as illustrated in Example 88, step 1, starting with the appropriate indole.

Step 2—The desired intermediate was prepared from the above intermediate as illustrated in Example 88, step 2, using the appropriate alkylating agent.

Step 3—The title compound was prepared from the above intermediate as illustrated in Example 88, step 3.

EXAMPLE 100

2-(5-{(E)-[5-(Benzyloxy)-1-(4-chlorobenzyl)-1H-indol-2-yl]methylidene}-2,4-dioxo-1,3-thiazolan-3-yl)acetic Acid Step 1—The desired intermediate was prepared as illustrated in Example 88, step 1, starting with the appropriate indole.

Step 2—The desired intermediate was prepared from the above intermediate as illustrated in Example 88, step 2, using the appropriate alkylating agent.

Step 3—The title compound was prepared from the above intermediate as illustrated in Example 88, step 3.

The compounds of the following Examples 101–106 were prepared as illustrated in Example 88, step 1, starting with the appropriate indole and rhodanine.

EXAMPLE 101

5-((E)-{5-(Benzyloxy)-1-[2,4-bis(trifluoromethyl)benzyl]-1H-indol-2-yl}methylidene)-2-thioxo-1,3-thiazolan-4-one

EXAMPLE 102

5-{(E)-[5-(Benzyloxy)-1-(2-naphthylmethyl)-1H-indol-2-yl]methylidene}-2-thioxo-1,3-thiazolan-4-one

EXAMPLE 103

5-[(E)-(5-(Benzyloxy)-1-{3-[3,5-bis(trifluoromethyl)phenoxoyl]propyl}-1H-indol-2-yl)methylidene]-2-thioxo-1,3-thiazolan-4-one

EXAMPLE 104

5-{(E)-[5-(Benzyloxy)-1-(4-chlorobenzyl)-1-H-indol-2-yl]methylidene}-2-thiozo-1,3-thiazolan-4-one

GI 1418

EXAMPLE 105

5-{(E)-[1-(4-Benzylbenzyl)-5-(benzyloxy)-1H-indol-2-yl]methylidene}-2-thioxo-1,3-thiazolan-4-one

EXAMPLE 106

5-{(E)-(Benzyloxy)-1-(4-{[3,5-bis(trifluoromethyl)phenoxy]methy}benzyl-1H-indol-2-yl]methylidene}-2-thioxo-1,3-thiazolan-4-one

EXAMPLE 107

4-{[5-((E)-{5-(Benzyloxy)-1-[2,4-bis(trifluoromethyl)benzyl]-1H-indol-2-yl}methylidene)-4-oxo-2-thioxo-1,3-thiazolan-3-yl]methyl}benzoic Acid Step 1—The desired intermediate was prepared as illustrated in Example 88, step 1, starting with the appropriate indole and rhodanine.

Step 2—The desired intermediate was prepared from the above intermediate as illustrated in Example 88, step 2, using the appropriate alkylating agent.

Step 3—The title compound was prepared from the above intermediate as illustrated in Example 88, step 3.

EXAMPLE 108

5-((E)-{5-(Benzyloxy)-1-[2,4-bis(trifluoromethyl)benzyl]-1H-indol-2-yl}methylidene)-2-thioxotetrahydro-4H-imidazol-4-one The title compound was prepared as illustrated in Example 88, step 1, starting with the appropriate indole and 2-thiohydantoin

EXAMPLE 109

1-Benzyl-5-(2-thienyl)-1H-indole-2-carboxylic Acid

To a sealed tube containing 2-[5-bromo-1-benzyl-1H-indole-2carboxylic acid (100 mg, 0.303 mmol) and 2-thiopheneboronic acid (116 mg, 0.909 mmol), $(C_6H_5)_4Pd$ (42 mg, 0.036 mmol), Na₂CO₃ (2,42 mmol) in a mixture of benzene-ethanol-H₂O (5/1/2=v/v, 4.5 mL) was heated at 100° C. for 23 h. The mixture was poured onto diethyl ether and adjusted to pH 3 before extracting with diethyl ether. The organic layer was washed with NaH₂PO₄, dried over MgSO₄ and evaporated to give the crude product which was purified on silica gel column (15% EtOAc in hexane with 1% HCOOH) to give 65 mg of the product.

EXAMPLE 110

5-(1-Benzofuran-2-yl)-1-benzyl-1H-indole-2-carboxylic Acid

The title compound was prepared according to the procedure described in Example 109 except that benzo[b]fran-2-boronic acid was used.

EXAMPLE 111

1-Benzyl-5-(4-fluorophenyl)-1H-indole-2-carboxylic Acid

The title compound was prepared according to the procedure described in Example 109 except that 4-fluorophenylboronic acid was used.

EXAMPLE 112

1-Benzyl-5-(3-methoxyphenyl)-1H-indole-2-carboxylic Acid

The title compound was prepared according to the procedure described in Example 109 except that 3-methoxyphenylboronic acid was used.

EXAMPLE 113

1-Benzyl-5-phenyl-1H-indole-2-carboxylic Acid

The title compound was prepared according to the procedure described in Example 109 except that phenylboronic acid was used.

EXAMPLE 114

1-Benzhydryl-5-bromo-1H-indole-2-carboxylic Acid

To 5-bromoindole-2-carboxylic acid (1.024 g, 4.26 mmol) in 1-methyl-2-pyrrolidinone (13 mL) at 0° C. were added $^i$Pr₂NEt (25.6 mmol), tetrabutylammonium iodide (157 mg, 0.426 mmol) and bromodiphenylmethane (1.20 g, 4.86 mmol). The reaction mixture was heated at 50° C. for 21 h before partitioning between diethyl ether and ice water. After adjusting the pH to 3, the aqueous layer was extracted with diethyl ether. The organic layers were combined, washed with NaH₂PO₄, dried over MgSO₄ and evaporated to dryness. Purification on silica gel column (15% EtOAc in hexane) yielded 1.51 g (87% yield) of the product.

EXAMPLE 115

5-[3-(Acetylamino)phenyl]-1-benzhydryl-1H-indole-2-carboxylic Acid

The title compound was prepared according to the procedure described in Example 109 except that 3-acetamidobenzeneboronic acid and 1-benzhydryl-5-bromo-1H-indole-2-carboxylic acid were used.

EXAMPLE 116

1-Benzhydryl-5-(2-thienyl)-1H-indole-2-carboxylic Acid

The title compound was prepared according to the procedure described in Example 109 except that 1-benzhydryl-5-bromo-1H-indole-2-carboxylic acid and 2-thiopheneboronic acid were used.

EXAMPLE 117A 5-(Benzyloxy)-1-[2,4-bis(trifluoromethyl)benzyl]-1H-indole-2-carboxylic Acid Step 1

To an ice-cold (0° C.) solution of 2-ethoxycarbonyl-5-benzyloxyindole (5.0 g, 16.9 mmol) in dimethylformamide (50 ml) was added sodium hydride (0.62 g, 18.6 mmol). The ice bath was removed after 10 min and the reaction was stirred at rt for an addition 30 min at which time bis (trifluoromethyl)benzyl bromide (3.8 ml, 20.3 mmol) was added dropwise. The green mixture was stirred at rt for 4 h, water was added and the mixture was extracted with EtOAc. The combined organic layers were washed with brine, dried over MgSO₄ and concentrated. The product was recrystallized from EtOAc/Hex to afford 6.87 g (81%) of the desired intermediate as an off-white powder.

Step 2

To a solution of the above intermediate (1.3 g, 2.5 mmol) in THF (50 ml) was added 1N NaOH (5 ml) and MeOH (6 ml). The mixture was stirred overnight at rt and then concentrated. The residue was suspended in water and acidified with HOAc. The product was extracted with EtOAc, the combined organic layers were washed with brine, dried over MgSO₄ and concentrated to afford a quantitative yield of the title compound as an off-white solid.

EXAMPLE 117B

5-[({5-(Benzyloxy)-1-[2,4-bis(trifluoromethyl) benzyl]-1H-indol-2-yl}carbonyl)amino]-2-[(5-chloro-3-pyridinyl)oxy]benzoic Acid Step 1

To a solution of the title compound above (0.4 g, 0.8 mmol) in CH₂Cl₂ (5 ml) and a few drops of DMF was added oxalyl chloride (0.2 ml, 2.4 mmol). The reaction was stirred for 1.5 h and concentrated. The resulting yellow residue was dissolved in CH₂Cl₂ (2 ml) and added to a solution of the pyridyl aminobenzoate ether (0.24 g, 0.8 mmol) and pyridine (0.1 ml, 0.9 mmol) in CH₂Cl₂ (8 ml). The reaction was stirred overnight at rt, water was added and the product was extracted with CH₂Cl₂. The combined organic layers were washed with saturated aqueous NH₄Cl, water, brine and dried over MgSO₄. Concentration and flash chromatography (Hex/EtOAc, 3/2) afforded 0.182 g (51%) of the desired intermediate as a tan solid.

Step2

To a solution of the above intermediate (0.136 g, 0.2 mmol) in TBF (3 ml), was added LiOH (0.022 g, 0.5 mmol) and water (0.5 ml). The mixture was stirred overnight at rt, concentrated and the resulting residue was suspended in water and acidified with HOAc. The product was extracted with EtOAc, the combined organic layers were washed with water, brine and dried over MgSO₄. Concentration gave 0.122 g of the title compound (94%) as a white crystalline solid.

EXAMPLE 117C 5-(Benzyloxy)-1-(4-{[3,5-bis(trifluoromethyl) phenoxy]methyl}benzyl)-1H-indole-2-carboxylic Acid The procedure in EXAMPLE 117A steps 1 and 2 were followed using 2-ethoxycarbonyl-5-benzyloxyindole (2.0 g, 3.2 mmol) and the appropriate alkylating reagent to afford 1.7 g (41% for 2 steps) of the title compound as a yellow solid.

EXAMPLE 117D 5-(Benzyloxy)-1-(4-{[3,5-bis(trifluoromethyl) phenoxy]methyl}benzyl)-1H-indole-2-carboxylic Acid The procedure in EXAMPLE 117A steps 1 and 2 were followed using 2-ethoxycarbonyl-5-benzyloxyindole (2.0 g, 3.2 mmol) and the appropriate alkylating reagent to afford 1.7 g (41% for 2 steps) of the title compound as a yellow solid.

EXAMPLE 118

5-(Benzyloxy)-1-[2,4-bis(trifluoromethyl)benzyl]-2-(1H-1,2,3,4-tetraazol-5-yl)-1H-indole Step 1

To a suspension of the acid prepared in Example 117A (1.5 g, 3.0 mmol) in $CH_2Cl_2$ (20 ml) was added oxalyl chloride (0.8 ml, 9.1 mmol) and three drops of DMF. The mixture became homogeneous and was stirred for 1 h at rt. The reaction was concentrated and redissolved in $CH_2Cl_2$ (5 ml) and $NH_4OH$ (2.0 ml) was added. The biphasic mixture was stirred for 24 h and concentrated. The remaining aqueous residue was extracted with $CH_2Cl_2$ and the combined organic layers washed with brine, dried and concentrated to give 1.4 g (95%) of the desired intermediate as a yellow powder.

Step 2

To an ice-cold solution of DMF (0.23 ml, 3.0 mmol) in $CH_3CN$ (10 ml) was added oxalyl chloride (0.24 ml, 0.28 mmol). A white precipitate formed immediately and the solution was stirred for an additional 5 min. A solution of the above intermediate (1.2 g, 2.5 mmol) in $CH_3CN$ (5 ml) was added. The resulting yellow-orange solution was stirred for 10 min and pyridine (0.44 ml, 5.5 mmol) was added. After 5 min the red mixture was partitioned between 10% aqueous HCl and EtOAc. The organic layer was dried and concentrated to give 1.0 g (84%) of the desired intermediate as a yellow powder.

Step 3

GI 1563

5-(Benzyloxy)-1-(4-{[3,5-bis(trifluoromethyl) phenoxy]methyl}benzyl)-1H-2-carboxylic Acid To a solution of the above intermediate (0.94 g, 2.0 mmol) in N-methyl-2-pyrrolidinone (10 ml) was added sodium azide (0.39 g, 5.9 mmol). The mixture was heated at reflux for 2 h. The reaction was allowed to cool to rt and poured into 50 ml of ice water. The resulting solution was adjusted to pH=2 with 10% aqueous HCl and a tan precipitate formed. The mixture was filtered and washed with EtOAc. Flash chromatography ($CH_2Cl_2$/MeOH, 10:1) gave 0.78 g (78%) of the title compound as a white powder.

EXAMPLE 119 benzyl 1-(4-{[3,5-bis(trifluoromethyl)phenoxy] methyl}benzyl)-2-(1H-1,2,3,4-tetraazol-5-yl)-5-1H-indol-5-yl ether acid was prepared in an analogous manner to Example 118 according to steps 1–3 starting from the acid prepared in EXAMPLE 117C.

EXAMPLE 120

4-{[5-((E)-{5-(Benzyloxy)-1-[2,4-bis(trifluoromethyl)benzyl]-1H-indol-2-yl}methylidene)-4-oxo-2-thioxo-1,3-thiazolan-3-yl]methyl}benzoic Acid Step 1

The thiasolidinedione prepared in Example 101 (0.1 g, 0.2 mmol), was alkylated by treatment with sodium hydride (0.006 g, 0.22 mmol), and the bromomethyl SEM ester (0.058 g, 0.2 mmol) in DMF (2 ml). Flash chromatography (Hex/EtOAc, 4/1) gave 0.073 g (50%) of the desired intermediate as a thick oil.

Step 2

To a solution of the above intermediate (0.07 g, 0.1 mmol) in $CH_3CN$ (5 ml) was added aqueous 48% HF (2 ml). After 2 h water was added and the product was extracted with EtOAc, the combined organic layers were washed with water, brine and dried over $MgSO_4$. Concentration gave 0.025 g of the title compound (42%) as an orange powder.

EXAMPLE 121

5-((Z,2E)-3-{5-(Benzyloxy)-1-[2,4-bis(trifluoromethyl)benzyl]-1H-indol-2-yl}-2-propenylidene)-1,3-thiazolane-2,4-dione Step 1

A solution of the intermediate prepared in EXAMPLE 117A, step 1 (4.4 g, 8.4 mmol) in THF (30 ml) was cooled to 0° C. and a solution of lithium aluminum hydride in THF (1.0M, 8.4 ml) was added dropwise with vigorous stirring. After 1 h at 0° C. the reaction was carefully quenched with a saturated solution of $NH_4Cl$. The salts were filtered and washed with EtOAc. Concentration of the solvents afforded 3.9 g (96%) of the alcohol as a yellow foam. The alcohol (1.6 g, 3.3 mmol) was dissolved in THF (50 ml) and MnO2 (2.91 g, 33.4 mmol) was added. The reaction was stirred for 12 h and filtered through a pad of Celite. Concentration of the filtrate gave 1.47 g (92%) of the desired intermediate as a thick clear oil.

Step 2

To an ice-cold solution of trimethylphosphonoacetate (0.5 ml, 3.1 mmol) in DMF (10 ml) was added sodium hydride (0.14 g, 3.4mmol) and the reaction was stirred for 20 min. A solution of the above intermediate (1.47 g, 3.1 mmol) DMF (3 ml) was added, the ice bath was removed and the reaction was allowed to stir overnight at rt. Water was added and the aqueous phase was extracted with EtOAc. The organic layer was washed with water, brine, dried over magnesium sulfate and concentrated. Flash chromatography (Hex/EtOAc, 3/2) provided 1.5 g (93%) of the desired intermediate as a yellow solid.

Step 3

The above intermediate (0.5 g, 0.9 mmol) was dissolved in $CH_2Cl_2$ (10 ml) and the solution was cooled to −20° C. A solution of diisobutylaluminium hydride (10M in toluene, 1.9 ml) was added dropwise, and the reaction was allowed to stir at rt overnight. Water was added, and the mixture was filtered through a pad of celite. The filtrate was diluted with EtOAc, washed with water and the combined organic layers washed with brine, dried and concentrated. Flash chromatography (Hex/EtOAc, 3/2) gave 0.49 g (75%) of an orange solid. This material was dissolved in THF (12 ml) and MnO2 (1.1 g, 12.3 mmol) was added. The mixture was stirred overnight and filtered through a pad of Celite. Concentration of the solvent afforded 0.4 g (65%) of the desired intermediate as a thick tan oil.

Step 4

The above intermediate (0.1 g, 0.2 mmol) was dissolved in toluene (1 ml), followed by piperidine (6 µl, 0.1 mmol) acetic acid (1.2 µl) and 2,4-thiazolidinedione (0.023 g, 0.2 mmol). The mixture was heated to reflux for 2 h. The reaction was allowed to cool to rt, water was added and the aqueous layer was extracted with EtOAc. The combined organic layers were washed with water and brine, dried and concentrated. Flash chromatography (Hex/EtOAc, 3/2) gave 0.056 g (47%) of the title compound as a red powder.

EXAMPLE 122

5-(Benzyloxy)-1-(4-{[3,5-bis(trifluoromethyl) phenoxyl]methyl}benzyl)-1H-indole-2-carboxylic Acid Step 1: To ethyl 5-benzyloxy-2-indolcarboxylate (1 g, 3.4 mmol) in 12 ml of DMF, sodium hydride (0.163 g, 60% oil dispersion, 4.07 mmol) is added at room temperature. The reaction is stirred for 30 minutes. a-Bromo-a'-[3,5-bis (trifluoromethyl)phenoxyl]-p-xylene (1.54 g, 3.73 mmol) is added at this time and the reaction stirred overnight. On completion of the reaction (monitored by TLC) it is quenched with water, extracted with ethyl acetate (3×). Organic layers are dried over magnesium sulfate, concentrated and used for the next step.

Step 2: The ester (2.1 g, 3.39 mmol) is dissolved in 40 mL of 1/1 THF/methanol and then 1N sodium hydroxide (15 mL) is added and the resulting mixture is stirred for 16 hours at RT, workup gave crude product that is purified via chromatography (1:1 Hexane:Ethyl acetate with 1% acetic acid) to yield (1.73 g, 85%) of solid.

EXAMPLE 123

5-({[1-Benzyl-5-(benzyloxy)-1H-indol-2-yl] carbonyl}amino)isophthalic Acid

Step 1: This intermediate was prepared according to the procedure described in Example 122, but using benzyl bromide.

Step 2: The acid (0.27 g, 0.75 mmol) prepared in step 1, EDCI (0.18 g, 0.97 mmol), DMAP (3 mg, 0.02 mmol) and dimethyl-5 aminoisophthalate (0.18 g, 0.75 mmol) were dissolved in THF (8.8 mL) and refluxed for 16 hours, after workup and purification (Hexane:Ethyl Acetate 3:1) yielded (0.25 g, 60%) of pure product.

Step 3: The title compound was prepared from ester, prepared in step 2 above, according to the procedure described in step 2, Example 122.

EXAMPLE 124

(E)-3-[5-(Benzyloxy)-1-(2-naphthylmethyl)-1H-indol-2-yl]-2-propenoic Acid

Step 1: Ethyl 5-benzyloxy-2-indolcarboxylate (30 g, 102 mmol) is dissolved in 250 mL of THF and cooled to 0° C. and Lithium Aluminum Hydride (LAH) (255 mL of a 1.0 M solution in THF) is added via addition funnel over 40 minutes. The reaction was stirred a further 2 hours at 0° C. and then worked up by the addition of 4N NaOH (190 mL). The resulting salts are filtered and washed with ethyl acetate (3×400 mL), the filtrates are combined and dried over $MgSO_4$ and concentrated to yield 24.8 g (96%).

Step 2: Indole alcohol (26.1 g, 103 mmol) from step 1 is dissolved in THF (900 ml). Manganese dioxide (106.6 g) is added and the mixture is stirred for 2 h at room temperature. After the reaction is complete the mixture is filtered through celite and washed with ethyl acetate. The filtrate is concentrated under reduced pressure, dried to give the desired aldehyde (22.9 g, 89%).

Step 3: This intermediate was prepared from indole, prepared in step 2 above and 2-(bromomethyl)naphthalene, according to the procedure described in step 1, Example 122.

Step 4: To sodium hydride (0.025 g, 60% oil dispersion, 0.63 mmol) in 7.5 mL of THF is added trimethyl phosphonoacetate (0.1 mL, 0.62 mmol) in 2.5 mL of THF at room temperature. The reaction is stirred for 10 minutes. Next the aldehyde (0.24 g, 0.62 mmol) prepared in step 3 above in 2.5 mL THF is added dropwise at room temperature. Reaction is stirred for another 30 minutes

EXAMPLE 133

2-{[3-Acetyl-1-[4-(1,3-benzothiazol-2-ylcarbonyl) benzyl]-5-(benzyloxy)-1H-indol-2-yl] methyl}sulfanyl)acetic Acid Step 1 p-Toluoyl chloride (0.8 M) was added to triethylamine (2.44 eq) and methoxymethyl amine HCl (1.1 eq) dissolved in methylene chloride at 0° C. over 20 min. The reaction was allowed to warm to 25° C. After stirring at 25° C. for 1 day, workup with methylene chloride and water afforded crude product in ca. 100% yield.

Step 2 Under anhydrous conditions benzothiazole was dissolved in THF (0.35 M). At −78° C. added BuLi (1.1 eq). After 1 h at −78° C., added the amide from step 1 in THF, over 15 min. The reaction was allowed to warm to 25° C. After stirring at 25° C. for 1 day, workup with ethyl acetate and water and chromatography afforded pure tolyl ketone product (52%).

Step 3 The tolyl ketone from step 2 was dissolved in carbon tetrachloride (0.19M), and NBS (1.2 eq) and AIBN (0.11 eq) were added. After 1 d at 60° C., about 1:1 of starting material and product were present. Resubmission under the same conditions, followed by filtration and recrystallization from ethyl acetate afforded pure bromobenzyl ketone product (28%).

Step 4 The intermediate from step 3, Example 131 was dissolved in dry DMF (0.1 M), followed by NaH (1.2 eq). After 1.5 h at 25° C., added the bromobenzyl ketone from step 3 and stirred for 1 d at 25° C. Workup (ethyl acetate/ hexanes) and trituration (ethyl acetate/hexanes) afforded the product in 46% yield.

Step 5: The product from step 4 was dissolved in methylene chloride and 1 N HCl (ca. 0.04 M) and stirred at 25° C. for 1 h. Workup (sodium bicarbonate), and trituration with ether afforded the product alcohol (89%).

Step 6: The alcohol from step 5 was dissolved in dry methylene chloride (0.014 M), treated with thionyl chloride (1.2 eq) and stirred at 25° C. for 1 d. Concentration and trituration with ethyl acetate/hexanes afforded the product chloride (100%).

Activity data for the compounds of Examples 88–135 are reported in Table VIII (assay described in Example 136).

EXAMPLE 136

Activity Assays (a) Vesicle Assay 1-palmitoyl-2-V$^{14}$C] arachidonyl phosphotidylcholine (58 mCi/mmol) (final concentration 6 µM) and 1,2- dioleyolglycerol (final concentration 3 μM) were mixed and dried under a stream of nitrogen. To the lipids was added 50 mM Hepes pH 7.5 (2×final concentration of lipids) and the suspension was sonicated for 3 min. at 4° C. To the suspension was added 50 mM Hepes pH 7.5, 300 mM NaCl, 2 mM DTT, 2 mM $CaCl_2$ and 2 mg/ml bovine serum albumin (BSA) (Sigma A7511) (1.2×final concentration of lipids). A typical assay consisted of the lipid mixture (85 μl) to which was added consecutively, the inhibitor (5 μl in DMSO) and $cPLA_2$, 10 ng for an automated system or 1 ng for a manual assay, in 10 μl of the BSA buffer. This assay was conducted by either the manual assay or automated assay protocol described below.

(b) Soluble Substrate Assay (LysoPC)

1-[$^{14}$C]-palmitoyl-2-hydroxyphosphotidyl-choline (57 mCi/mmol) (final concentration 4.4 μM) was dried under a stream of nitrogen. The lipid was resuspended by vortexing 80 mM Hepes pH 7.5, 1 mM EDTA (1.2×final concentration). A typical assay consisted of lipid suspension (85 μl) to which was added consecutively the inhibitor (5 μl in DMSO) and $cPLA_2$, 200 ng in 80 mM Hepes pH 7.5, 2 mM DTT and 1 M EDTA. This assay was conducted by either the manual assay or automated assay protocol described below.

(f) RBL Assay

RBL-2H3 cells were routinely cultured as 37° C. in a 5% $CO_2$ atmosphere in minimal essential medium containing nonessential amino acids and 12% fetal calf serum. The day before the experiment, cells were seeded into spinner flasks at $3 \times 10^5$ cells/ml and 100 ng/ml DNP specific-IgE was added. After 20 hrs, the cells were harvested by centrifugation and washed once in serum-free minimal essential media, and resuspended to $2 \times 10^6$ cells/ml in serum free media. The cells were then preincubated with either inhibitor in DMSO (1% v/v) or DMSO (1% v/v) for 15 min at 37° C. followed by stimulation with DNP-BSA (300 ng/ml). After 6 min, the cells were removed by centrifugation, and the supernatant was assayed for $PGD_2$ content in accordance with known methods.

(g) Coumarine Assay 7-hydroxycoumarinyl 6-heptenoate was used as a monomeric substrate for cPLA2 as reported previously (Huang, Z. et al., 1994, Analytical Biochemistry 222, 110–115). Inhibitors were mixed with 200 μL assay buffer (80 mM Hepes, pH 7.5, 1 mM EDTA) containing 60 μM 7-hydroxycoumarinyl 6-heptenoate. The reaction was initiated by adding 4 μg cPLA2 in 50 μL assay buffer. Hydrolysis of the 7-hydroxycoumarinyl 6-heptenoate ester was monitored in a fluorometer by exciting at 360 nm and monitoring emission at 460 nm. Enzyme activity is proportional to the increase in emission at 460 nm per minute. In the presence of a cPLA2 inhibitor, the rate of increase is less.

EXAMPLE 137

Rat Carrageenan-Induced Footpad Edema Test

Each compound was suspended in 0.3 ml absolute ethanol, 0.1 ml Tween-80 and 2.0 ml Dulbecco's PBS (without calcium or magnesium). To this mixture, 0.1 ml 1N NaOH was added. After solution was complete, additional amounts of PBS were added to adjust the concentration to 1 mg/ml. All comounds remained in solution. Compounds were administered i.v. in a volumne of 5 ml/kg to male Sprague Dawley rats at the same time that edema was induced by injection of 0.05 ml of 1% Type IV carrageenan into the hind footpad. Footpad volume was measured before dosing with compound and 3 hours after dosing with carageenan.

TABLE VIII

| Example | Structure | PERCENT INHIBITION @ | CONCEN- TRATION (micromolar) |
|---|---|---|---|
| 88 | 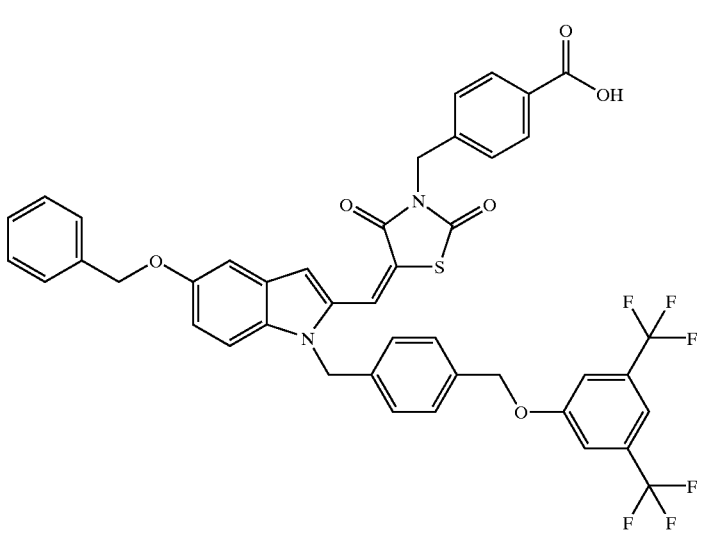 | 68<br>50 | 6.25<br>3 |

TABLE VIII-continued

| Example | Structure | PERCENT INHIBITION @ | CONCEN- TRATION (micromolar) |
|---|---|---|---|
| 89 | 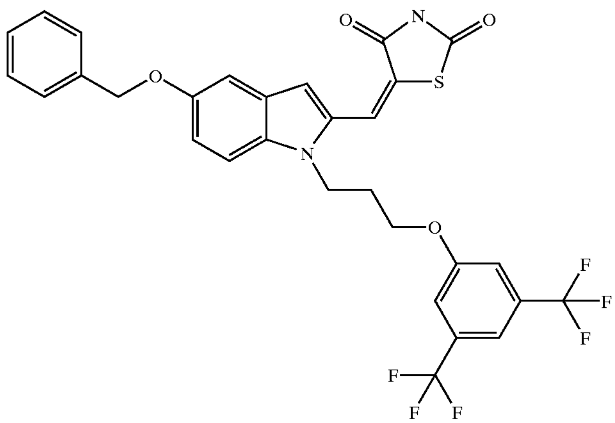 | 50<br>50<br>50 | 22<br>24<br>37 |
| 90 | 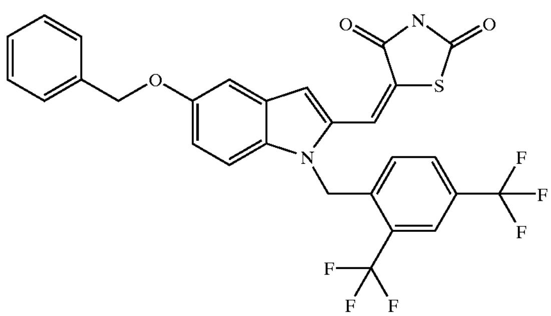 | 50<br>50<br>50<br>50<br>50 | 30<br>23<br>24<br>28<br>38 |
| 91 | 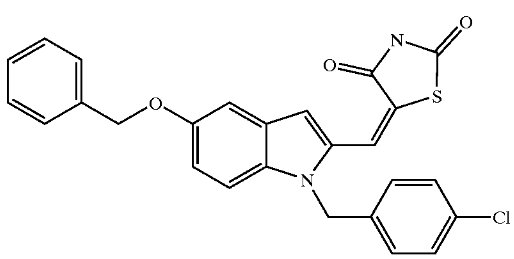 | 50<br>50 | 18<br>25 |
| 92 | 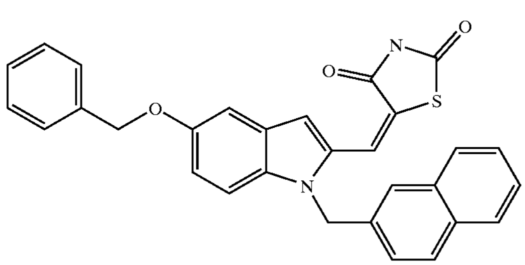 | 50<br>50 | 18<br>22 |

TABLE VIII-continued

| Example | Structure | PERCENT INHIBITION @ | CONCEN- TRATION (micromolar) |
|---|---|---|---|
| 93 | 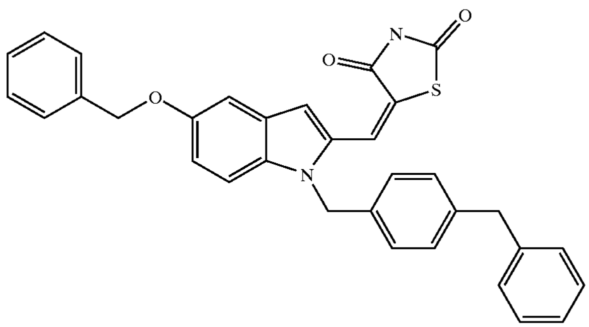 | 50<br>55 | 12.5<br>12.5 |
| 96 | 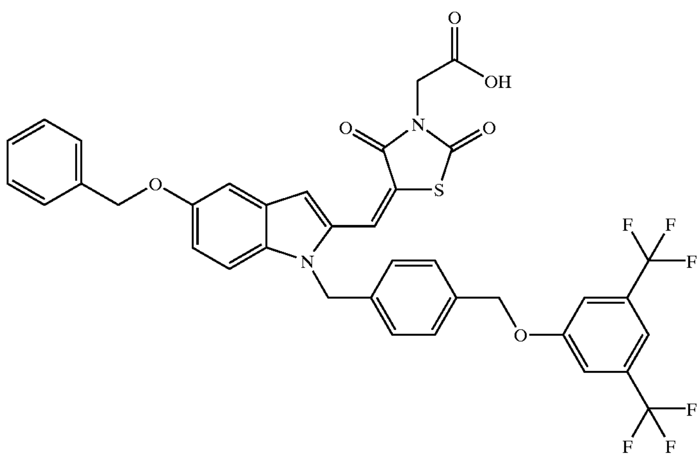 | 57<br>50 | 6.25<br>5 |
| 97 | 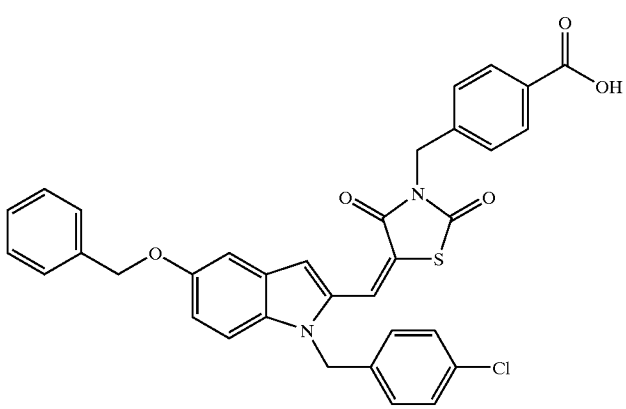 | 56<br>50 | 6.25<br>4.5 |

TABLE VIII-continued

| Example | Structure | PERCENT INHIBITION @ | CONCENTRATION (micromolar) |
|---------|-----------|----------------------|----------------------------|
| 98 | 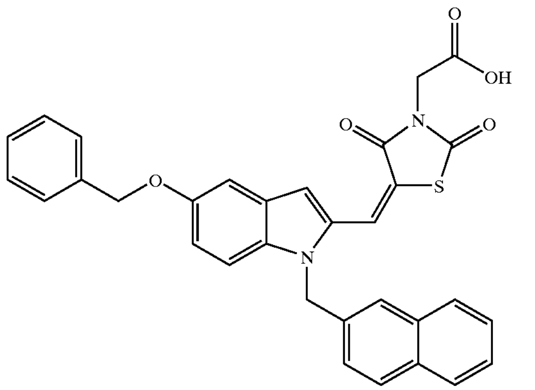 | 50<br>50<br>50<br>50<br>50<br>50 | 37<br>45<br>42<br>25<br>33<br>37 |
| 99 | 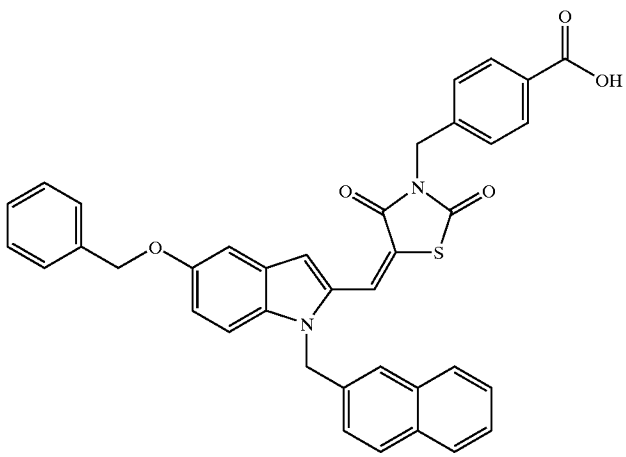 | 50<br>50 | 9<br>12 |
| 100 | 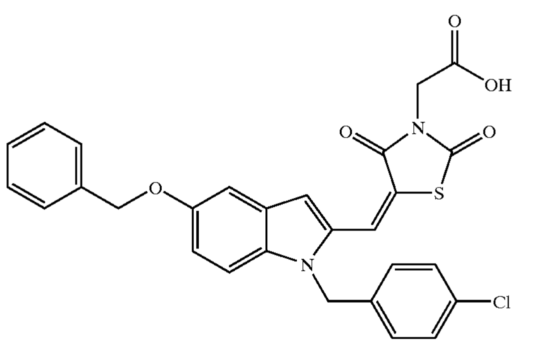 | 50<br>50 | 7<br>9 |
| 101 | 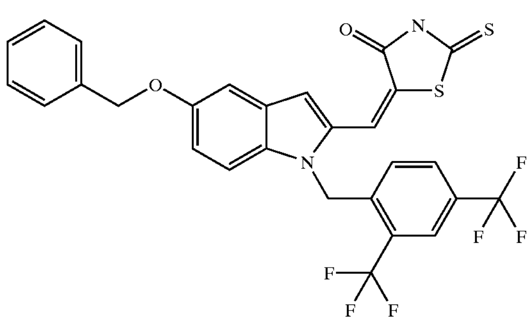 | 50<br>50<br>50<br>50<br>50<br>50<br>50 | 9.5<br>10<br>12.5<br>14<br>17<br>22<br>10 |

TABLE VIII-continued

| Example | Structure | PERCENT INHIBITION @ | CONCENTRATION (micromolar) |
|---|---|---|---|
| 102 | 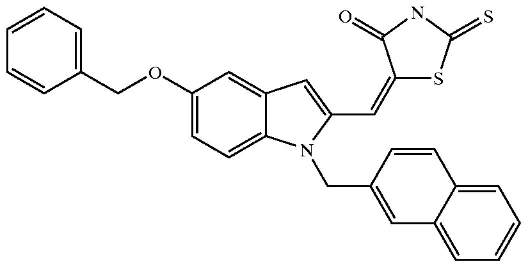 | 50<br>50<br>50 | 16<br>18<br>25 |
| 103 | 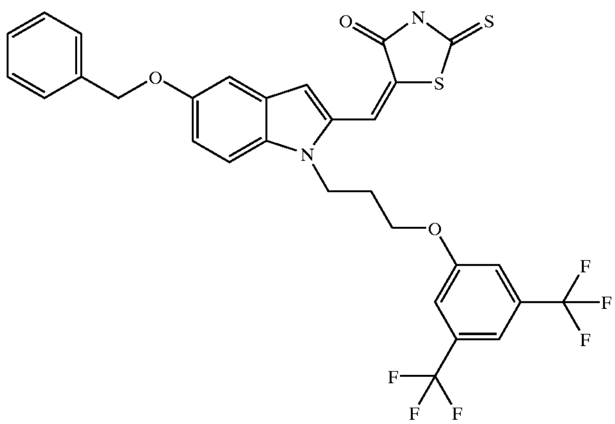 | 50<br>50<br>50 | 15<br>16<br>22 |
| 104 | 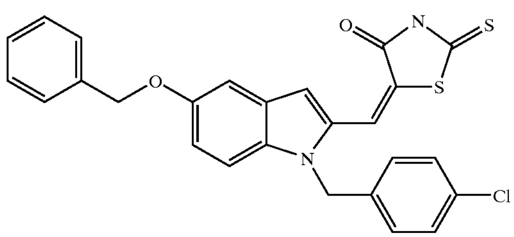 | 50<br>50<br>50<br>50<br>50<br>50 | 17<br>20<br>12<br>12<br>14<br>18 |
| 105 | 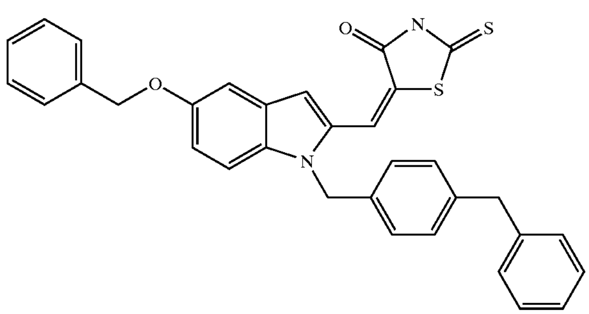 | 50<br>50 | 18<br>16 |

TABLE VIII-continued

| Example | Structure | PERCENT INHIBITION @ | CONCENTRATION (micromolar) |
|---------|-----------|----------------------|----------------------------|
| 106 | 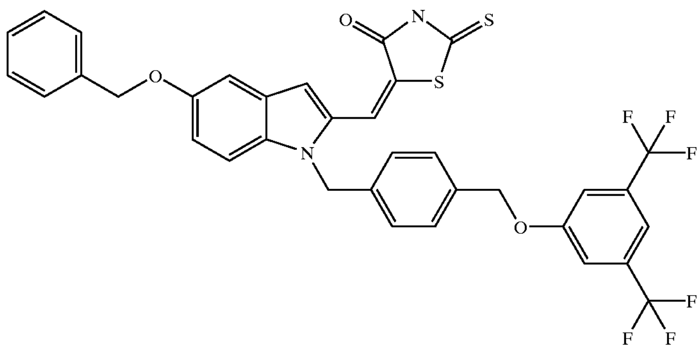 | 50<br>50 | 9<br>12.5 |
| 107 | 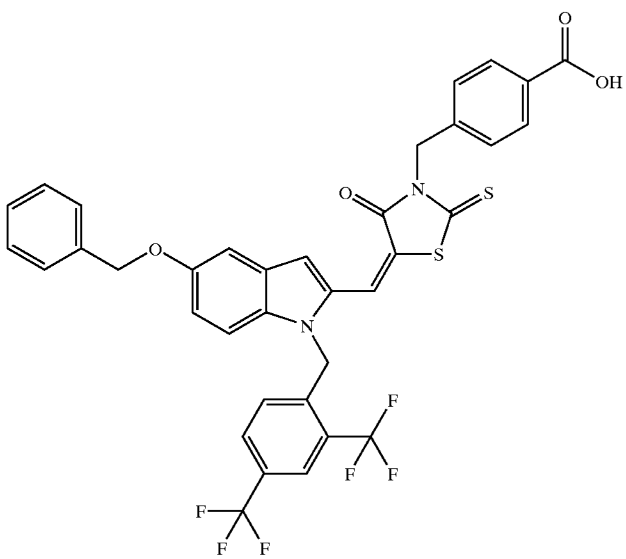 | 50<br>67 | 3.8<br>6.2 |
| 108 | 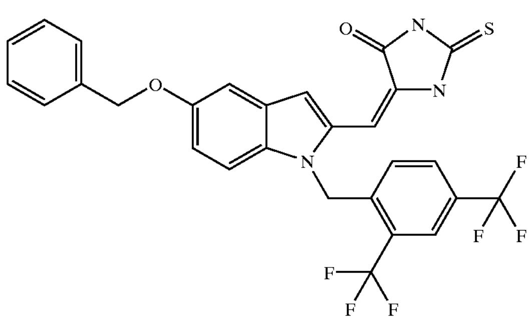 | 50<br>50 | 32<br>39 |
| 109 | 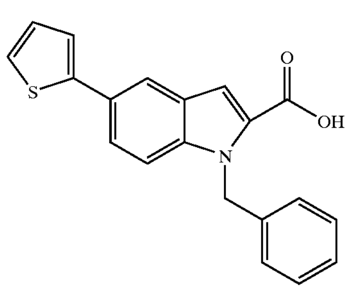 | 50<br>50 | 50<br>55 |

TABLE VIII-continued
| Example | Structure | PERCENT INHIBITION @ | CONCENTRATION (micromolar) |
|---|---|---|---|
| 110 | 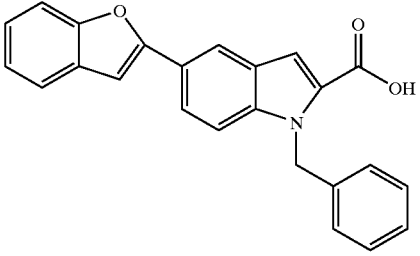 | 50<br>50 | 50<br>50 |
| 111 | 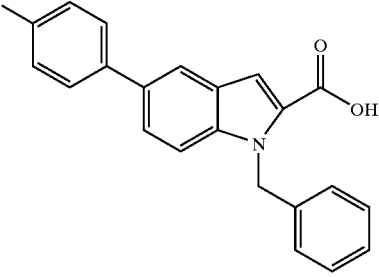 | 50 | 13 |
| 112 | 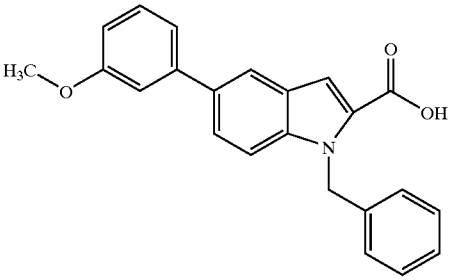 | 50<br>32<br>46<br>50 | 12.5<br>25<br>50<br>50 |
| 113 | 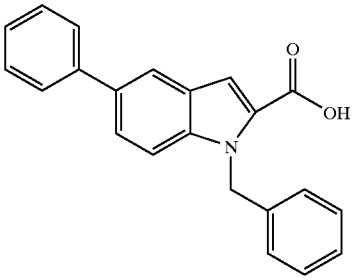 | 38<br>50 | 100<br>170 |
| 114 | 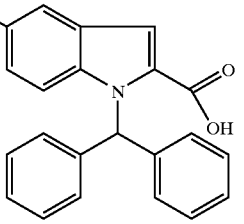 | 50<br>50 | 40<br>42 |

TABLE VIII-continued

| Example | Structure | PERCENT INHIBITION @ | CONCEN- TRATION (micromolar) |
|---------|-----------|----------------------|------------------------------|
| 115 | 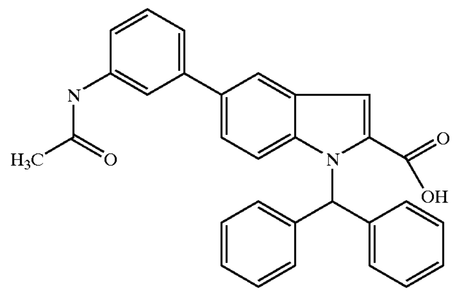 | 50<br>50 | 30<br>35 |
| 116 | 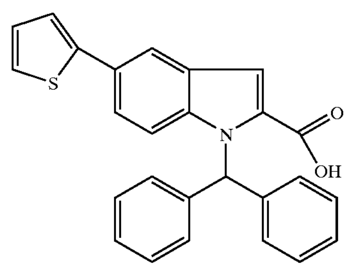 | 50<br>50 | 60<br>70 |
| 117A | 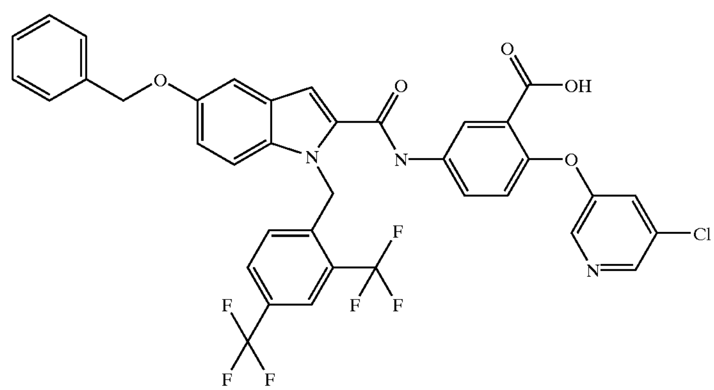 | 50<br>39 | 28<br>50 |
| 117B | 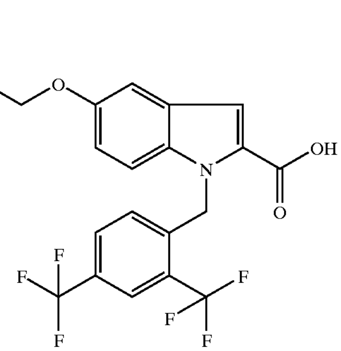 | 50<br>50<br>50<br>50 | 34<br>34<br>43<br>43 |

TABLE VIII-continued

| Example | Structure | PERCENT INHIBITION @ | CONCEN- TRATION (micromolar) |
|---|---|---|---|
| 117C | 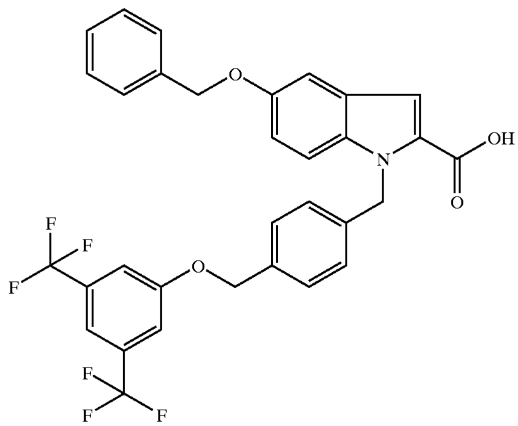 | 50<br>50<br>50 | 9<br>4<br>8.5 |
| 118 | 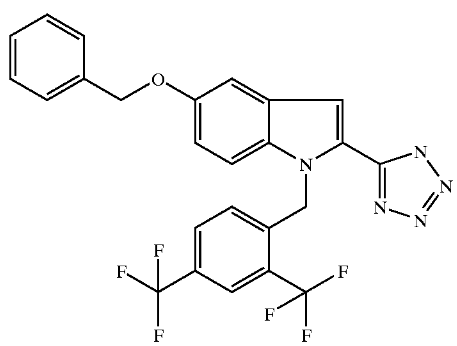 | 50<br>50 | 12<br>15 |
| 119 | 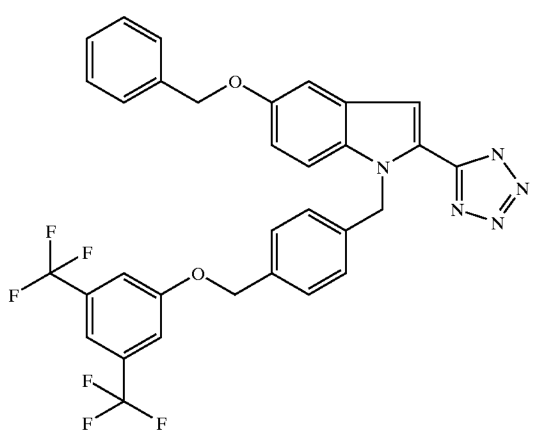 | 50<br>50<br>50 | 5<br>4<br>6 |

TABLE VIII-continued
| Example | Structure | PERCENT INHIBITION @ | CONCENTRATION (micromolar) |
|---|---|---|---|
| 120 | 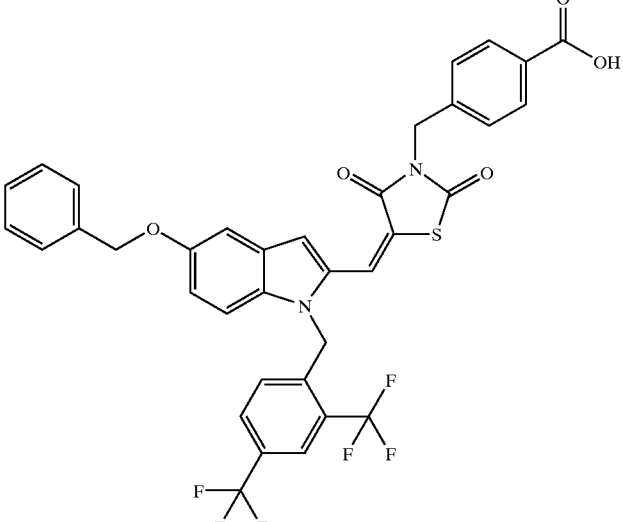 | 50<br>67<br>50<br>67 | 3.8<br>6.2<br>3.8<br>6.2 |
| 121 | 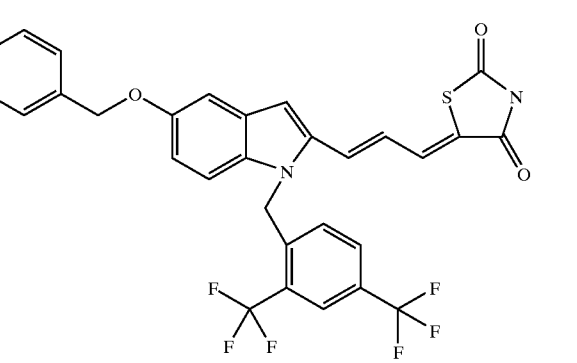 | 50<br>50 | 18.5<br>20 |
| 122 | 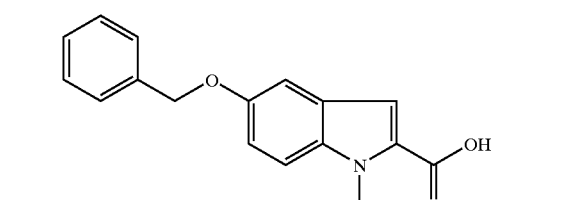 | 50<br>50 | 3.75<br>10 |

TABLE VIII-continued
| Example | Structure | PERCENT INHIBITION @ | CONCEN- TRATION (micromolar) |
|---|---|---|---|
| 123 | 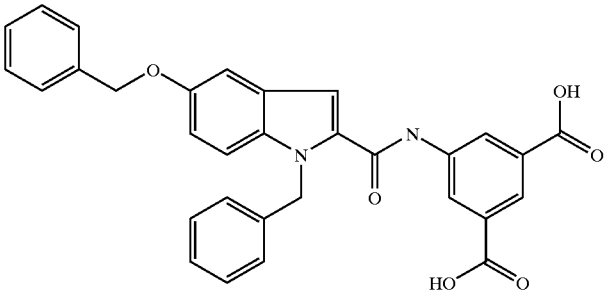 | 31<br>25 | 50<br>50 |
| 124 | 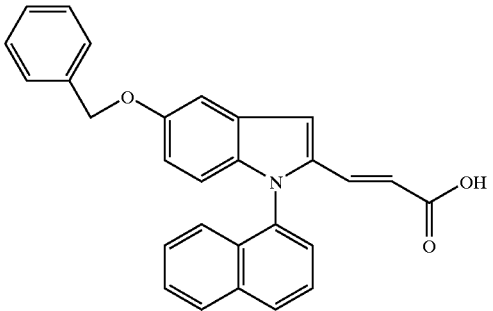 | 50<br>50 | 12.5<br>15 |
| 125 | 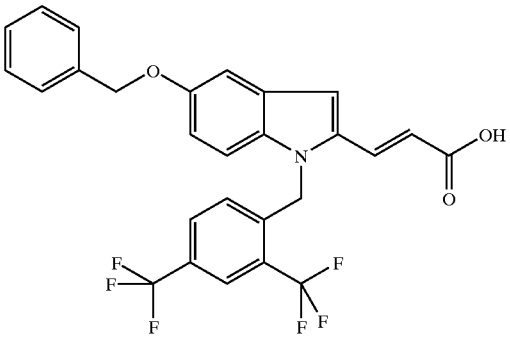 | 50 | 23 |
| 126 | 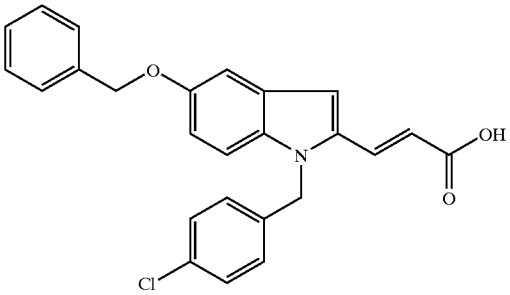 | 50<br>50 | 17<br>18 |

TABLE VIII-continued

| Example | Structure | PERCENT INHIBITION @ | CONCENTRATION (micromolar) |
|---------|-----------|----------------------|----------------------------|
| 127 | 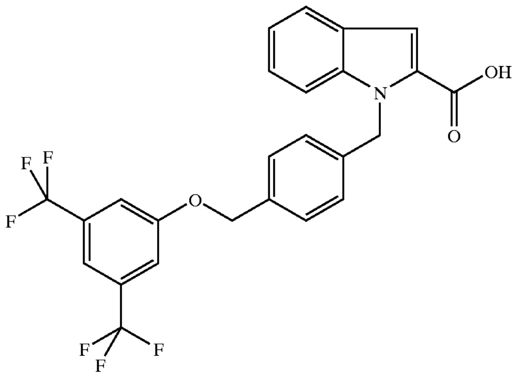 | 50<br>50 | 28<br>86 |
| 128 | 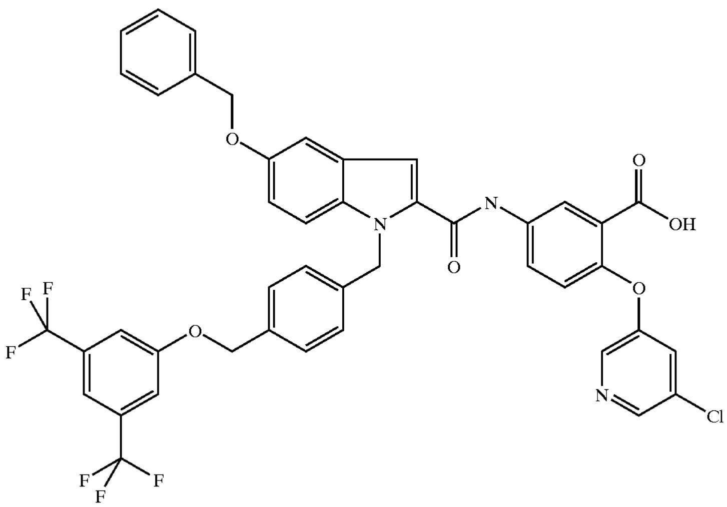 | 50<br>50<br>50<br>52<br>50 | 5<br>6<br>8.5<br>12.5<br>44 |
| 129 | 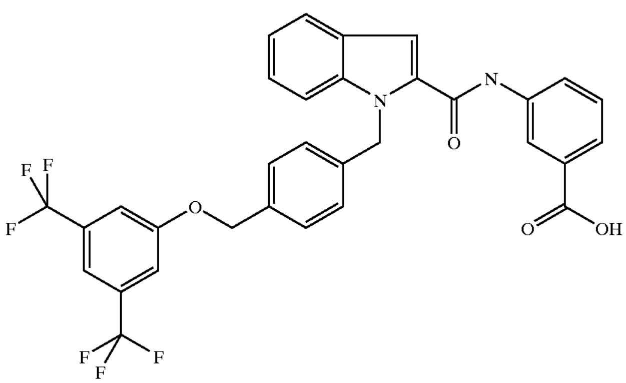 | 50<br>50<br>50<br>50<br>95<br>50 | 2.5<br>4<br>3.5<br>3.8<br>12.5<br>30 |

TABLE VIII-continued

| Example | Structure | PERCENT INHIBITION @ | CONCEN- TRATION (micromolar) |
|---------|-----------|----------------------|------------------------------|
| 130 | 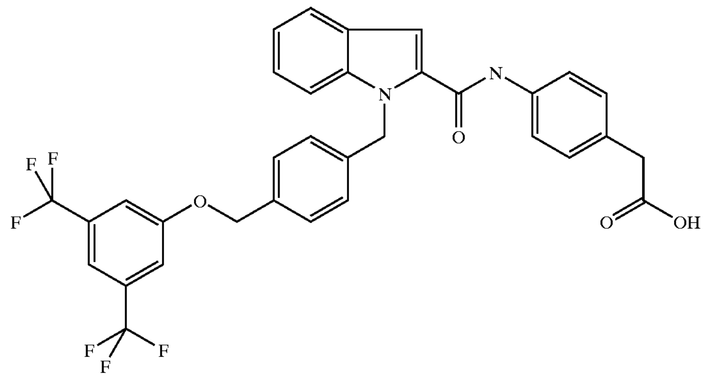 | 50<br>50<br>50<br>50<br>50<br>50<br>50 | 12<br>80<br>10<br>16<br>32<br>44<br>50 |
| 131 | 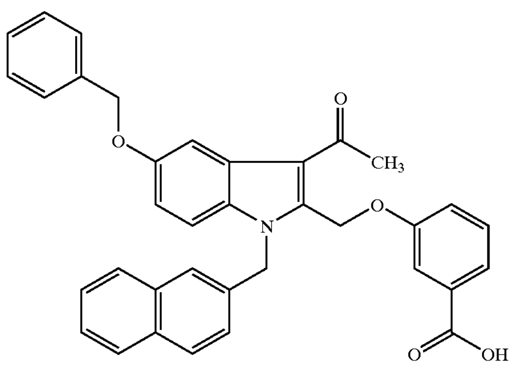 | 50<br>50 | 7<br>46 |
| 132A | 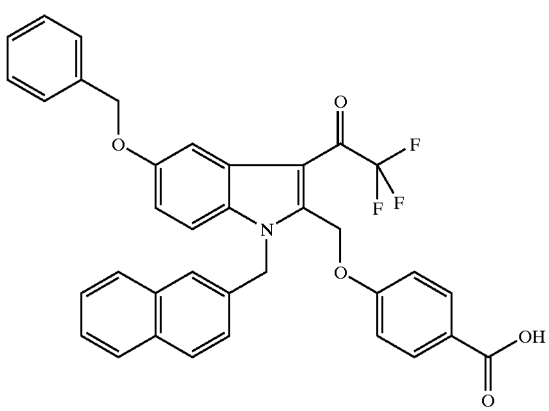 | 50<br>50<br>50 | 9<br>17<br>30 |

TABLE VIII-continued

| Example | Structure | PERCENT INHIBITION @ | CONCENTRATION (micromolar) |
|---|---|---|---|
| 132B | 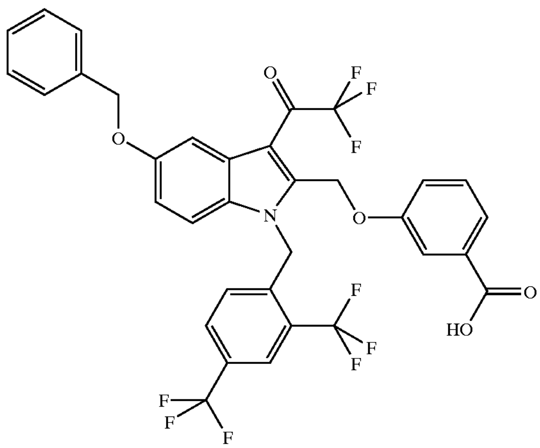 | 50<br>50 | 19<br>20 |
| 133 | 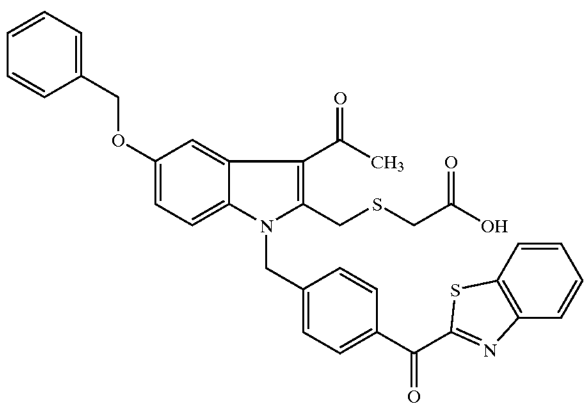 | 50 | 8.5 |
| 134 | 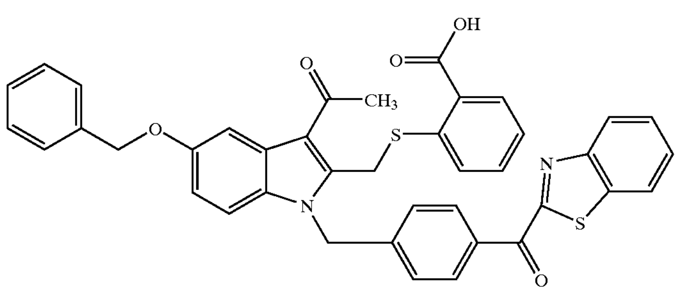 | 50 | 3.5 |

TABLE VIII-continued

| Example | Structure | PERCENT INHIBITION @ | CONCENTRATION (micromolar) |
|---|---|---|---|
| 135 | 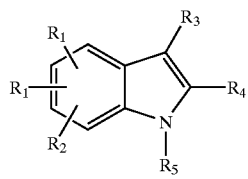 | 50 | 9 |

All patent and literature references cited herein are incorporated as if fully set forth herein.

What is claimed:

1. A compound of the formula:

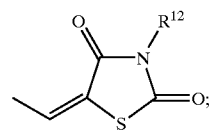

wherein:

$R_1$ and $R_{1'}$ are independently selected from the group consisting of H, $C_1$-$C_6$ alkyl, —Z—$C_1$-$C_6$ alkyl, phenyl, —$(CH_2)_n$—Z—$(CH_2)_n$-phenyl, benzyl, —$(CH_2)_n$—Z—$(CH_2)_n$-benzyl, naphthyl, —$(CH_2)_n$—Z—$(CH_2)_n$-napthyl, pyrimidinyl, and —$(CH_2)_n$—Z—$(CH_2)_n$-pyrimidinyl, wherein the alkyl, phenyl, benzyl, napthyl and pyrimidinyl groups may be optionally substituted by from 1 to 3 substituents selected from halogen, $C_1$-$C_6$ alkyl, $C_1$-$C_6$ alkoxy, —$NO_2$, —$NH_2$, —CN, —$CF_3$, and —OH;

Z is O or S;

n is an integer from 0 to 3;

$R_2$ is selected from the group consisting of H, halogen, —$CF_3$, —OH, —$C_1$-$C_{10}$ alkyl, $C_1$-$C_{10}$ alkoxy, —CHO, —CN, —$NO_2$, —NH2, —NH—$C_1$-$C_6$ alkyl, —N($C_1$-$C_6$ alkyl)$_2$, —NH—$SO_2$—$C_1$-$C_6$ alkyl, and —$SO_2$-$C_1$-$C_6$ alkyl;

$R_3$ is selected from the group consisting of H, halogen, —$CF_3$, —OH, $C_1$-$C_{10}$ alkoxy, —CHO, —CN, —$NO_2$, —$NH_2$, —NH—$C_1$-$C_6$ alkyl, —N($C_1$-$C_6$ alkyl)$_2$, —NH—$SO_2$—$C_1$-$C_6$ alkyl, and —$SO_2$—$C_1$-$C_6$ alkyl;

n in each appearance is independently an integer selected from 0–3;

$R_4$ is

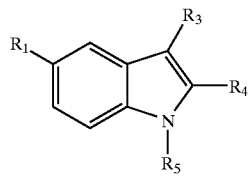

$R^{12}$ is selected from the group consisting of H, —$CF_3$, $C_1$-$C_6$ alkyl, —$(CH_2)_n$—$C_3$-$C_6$ cycloalkyl, phenyl, and benzyl, the cycloalkyl, phenyl or benzyl groups being optionally substituted by from 1 to 3 groups selected from the group consisting of halogen, —$CF_3$, —OH, —COOH, —$(CH_2)_n$—COOH, —$(CH_2)_n$—C(O)—COOH, —$C_1$-$C_6$ alkyl, —O—$C_1$-$C_6$ alkyl, —NH($C_1$-$C_6$ alkyl), and —N($C_1$-$C_6$ alkyl)$_2$;

$R_5$ is selected from the group consisting of 4-{[3,5-bis(trifluoromethyl)phenoxy]-methyl}benzyl, 3-[3,5-bis(trifluoromethyl)phenoxy]propyl, 2,4-bis(trifluoromethyl)benzyl, 4-chlorobenzyl, 2-naphthylmethyl, 4-benzylbenzyl, and 3-[3,5-bis(trifluoromethyl)phenoxy]-propyl;

provided that $R_1$, $R_{1'}$, $R_2$ and $R_3$ are not all H, or a pharmaceutically acceptable salt thereof.

2. A compound of claim 1, or a pharmaceutically acceptable salt thereof, wherein $R_1$ and $R_2$ are hydrogen.

3. A compound according to claim 1 wherein $R_{1'}$ is H and $R_1$, $R_2$, $R_3$, $R_4$, and $R_5$ are as defined in claim 1, or a pharmaceutically acceptable salt thereof.

4. A compound of claim 3 having the formula:

wherein
- $R_1$ is selected from —O—$C_1$-$C_6$ alkyl, —S—$C_1$-$C_6$ alkyl, —O-phenyl, —O-benzyl, and —S-benzyl, the alkyl, phenyl or benzyl groups being optionally substituted by from 1 to 3 substituents selected from halogen, $C_1$-$C_6$ alkyl, $C_1$-$C_6$ alkoxy, —$NO_2$, —$NH_2$, —CN, —$CF_3$, and —OH;
- $R_3$ is selected from H, halogen, —$CF_3$, —OH, —CHO, —CN, —$NO_2$, —$NH_2$, —NH—$C_1$-$C_6$ alkyl, —N($C_1$-$C_6$ alkyl)$_2$, —N—$SO_2$—$C_1$-$C_6$ alkyl, and —$SO_2$—$C_1$-$C_6$ alkyl;
- wherein $R^4$ and $R^5$ are as defined in claim 3, or a pharmaceutically acceptable salt thereof.

5. A compound of claim 1 which is 4-[(5-{(E)-[5-(benzyloxy)-1-(4-{[3,5-bis (trifluoromethyl)phenoxy]methyl}benzyl)-1H-indol-2-yl]methylidene}-2,4-dioxo-1,3-thiazolan-3-yl)methyl]benzoic acid or a pharmaceutically acceptable salt thereof.

6. A compound of claim 1 which is 5-[(E)-(5-(benzyloxy)-1-{3-[3,5-bis(trifluoromethyl)phenoxy]propyl}-1H-indol-2-yl)methylidene]-1,3-thiazolane-2,4-dione or a pharmaceutically acceptable salt thereof.

7. A compound of claim 1 which is 5-((E)-{5-(benzyloxy)-1-[2,4-bis(trifluoromethyl)benzyl]-1H-indol-2-yl}methylidene)-1,3-thiazolane-2,4-dione or a pharmaceutically acceptable salt thereof.

8. A compound of claim 1 which is 5-{(E)-[5-(benzyloxy)-1-(4-chlorobenzyl)-1H-indol-2-yl]methylidene}-1,3-thiazolane-2,4-dione or a pharmaceutically acceptable salt thereof.

9. A compound of claim 1 which is 5-{(E)-[5-(benzyloxy)-1-(2-naphthylmethyl)-1H-indol-2-yl]methylidene}-1,3-thiazolane-2,4-dione or a pharmaceutically acceptable salt thereof.

10. A compound of claim 1 which is 5-{(E)-[1-(4-benzylbenzyl)-5-(benzyloxy)-1H-indol-2-yl]methylidene}-1,3-thiazolane-2,4-dione or a pharmaceutically acceptable salt thereof.

11. A compound of claim 1 which is 2-(5-{(E)-[5-(benzyloxy)-1-(4-{[3,5-bis(trifluoromethyl)phenoxy]methyl}benzyl)-1H-indol-2-yl]methylidene}-2,4-dioxo-1,3-thiazolan-3-yl)acetic acid or a pharmaceutically acceptable salt thereof.

12. A compound of claim 1 which is 4-[(5-{(E)-[5-(benzyloxy)-1-(4-chlorobenzyl)-1H-indol-2-yl]methylidene}-2,4-dioxo-1,3-thiazolan-3-yl)methyl]benzoic acid or a pharmaceutically acceptable salt thereof.

13. A compound of claim 1 which is 2-(5-{(E)-[5-(benzyloxy)-1-(2-naphthylmethyl)-1H-indol-2yl]methylidene}-2,4-dioxo-1,3-thiazolan-3-yl)acetic acid or a pharmaceutically acceptable salt thereof.

14. A compound of claim 1 which is 4-[(5-{(E)-[5-(benzyloxy)-1-(2-naphthylmethyl)-1H-indol-2-yl]methylidene}-2,4-dioxo-1,3-thiazolan-3-yl)methyl]benzoic acid or a pharmaceutically acceptable salt thereof.

15. A compound of claim 1 which is 2-(5-{(E)-[5-(benzyloxy)-1-(4-chlorobenzyl)-1H-indol-2-yl]methylidene}-2,4-dioxo-1,3-thiazolan-3-yl)acetic acid or a pharmaceutically acceptable salt thereof.

16. A pharmaceutical composition comprising a pharmaceutically effective amount of a compound of claim 1, or a pharmaceutically acceptable salt thereof, and a pharmaceutically acceptable carrier.

17. A method of treatment for inflammation in a mammal, the method comprising administering to a mammal in need thereof a pharmaceutically effective amount of a compound of claim 1, or a pharmaceutically acceptable salt thereof.

18. A method of treatment for pain in a mammal, the method comprising administering to a mammal in need thereof a pharmaceutically effective amount of a compound of claim 1, or a pharmaceutically acceptable salt thereof.

* * * * *